US012721637B2

(12) United States Patent
Abascal Rubio et al.

(10) Patent No.: US 12,721,637 B2
(45) Date of Patent: Sep. 1, 2026

(54) RUPTURING TOOL AND RUPTURING SYSTEM FOR SURGICAL INTERVENTIONS

(71) Applicant: Abanza Tecnomed, S.L., Mutilva (ES)

(72) Inventors: José Manuel Abascal Rubio, Pamplona (ES); Juan Abascal Azanza, Mutilva-Aranguren (ES); Ander Menaut Beltrán, Subiza (ES); Alejandro Maya Pabolaza, Pamplona (ES)

(73) Assignee: Abanza Tecnomed, S.L., Mutilva (ES)

( * ) Notice: Subject to any disclaimer, the term of this patent is extended or adjusted under 35 U.S.C. 154(b) by 0 days.

(21) Appl. No.: 19/117,703

(22) PCT Filed: Oct. 4, 2023

(86) PCT No.: PCT/EP2023/077444
§ 371 (c)(1),
(2) Date: Apr. 2, 2025

(87) PCT Pub. No.: WO2024/074549
PCT Pub. Date: Apr. 11, 2024

(65) Prior Publication Data

US 2026/0108259 A1 Apr. 23, 2026

(30) Foreign Application Priority Data

Oct. 5, 2022 (EP) .................................... 22382932

(51) Int. Cl.
*A61B 17/17* (2006.01)
*A61B 17/16* (2006.01)
*A61B 17/32* (2006.01)

(52) U.S. Cl.
CPC ...... *A61B 17/1714* (2013.01); *A61B 17/1617* (2013.01); *A61B 17/1628* (2013.01);
(Continued)

(58) Field of Classification Search
CPC ................ A61B 17/1642; A61B 2017/320056
See application file for complete search history.

(56) References Cited

U.S. PATENT DOCUMENTS 1,630,239 A * 5/1927 Binkley ............ A61B 17/1688 606/180
4,992,010 A * 2/1991 Fischer .............. B23B 51/0045 175/286
(Continued)

FOREIGN PATENT DOCUMENTS

| | | | |
|---|---|---|---|
| EP | 3141216 | B1 | 3/2021 |
| EP | 3897455 | A1 | 10/2021 |
| WO | 2008096363 | A2 | 8/2008 |

OTHER PUBLICATIONS

International Search Report and Written Opinion for PCT/EP2023/077444; mailed Dec. 5, 2023; 9 pages.

*Primary Examiner* — David W Bates
(74) *Attorney, Agent, or Firm* — Fredrikson & Byron, P.A.

(57) ABSTRACT

The present invention relates to a rupturing tool for surgical interventions and to a rupturing system comprising the rupturing tool and a rupturing movement generator device. The rupturing tool and system are intended for the field of traumatology, particularly to the creation of bone tunnels suitable for the proper anatomical reconstruction of tendons and ligaments; for example, for the creation of bone tunnels in interventions for reinserting the supraspinatus muscle tendon of the rotator cuff of the shoulder joint or in interventions for reconstructing the anterior cruciate ligament (ACL) of the knee joint.

19 Claims, 33 Drawing Sheets

(52) U.S. Cl.
CPC ...... *A61B 17/1633* (2013.01); *A61B 17/1642* (2013.01); *A61B 17/320068* (2013.01); *A61B 2017/320056* (2013.01)

(56) References Cited

U.S. PATENT DOCUMENTS

| | | | | |
|---|---|---|---|---|
| 5,431,671 | A * | 7/1995 | Nallakrishnan ....... | A61F 9/0133 30/162 |
| 5,591,170 | A * | 1/1997 | Spievack ............. | A61B 17/142 606/177 |
| 5,630,824 | A | 5/1997 | Hart | |
| 6,053,922 | A | 4/2000 | Krause et al. | |
| 6,322,565 | B1 | 11/2001 | Garner et al. | |
| 6,746,451 | B2 * | 6/2004 | Middleton ......... | A61B 17/1664 606/180 |
| 6,923,813 | B2 * | 8/2005 | Phillips .......... | A61B 17/320016 606/86 R |
| 7,641,664 | B2 * | 1/2010 | Pagano .............. | A61B 17/8858 606/92 |
| 7,896,879 | B2 * | 3/2011 | Solsberg ............ | A61B 17/0401 606/79 |
| 8,663,227 | B2 * | 3/2014 | To .................. | A61B 17/320016 606/79 |
| 10,441,295 | B2 * | 10/2019 | Brockman ......... | A61B 17/1642 |
| 2006/0149268 | A1 * | 7/2006 | Truckai ................ | A61M 1/842 606/79 |
| 2008/0114364 | A1 * | 5/2008 | Goldin ............... | A61B 17/1617 606/170 |
| 2008/0208196 | A1 * | 8/2008 | Daum .............. | A61B 17/32002 606/80 |
| 2010/0042104 | A1 * | 2/2010 | Kota .................. | A61B 17/1631 606/79 |
| 2010/0191248 | A1 * | 7/2010 | Mehta ................ | A61B 17/1631 606/96 |
| 2010/0211076 | A1 * | 8/2010 | Germain ............ | A61B 18/1492 606/84 |
| 2010/0268234 | A1 * | 10/2010 | Aho ................... | A61B 17/1631 606/80 |
| 2010/0298832 | A1 * | 11/2010 | Lau .................... | A61B 17/8819 606/86 R |
| 2011/0166575 | A1 * | 7/2011 | Assell .............. | A61B 17/32002 606/79 |
| 2012/0191094 | A1 * | 7/2012 | Alain ................. | A61B 17/1671 606/80 |
| 2014/0046245 | A1 * | 2/2014 | Cornacchia ........ | A61B 17/1617 604/22 |
| 2014/0172000 | A1 * | 6/2014 | Kuntz ................ | A61B 17/1642 606/167 |
| 2015/0127012 | A1 * | 5/2015 | Pilgeram ............ | A61B 17/1714 606/88 |
| 2016/0278791 | A1 * | 9/2016 | Pellegrino .......... | A61B 17/1642 |
| 2019/0192278 | A1 | 6/2019 | Smigielski et al. | |
| 2023/0190308 | A1 * | 6/2023 | Bhatia ................ | A61B 17/1617 606/79 |

* cited by examiner

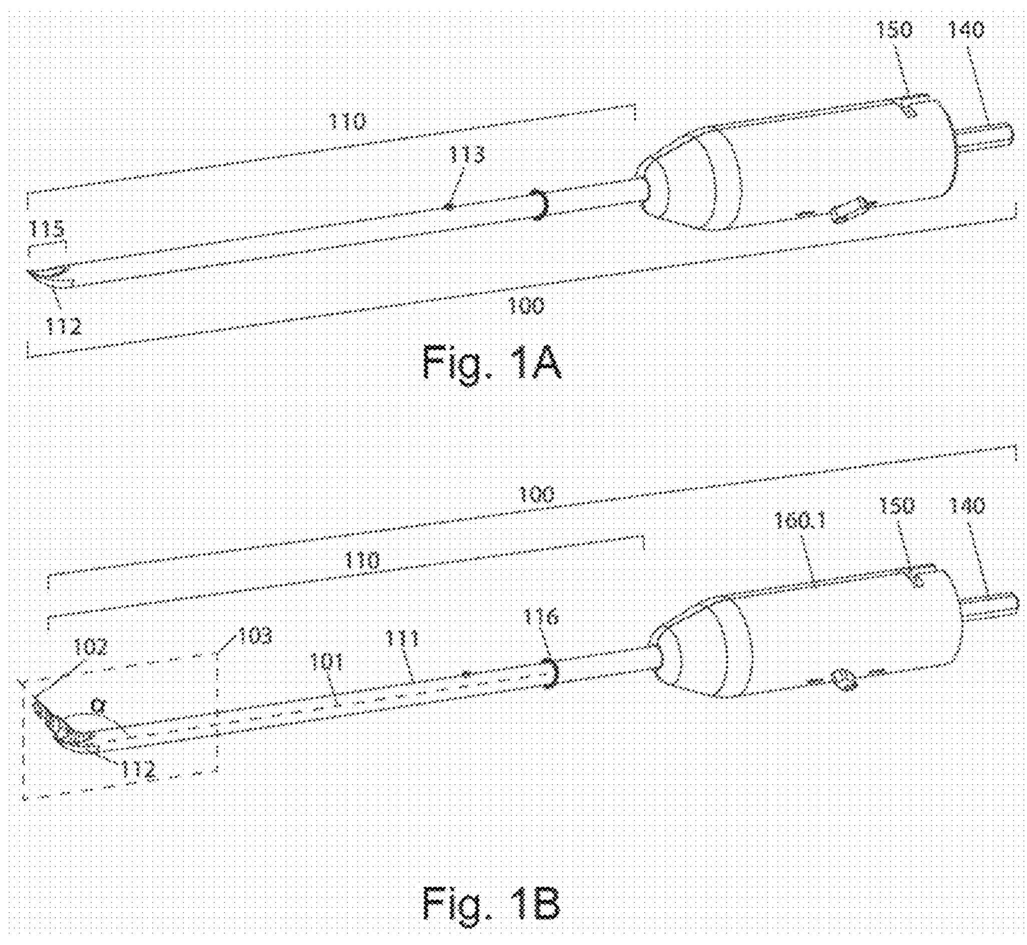
Fig. 1A
Fig. 1B
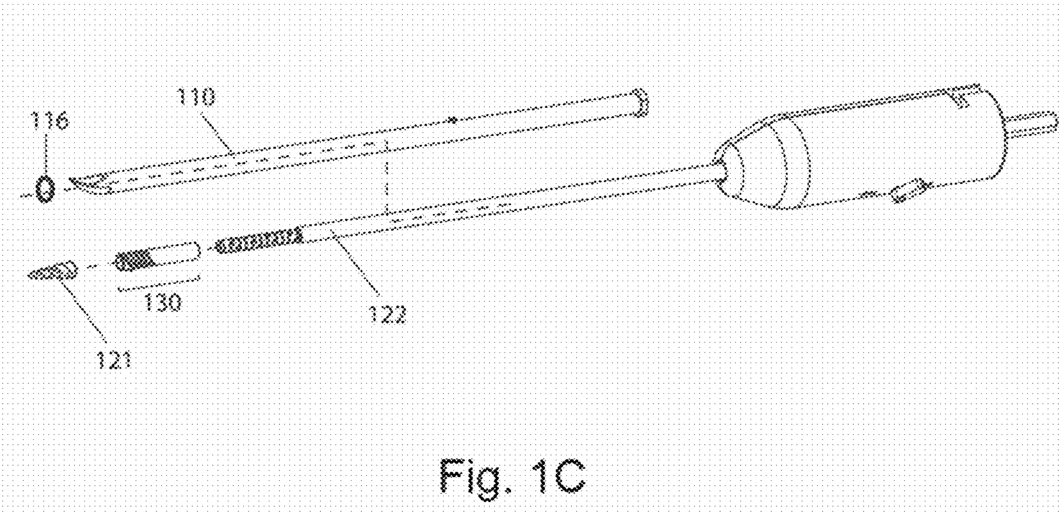
Fig. 1C

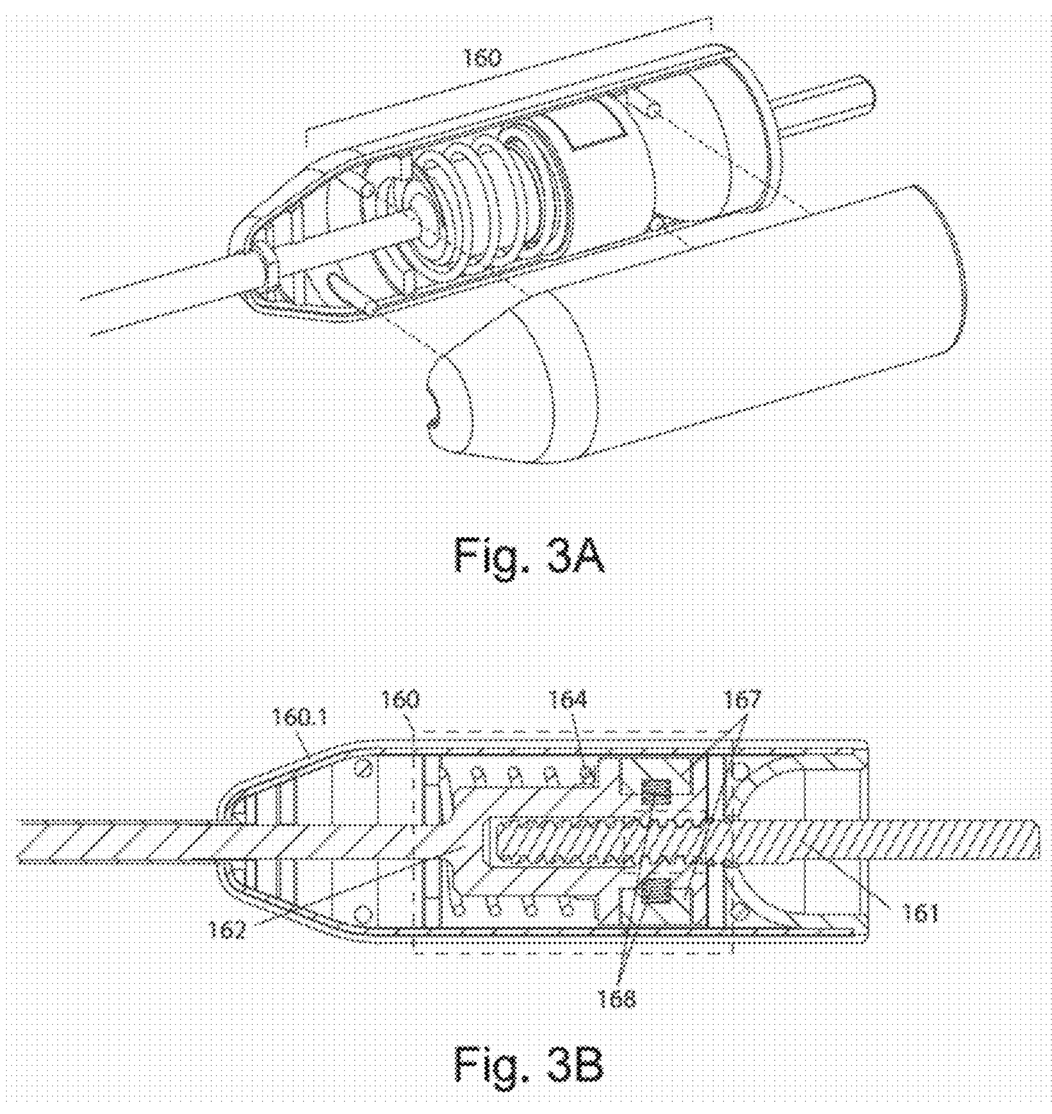
Fig. 3A
Fig. 3B
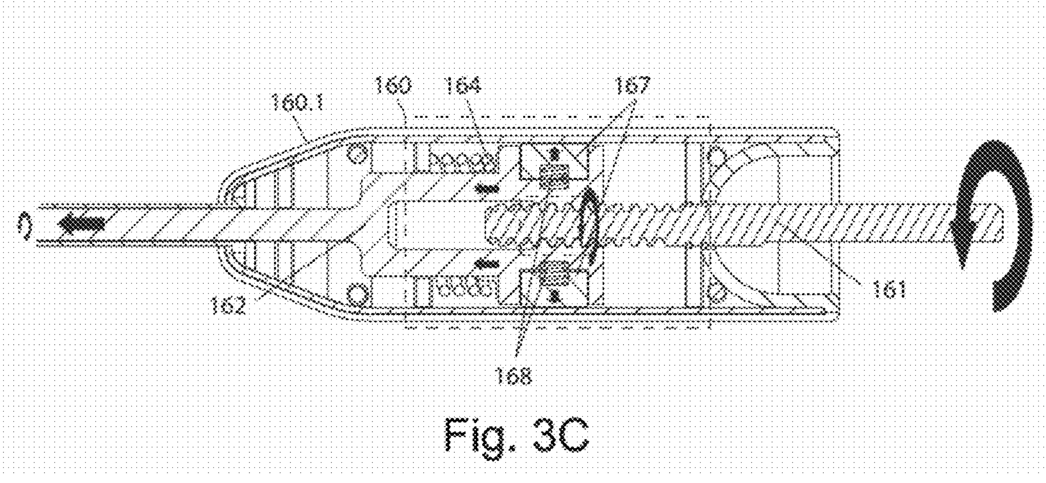
Fig. 3C

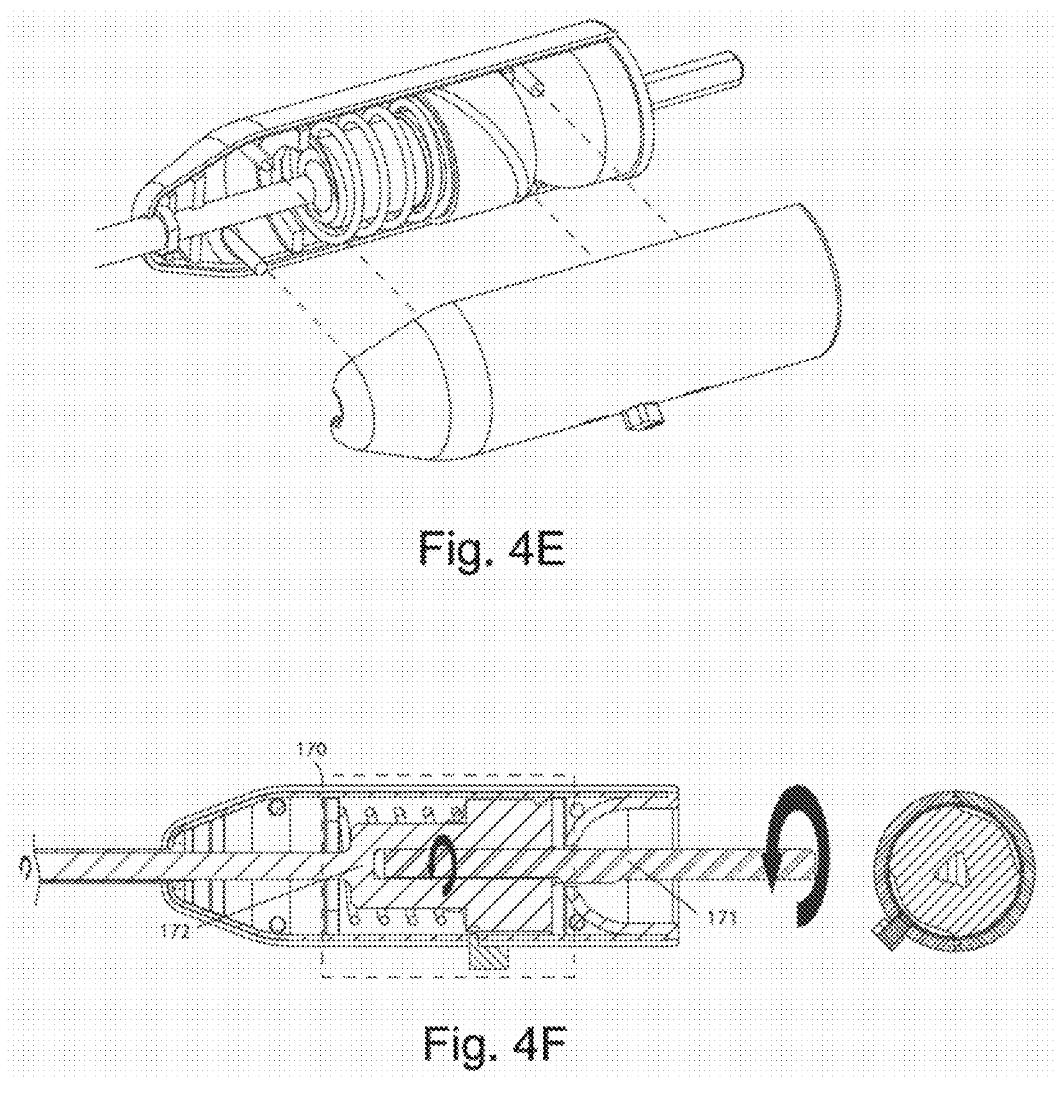
Fig. 4E
Fig. 4F
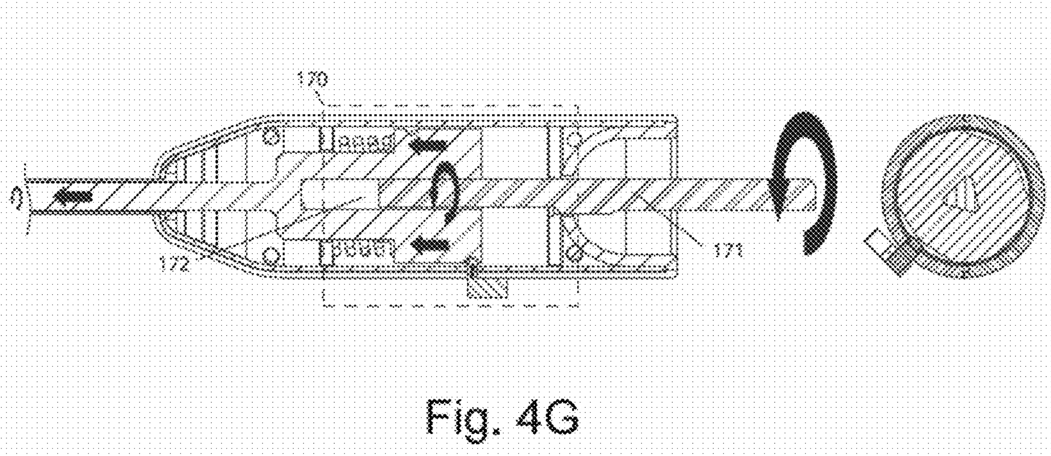
Fig. 4G

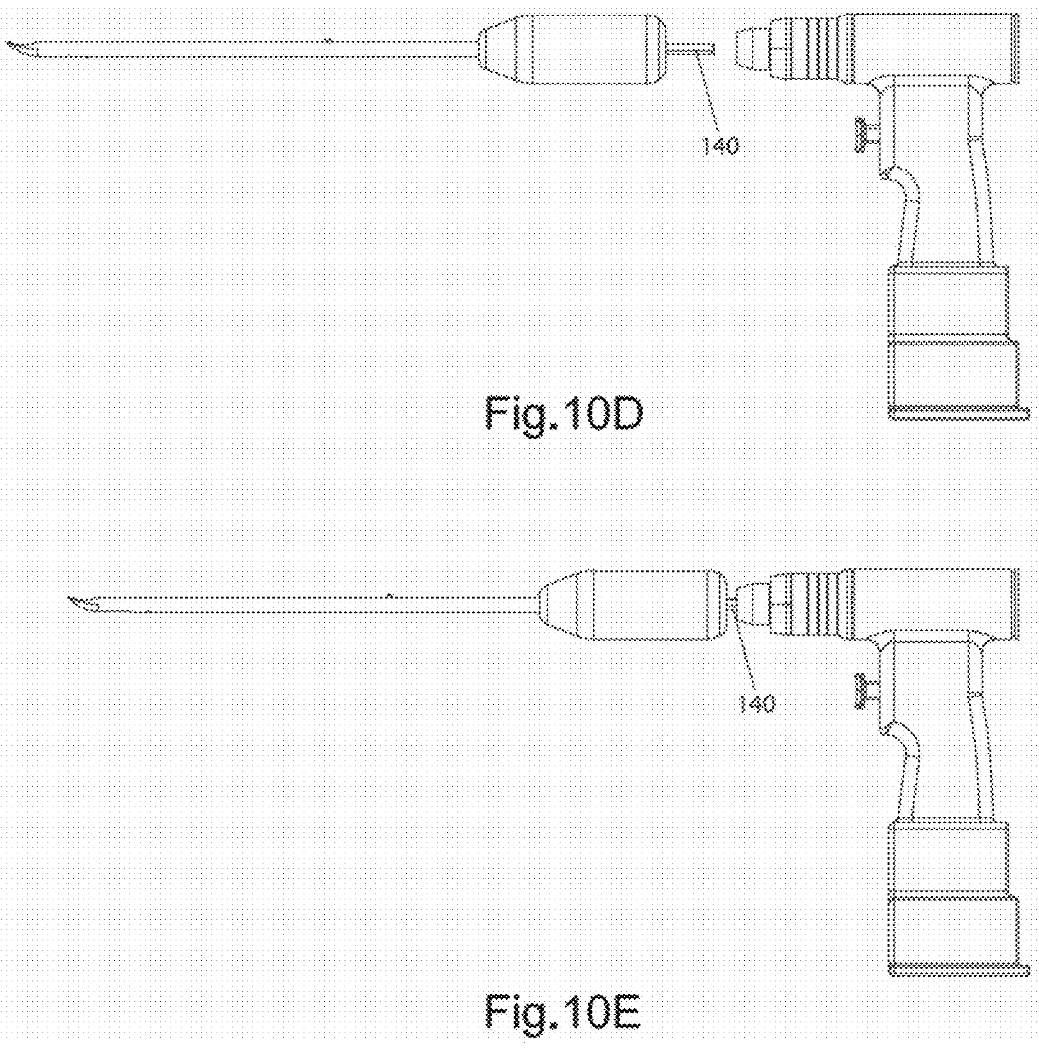
Fig.10D
Fig.10E
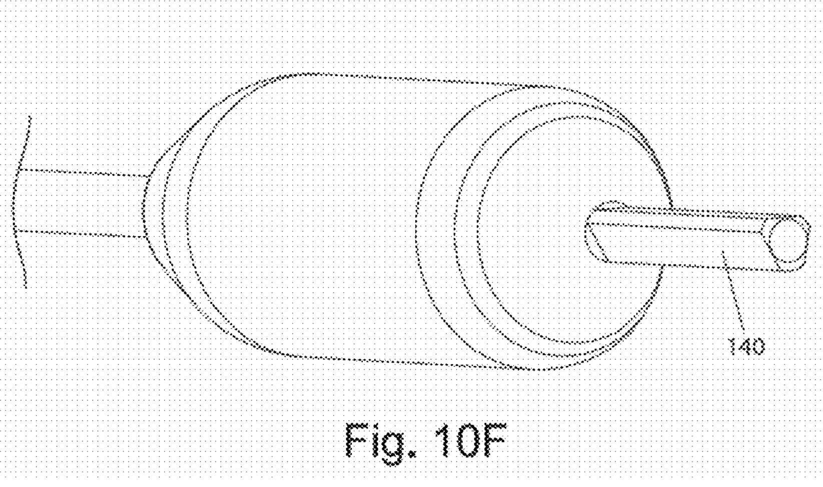
Fig. 10F

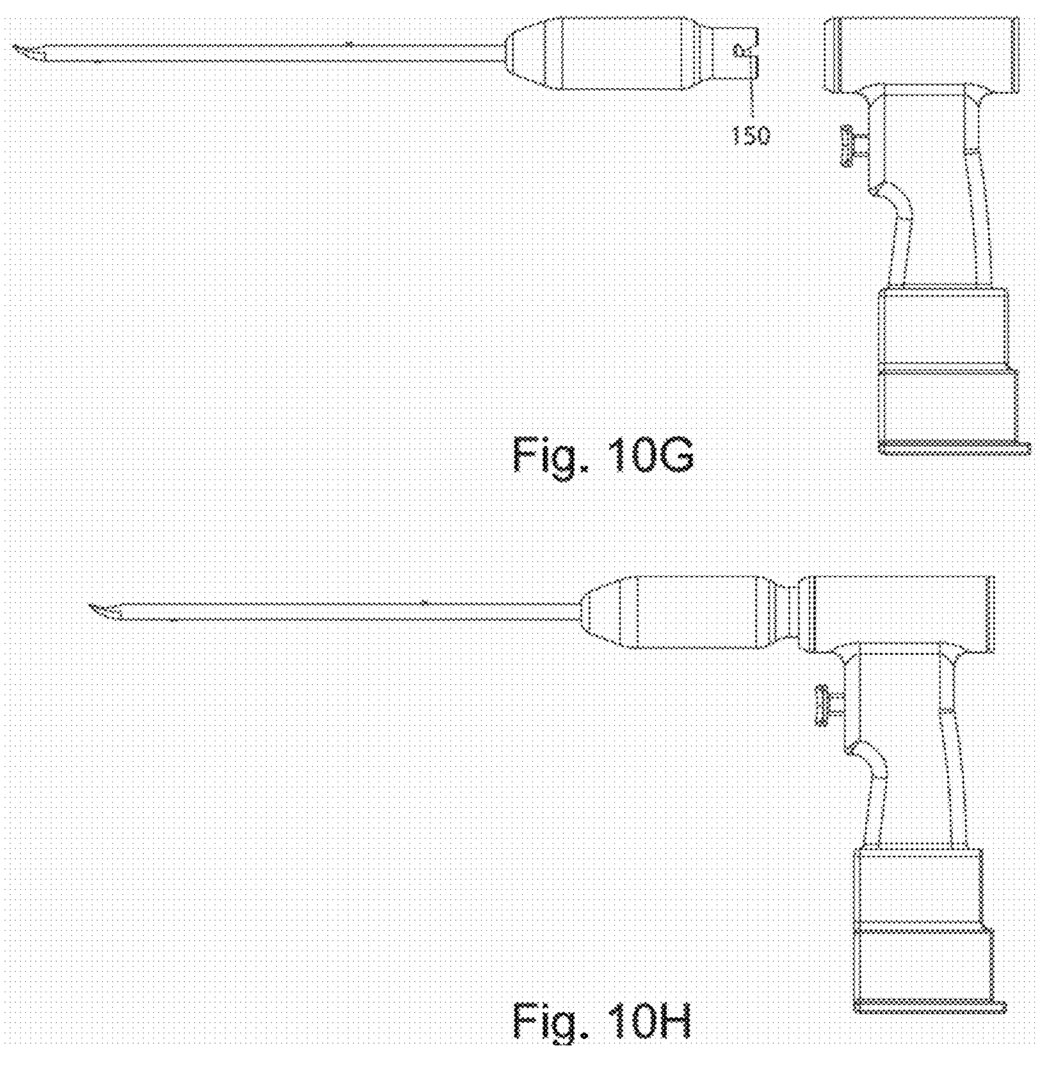
Fig. 10G
Fig. 10H
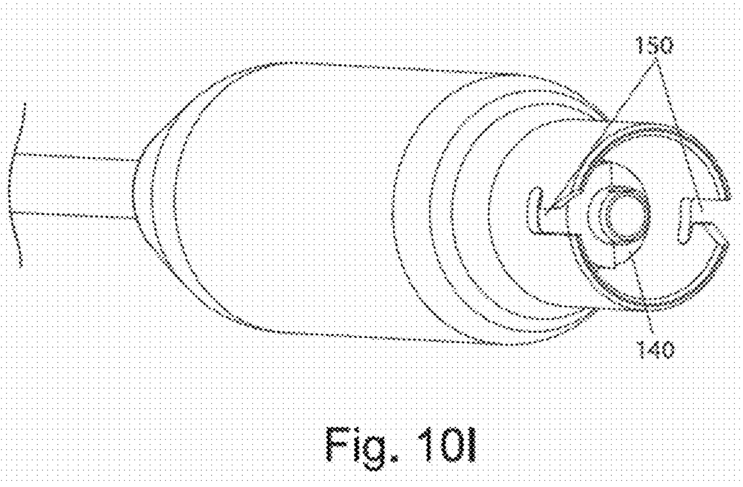
Fig. 10I

RUPTURING TOOL AND RUPTURING SYSTEM FOR SURGICAL INTERVENTIONS

CROSS-REFERENCE

This application is a 35 U.S.C. 371 national stage filing from International Application PCT/EP2023/077444, filed Oct. 4, 2023, which claims priority to European Patent Application No. 22382932.6, filed Oct. 5, 2022. The entire context of each of these applications are incorporated herein by reference.

CROSS-REFERENCE

This application is a 35 U.S.C. 371 national stage filing from International Application PCT/EP2023/077444, filed Oct. 4, 2023, which claims priority to European Patent Application No. 22382932.6, filed Oct. 5, 2022. The entire context of each of these applications are incorporated herein by reference.

OBJECT OF THE INVENTION

The present invention relates to a rupturing tool for surgical interventions and to a rupturing system comprising the rupturing tool and a rupturing movement generator device. The rupturing tool and system are intended for the field of traumatology, particularly to the creation of bone tunnels suitable for the proper anatomical reconstruction of tendons and ligaments; for example, for the creation of bone tunnels in interventions for reinserting the supraspinatus muscle tendon of the rotator cuff of the shoulder joint or in interventions for reconstructing the anterior cruciate ligament (ACL) of the knee joint.

BACKGROUND OF THE INVENTION

One of the most common injuries in the field of traumatology is joint tendon and ligament ruptures.

Among the most common tendon ruptures are tendon rupture in the rotator cuff of the shoulder, mainly the supraspinatus muscle tendon. This injury represents the main cause of shoulder instability and is present in 20.7% of the general population, with a prevalence that increases with age ("*Prevalence and risk factors of a rotator cuff tear in the general population*", Yamamoto A et al/*J Shoulder Elbow Surg.* 2010 January; 19(1):116-20).

Screws which are screwed into the head of the humerus are often used during supraspinatus tendon reconstruction surgery. These screws carry suture threads or suture bands, which are passed through the damaged end of the tendon, in order to pull on it, reposition it, and fix it on the original area of insertion.

In many cases, a problem which prevents a successful reconstruction is that the screws carrying the sutures only provide surface compression at the end of the tendon, on the original area of insertion of the tendon, an area which is furthermore reduced by the screw itself, such that the healing process is hindered. If the tendon does not heal, the surgery is inadequate because it is not only intended for repositioning the tendon in the bone, but also for promoting the tendon-bone healing process for a proper reconstruction of said damaged tendon (Castagna et al. 2018, *Arthroscopic Transosseous Rotator Cuff Repair*).

The solution to this problem requires creating an angled bone tunnel by means of minimally invasive surgery for the passage of sutures and carving a bone housing along the original anatomical area of insertion, intended for the insertion of the damaged end of the tendon and/or of the augmentation tissue used for repair, which cannot be done with the flexible rupturing tools existing in the state of the art today.

These rupturing tools have flexible shafts and curved or angled trajectories, like the one disclosed in U.S. Pat. No. 6,053,922, which describes a flexible rupturing tool intended for the reaming of the medullary canal in bones; or like the one described in U.S. Pat. No. 6,322,565, intended for the creation of channels for blood supply to the femoral head. These flexible rupturing tools and other similar tools of the state of the art allow a curved or angled bone tunnel to be created by moving in a specific milling direction, from a first position to a second position.

However, when these rupturing tools in the second position are to be used in a direction different from the initial milling direction, the tools are unmanageable because, in this second position, the rupturing element lacks the rigidity required for carving the bone, which is necessary in the mentioned tendon repair or restoration surgery.

With respect to ligaments, the rupture of knee joint cruciate ligaments, mainly the anterior cruciate ligament (ACL), which occurs in patients of all ages, stands out as the most common ruptures.

In most cases, patients suffering from an ACL rupture must undergo a surgical procedure consisting of removing the damaged ACL and replacing it with an implant, the two ends of which are implanted and fixed in respective tibial and femoral bone tunnels.

As with tendons, to achieve anatomical ACL reconstruction, a system which allows restoring the original areas of insertion must be provided. Unfortunately, with the current techniques, 80% of patients develop osteoarthritis between 15 and 20 years after surgery.

To successfully restore anatomical bone insertions of the original ACL, solutions describing arthroscopic guides which allow creating two or more contiguous bone tunnels that are subsequently attached by means of dilator are known in the current state of the art. For example, document US 2019/0192278 describes an arthroscopic guide which allows creating three contiguous bone tunnels that are subsequently attached by means of a dilator.

However, a first problem associated with multi-tunnel rupturing systems of this type is that the tibia cannot be accessed "from the inside out", so they do not allow carrying out the "all-in" cruciate ligament anatomical reconstruction techniques. A second problem is that, by accessing the lateral condyle of the femur through the medial portal, it is impossible to make a sufficiently transverse femoral bone tunnel, so the degrees of twisting with respect to the original ACL are lost. The consequences of failing to completely restore the twisting biomechanics of the original ACL are widely described in the literature: rotational instability of the knee and a medium-term degenerative arthrosis.

The solution to this problem requires creating a bone tunnel for the passage of sutures and carving a bone housing along the original anatomical area of insertion, intended for the insertion of the implant used for reconstructing the damaged ligament, which is not possible with the flexible rupturing tools of the state of the art mentioned above.

Document WO 2008/096363 A2 describes a bone drill for the creation of a bone tunnel of two diameters.

Therefore, in view of these problems, there is a need to provide rupturing tools which, when used in minimally invasive surgeries, allow carving bone housings along the original anatomical areas of insertion of the tendons and ligaments under reconstruction.

DESCRIPTION OF THE INVENTION

The present invention proposes a solution to the preceding problems by means of a rupturing tool for surgical interventions according to claim 1 and rupturing systems for surgical interventions according to claims 17 and 18. The dependent claims define preferred embodiments of the invention.

The invention provides a rupturing tool for minimally invasive surgical interventions for the creation of bone tunnels suitable for the proper anatomical reconstruction of tendons and ligaments, comprising:

- a longitudinal body which in turn comprises
  - a main body oriented according to a first longitudinal axis; and
  - a distal tip attached to the main body comprising an opening oriented according to at least one second longitudinal axis, the distal tip forming a ramp with respect to the main body;

wherein the first longitudinal axis and the at least one second longitudinal axis form with respect to one another an angle $\alpha$ greater than zero degrees, and wherein the first longitudinal axis and the at least one second longitudinal axis are comprised in a first sagittal plane;

- a rupturing assembly comprising:
  - a rupturing element comprising a first axis of rupture and configured for receiving and performing a rupturing movement about the first axis of rupture and for receiving and performing a linear movement, moving along the longitudinal body from a first position to at least one second position, and vice versa, wherein:
    - if the rupturing element is located in the first position, the rupturing element is oriented according to the first longitudinal axis inside the main body; and
    - if the rupturing element is located in the second position, the rupturing element is oriented according to the at least one second longitudinal axis protruding at least partially through the opening of the distal tip; and
  - a movement transfer element, comprising a proximal part, a flexible or articulated distal part, and a second axis of rupture, the movement transfer element being securely attached to the rupturing element by the flexible or articulated distal part and being configured for:
    - receiving and performing a rupturing movement about the second axis of rupture and for transferring the rupturing movement to the rupturing element; and
    - receiving and performing a linear movement, moving along the longitudinal body; and for transferring the linear movement to the rupturing element;
- at least one rigidity provision means configured for providing rigidity to the rupturing assembly when the rupturing element is located in the second position protruding at least partially through the opening of the distal tip, wherein the rigidity provision means comprises a tubulated element which in turn comprises a proximal portion and a distal portion; wherein the tubulated element: is sized and configured for moving along the longitudinal body;

is sized and configured for housing at least partially therein the flexible or articulated distal part of the movement transfer element, is configured for orienting the distal portion according to the first longitudinal axis when the rupturing element is located in the first position; and is configured for orienting the distal portion according to the at least one second longitudinal axis when the rupturing element is located in the at least one second position.

The rupturing tool of the invention allows creating bone tunnels suitable for the anatomical reconstruction of damaged tendons and/or ligaments. In particular, the tool allows creating bone tunnels with elongated, for example, straight, curved, or angled, intraarticular outlet openings similar to the original anatomical areas of insertion, capable of housing the tendon or ligament under reconstruction at a bone depth enough to ensure its regeneration. A restoration that favors osteointegration is thus achieved.

Throughout this document, tendons shall be understood to mean bands of connective tissue configured for attaching muscles to bones and ligaments shall be understood to mean bands of connective tissue configured for attaching bones to one another.

Throughout this document, the proximal end of an element of the tool (or of the system) shall be understood to mean the end closer to the subject using said tool.

In contrast, the distal end of an element of the tool (or of the system) shall be understood to mean the end farther away from the subject using said tool. Preferably, the subject or user is a doctor, a veterinarian, or a medical or veterinary professional.

First, the tool comprises a longitudinal body. "Longitudinal" shall be understood to mean that the body is made or placed in the lengthwise direction thereof. Preferably, the longitudinal body is tubular; in other words, a hollow body in the shape of a tube generally open at both ends. In other embodiments, the longitudinal body is formed as a concave channel or conduit.

This longitudinal body in turn comprises

- a main body oriented according to a first longitudinal axis; and
- a distal tip attached to the main body comprising an opening oriented according to at least one second longitudinal axis.

The tip is a small, ramp-forming portion which is preferably straight or curved with respect to the main body. The angulation of said ramp is given by the angle formed between the first longitudinal axis, according to which the main body is oriented, and the at least one second longitudinal axis, according to which the opening of the tip is oriented.

Throughout the document, the expression "the distal tip is attached to the main body" shall be understood to mean that said distal tip and said main body are in contact forming a whole, that is, the longitudinal body. Said contact can be complete, with the distal tip being completely adhered to the main body, such that they both form a one-piece assembly, or the distal tip can be partially in contact with the main body through an attachment means, such as a hinge or a ratchet system.

Throughout the document, "at least one second longitudinal axis" shall be understood to mean one or more longitudinal axes, depending on whether the tip can form one or more different angles with the main body. In particular, if the tip is completely adhered to the main body, the first longitudinal axis and the second longitudinal axis will form a specific angle $\alpha$ equal to or greater than zero degrees with respect to one another. If, in contrast, the contact between both elements is partial, the attachment means allows the tip to be positioned in a plurality of different positions such that the first longitudinal axis forms a different angle $\alpha_i$ with each second longitudinal axis, with each of the angles $\alpha_i$ being equal to or greater than zero degrees.

The first longitudinal axis and the at least one second longitudinal axis are comprised in a first sagittal plane. Throughout the document, “sagittal plane” shall be understood to mean the plane which is perpendicular to the ground and divides a body or element into a left half and a right half. This terminology is commonly used in the field of anatomy.

Second, the tool comprises a rupturing assembly. Said assembly in turn comprises a rupturing element and a movement transfer element attached to one another.

Throughout the document, “rupturing element” shall be understood to mean any type of element capable of breaking, milling, cutting, reaming, polishing, compacting, or perforating a biological tissue; particularly bone tissue.

In a particular example, the rupturing element is a mill, a rupturing mill, a bit, a blade, a scraper, a rasp, a vibrating rupturing element, or a reciprocating rupturing and/or compacting element.

In another particular example, the rupturing element is a compacting mill which causes bone densification which is important for early loading, allowing the rehabilitation time required to return to the pre-injury activity level to be shortened.

In other more particular examples, the rupturing element:

- has a frustoconical geometry, with a proximal diameter greater than the distal diameter;
- has a cylindrical geometry;
- is a mixed element, wherein the proximal segment is a compacting segment and the distal segment is a rupturing segment;
- has a distal cross-section that is circular, elliptical, polygonal, trilobular, or corresponds to any other geometric figure.

This rupturing element comprises a first axis of rupture; for example, an axis of rotation about which the element performs a rotation or an axis of vibration about which the element performs a vibratory movement. Said element is configured for receiving and performing a rupturing movement; being understood to be a movement which can be performed by the rupturing element such that said element can break a human tissue, preferably bone. Examples of rupturing movement are a rotational and/or reciprocating and/or vibrating movement performed about the first axis of rupture. Additionally, the rupturing element is configured for receiving and performing a linear movement, moving along the longitudinal body (particularly along the inside thereof if the longitudinal body is tubular) from a first position to at least one second position, and vice versa. Throughout the document, “at least one second position” shall be understood to mean the one or more positions in which the rupturing element can be located based on the location of the distal tip, depending on whether the tip can form one or more different angles with the main body, as mentioned above.

The rupturing element exits through the opening of the distal tip in the sagittal plane comprising the first longitudinal axis and the at least one second longitudinal axis Throughout the document, rotary or rotational movement shall be understood to mean the movement in which the rupturing element performs a constant 360-degree rotation. Rotary reciprocating movement shall be understood to mean the movement in which the rupturing element alternately performs a rotary forward movement and a rotary backward movement, preferably of 180 degrees, such that it rotates and moves linearly and alternately in the proximal-distal and distal-proximal directions. Vibrating or vibratory movement shall be understood to mean the movement in which the rupturing element performs a periodic movement oscillating about a stable equilibrium position, such that it moves between two end positions.

In the first position, the rupturing element is oriented according to the first longitudinal axis, that is, the rupturing element remains housed inside the main body. In the second position, the rupturing element is oriented according to the second longitudinal axis or one of the second longitudinal axes, that is, the rupturing element protrudes at least partially through the opening of the distal tip towards the outside of the tool. In this second position, the rupturing element will be oriented according to the second longitudinal axis in the case where the distal tip and the main body form a one-piece assembly. In the case where the distal tip is attached to the main body by means of an attachment element which allows positioning it in a plurality of different angular positions (such that for each of said plurality of angular positions, the at least one second longitudinal axis forms a different angle $\alpha$ with the first longitudinal axis), the rupturing element will be oriented according to one of the second longitudinal axes.

As a result of this second position in which the rupturing element is oriented, an angled bone tunnel formed by two consecutive segments can be carved, with said segments being angled with respect to one another an angle $\alpha$. Even more advantageously, said angle $\alpha$ can be previously decided with the same tool depending on the application (medicine or veterinary), on the specific surgery to be performed, and on the anatomy of the patient itself.

To enable positioning this rupturing element in said first and second positions, the rupturing assembly further comprises a movement transfer element. This movement transfer element comprises a second axis of rupture about which it performs a rupturing movement, and two parts or portions: a proximal part, which can be both rigid and flexible, and a flexible or articulated distal part. Both parts either form a one-piece assembly or can be attached through an attachment means, for example, by means of screws. Preferably, the movement transfer element is an elongated cylinder, with the proximal part having a cross-section with a larger diameter than the flexible or articulated distal part.

This movement transfer element is attached to the rupturing element; in particular, the distal end of the flexible or articulated distal part is securely attached to the proximal end of the rupturing element.

This movement transfer element is configured for:

- receiving a rupturing movement, for example a rotary or vibratory movement, and performing said rupturing movement about the second axis of rupture;
- transferring the rupturing movement to the rupturing element;
- receiving a linear movement and performing same, such that it moves along the longitudinal body (particularly along the inside thereof if the longitudinal body is tubular); and
- transferring the linear movement to the rupturing element, such that it moves from the first position to the second position (and from the second position to the first position when movement transfer ceases).

In one example, the flexibility of the movement transfer element is due to a braided configuration of the element. In another example, the flexibility of the movement transfer element is due to a tubular configuration comprising cuts and/or openings in the element. In another example, the flexibility of the movement transfer element is due to said element comprising a superelastic nitinol braided core and an outer polymer layer.

As a result of the movement transfer element being flexible or articulated, when it performs the linear movement in the proximal-distal direction, the flexible or articulated distal part thereof is located in the distal tip of the longitudinal body, acquiring a curved shape, such that the rupturing element attached to said flexible or articulated part projects or protrudes at least partially through the opening of the distal tip towards the outside of the tool, being oriented according to the second longitudinal axis or one of the second longitudinal axes.

This flexibility is only in the sagittal plane. In contrast, for the other planes, this flexible or articulated part of the movement transfer element acquires rigidity as a result of the third component of the tool. This component is the so-called rigidity provision means, which is configured for providing rigidity to the rupturing assembly, particularly to the mentioned flexible or articulated distal part of the movement transfer element, in every plane other than the first sagittal plane when the rupturing element is located in the at least one second position.

This rigidity is essential so that the tool, when in use, has sufficient force to break the bone, and can therefore carve a bone tunnel with the desired shape.

The rigidity provision means comprises a tubulated element which in turn comprises a proximal portion and a distal portion; wherein the tubulated element:

- is sized and configured for moving along the longitudinal body;
- is sized and configured for housing at least partially therein the flexible or articulated distal part of the movement transfer element,
- is configured for orienting the distal portion according to the first longitudinal axis when the rupturing element is located in the first position; and
- is configured for orienting the distal portion according to the at least one second longitudinal axis when the rupturing element is located in the at least one second position.

The rigidity provision means comprises a tubulated element, that is, tubular or in the shape of a tube, which is attached to the flexible or articulated part of the movement transfer element, housing said flexible or articulated part therein. In turn, the tubulated element has dimensions suitable for being housed inside the longitudinal body and being able to move along said body (particularly along the inside thereof if the longitudinal body is tubular). This movement is possible because the tubulated element houses therein the movement transfer element; that is, when the movement transfer element moves linearly in the proximal-distal direction, the tubulated element also moves integrally.

Before said movement takes place, that is, when the rupturing element is in the first position, the two portions of the tubulated element are oriented according to the first longitudinal axis, since they are positioned inside the main body. Once the movement has taken place, that is, when the rupturing element is in the second position, only the proximal portion of the tubulated element remains oriented according to the first longitudinal axis (that is, it is still located inside the main body), whereas the distal portion of the tubulated element is oriented according to the second longitudinal axis or one of the second longitudinal axes (that is, this distal portion is positioned in the distal tip of the tool, acquiring a curved shape).

In a first example of use, the rupturing tool, yet to be activated, is introduced in a straight bone tunnel having a single previously carved segment (in accordance with the first longitudinal axis). Once introduced, the rupturing tool is activated such that, when the movement transfer element receives a rupturing movement and a linear movement, it transfers same to the rupturing element, causing it to move from the first position to the second position, performing at the same time the rupturing movement. The rupturing element therefore protrudes at least partially through the opening of the tip of the tool, carving a second segment of the bone tunnel in accordance with the second longitudinal axis.

At this point, by keeping the tool activated, the user can turn said tool from left to right and/or vice versa such that the rupturing element breaks the bone and a widened intraarticular outlet opening can therefore be carved in said bone tunnel, with a geometry similar to the geometry of the original anatomical areas of insertion of a tendon being repaired. For example, an elongated intraarticular outlet opening with a funnel-shaped and/or rectangular geometry can be carved for the reinsertion of a supraspinatus tendon being repaired.

The left to right movement and/or vice versa should be understood to mean a movement performed with respect to the first sagittal plane of the tool initially positioned in the straight bone tunnel having a single segment.

Advantageously, such anatomical widenings created with the tool greatly favor tissue healing, which means that the operation is effective and its result is long-lasting.

In a particular example of repairing the damaged supraspinatus muscle tendon of the rotator cuff, the intraarticular outlet opening of the bone tunnel to be created must be such that they allow the insertion of the end of the damaged tendon which, at the height of the rotator chord, has measurements of between 4 mm and 5 mm in thickness and between 20 mm and 25 mm in width.

These particular measurement ranges provided in this example of use must be adapted based on the final application for which the rupturing tool is used.

In a second example of use, the rupturing tool of the invention allows the rupturing element to be introduced in a straight bone tunnel in a first position in which the rupturing element is oriented according to the first longitudinal axis, and then, the rupturing element moving linearly forward to a second position in which the rupturing element is oriented according to at least one second longitudinal axis, the user can carve and/or retrocarve a widened intraarticular outlet opening in said bone tunnel, with a geometry similar to the geometry of the original anatomical area of insertion of a ligament being restored. For example, an elongated intraarticular outlet opening with a funnel-shaped and/or rectangular geometry can be carved and/or retrocarved for ACL restoration.

In a particular example of ACL reconstruction, the intraarticular outlet opening of the bone tunnel to be created must be such that it allows the insertion of the fibrous substance, having measurements of between 2 and 4 mm in thickness and between 12 mm and 18 mm in width.

These particular measurement ranges provided in the second example of use must be adapted based on the final application for which the rupturing tool is used.

In a general use, the rupturing tool is suitable for rupturing any connective tissue and/or cartilage tissue and/or bone tissue, in medicine or veterinary.

In a particular example of use, the rupturing tool is suitable for creating and/or carving all types of tunnels in surgical interventions for the reconstruction of any connective tissue and/or cartilage tissue and/or bone tissue, in medicine or veterinary.

In another more particular example of use, the rupturing tool is suitable for creating a space of selected shape and dimensions by means of the efficient rupture and elimination of tissue from the intervertebral disk, during minimally invasive vertebral discectomies.

In one embodiment, the rupturing tool is disposable.

In a particular embodiment, the rupturing tool comprises a suction line couplable to an external suction device for the removal of broken tissue. In this embodiment, both the rupturing element and the movement transmission shaft are cannulated, and the rupturing element comprises a distal suction window for suctioning bone dust simultaneously with bone carving. In an even more particular embodiment, the external suction device comprises a vacuum system.

In a particular embodiment, the distal tip is attached to the main body:

- securely as a prolongation of said main body; or
- by means of an attachment element configured for positioning the tip in a plurality of angular positions such that, for each of said plurality of angular positions, the at least one second longitudinal axis forms a different angle $\alpha$ with the first longitudinal axis.

As mentioned above, the distal tip and the main body are in contact forming a whole, that is, the longitudinal body.

The contact can be complete, with the distal tip being completely adhered to the main body, that is, with the distal tip being a prolongation of the main body such that they both form a one-piece assembly.

Advantageously, this type of one-piece configuration is easy to manufacture and to maintain.

In contrast, the distal tip can be partially in contact with the main body through an attachment means, such as a hinge. Said attachment means furthermore allows the tip to be positioned in a plurality of angular positions, orienting it according to different second longitudinal axes each forming a different angle $\alpha$ with the first longitudinal axis.

Advantageously, this type of configuration allows the tool to be very versatile, where the angulation of the bone tunnel can be adapted to different applications, surgery types, and patients' anatomies.

In a particular embodiment, the first axis of rupture is:

- an axis of rotation about which the rupturing element performs a rotation; or
- an axis of vibration about which the rupturing element performs a vibratory movement.

In a particular embodiment, the tubulated element further comprises at least one elongated notch arranged in the distal portion forming at least one angle $\beta$ greater than 0 degrees and less than or equal to 90 degrees with respect to the first sagittal plane, wherein:

- each of the at least one elongated notch separates two different segments of the distal portion of the tubulated body; and
- the sum of the separations between segments of the tubulated body is substantially zero when the rupturing element is located in the at least one second position.

Additionally, the tubulated element comprises at least one elongated notch. Throughout the document, "notch" shall be understood to mean any cut, opening, or recess on a surface or in a solid body when it does not completely divide them. Furthermore, "elongated notch" shall be understood to mean a cut that is significantly longer than it is wide.

These notch or notches are arranged on the tubulated element in the upper part of the distal portion forming an angle $\beta$ greater than 0 degrees and less than or equal to 90 degrees with respect to the first sagittal plane. Said angle $\beta$ can be the same for all the notches, in the case where there are more than one notches or can be different.

Each of these notches separates the upper part of the distal portion into two different segments spaced by a specific separation when said distal portion is located in the main body (that is, when the rupturing element is located in the first position). The separation defined by each notch can be the same or different, provided that the total sum of the separations of all the notches is substantially zero when the distal portion of the tubulated element is located in the distal tip of the tool (that is, when the rupturing element is located in the second position).

This means that, in the first case, the notches remain open, whereas in the second case, the notches are virtually closed. In that sense, with the notches being virtually closed, the distances between segments are reduced to substantially zero, the option of there being a certain tolerance to be taken into account being understood as such.

It shall be understood that a notch is closed when its curved and/or angled edges (or in other words, the walls of consecutive segments) contact one another due to the actual curved position acquired by the tubulated element. The tubulated element therefore allows providing rigidity to the flexible or articulated distal part of the movement transfer element in all the planes with the exception of the first sagittal plane, along which said flexible part has acquired a curved shape.

In one example, the notches have a trapezoidal geometry, and/or a winding geometry, and/or a sinusoidal geometry, and/or any other geometry, provided that they are arranged forming an angle $\beta$ (or several angles $\beta$) with respect to the first sagittal plane of the rupturing tool.

In a preferred example, the tubulated element is a bushing comprising a modular system consisting of portions that are coupled to one another configuring a winding body in a single sagittal plane.

In one embodiment, the tubulated element further comprises at least one second elongated notch arranged in the lower part of its distal portion. The effect produced in this at least one second notch is in contrast to the effect produced by notches of the upper part, that is, when the rupturing element is located in the at least one second position, said at least one second notch opens such that the distance(s) between the segments in which the notch separates the lower part of the distal portion of the tubulated element increase(s).

In an alternative embodiment, the tubulated element comprises a tube made of superelastic nitinol, with or without notches, and an outer polymer layer.

In a particular embodiment, the longitudinal body further comprises at least one distal longitudinal groove and the tubulated element further comprises at least one first projection, wherein

- the at least one distal longitudinal groove comprises a distal limit and a proximal limit;
- the at least one distal longitudinal groove is sized for receiving the at least one first projection and configured for cooperating with said first projection guiding the tubulated element in the direction of the sagittal plane when the rupturing element moves from the first position to the at least one second position, and vice versa; and
- the at least one first projection is sized for penetrating the at least one distal longitudinal groove and configured for cooperating with said distal longitudinal groove, moving along the distal longitudinal groove when the rupturing element moves from the first position to the at least one second position, and vice versa; and the at least one first projection abuts with a distal limit of the at least one distal longitudinal groove when the rupturing element is located in the at least one second position.

In this embodiment, the tubulated element comprises one or more projections configured for cooperating with one or more corresponding longitudinal grooves located in the longitudinal body. Throughout the document, "projection" shall be understood to mean a part or portion of the tubulated element protruding from said element and "groove" shall be understood to mean a long and narrow channel opening inside the longitudinal body, particularly in the direction of the sagittal plane.

The projection penetrates the groove and cooperates with it to guide the tubulated element in the direction of the sagittal plane. Since the tubulated element is connected to the movement transfer element which is connected to the rupturing element, when the movement transfer element moves from the first position to the second position, the tubulated element in turn moves in the direction of the sagittal axis until abutting with the distal limit of the groove. Distal limit shall be understood to mean the end or the termination of the groove farthest away from the user. Advantageously, this projection-groove cooperation prevents the tubulated element from rotating about itself or from moving in an undesired manner, which would cause the rupturing assembly to not be able to be suitably positioned and oriented. If this occurs, the rupturing element could not be positioned in the second position to carve the second segment of the bone tunnel, nor would it have the sufficient rigidity to carve the widened intraarticular outlet opening.

In a particular embodiment, the rupturing tool further comprises at least one first attachment and/or coupling means configured for attaching or coupling the movement transfer element to a rupturing movement generator device.

The rupturing tool can be coupled to a rupturing movement generator device, for example, a drilling device generating a rotary movement. The tool, particularly the movement transfer element, receives the rupturing movement from said rupturing movement generator device and in turn transfers it to the rupturing element.

In anticipation of the probable existence of many types of different rupturing movement generator devices, the option of the tool comprising one or more attachment and/or coupling means configured for attaching or coupling the movement transfer element to one or more of said devices is contemplated in this embodiment.

Advantageously, the tool has even greater versatility, where it can be coupled to any rupturing movement generator device which may be commercially available.

In a particular embodiment, the rupturing tool further comprises a support body at least partially surrounding the movement transfer element and a second attachment and/or coupling means configured for attaching or coupling the support body to a rupturing movement generator device.

In this embodiment, the tool comprises a support body, being understood to be a body which makes it easier to grip the tool, partially surrounding the movement transfer element. Optionally, this body can furthermore be attached or coupled to a rupturing movement generator device by one or more second attachment and/or coupling means.

In anticipation of the probable existence of many types of different rupturing movement generator devices, the option of the tool comprising one or more second attachment and/or coupling means configured for attaching or coupling support body to one or more of said devices is contemplated in this embodiment.

Advantageously, the tool has even greater versatility, where it can be coupled to any rupturing movement generator device which may be commercially available.

In a particular embodiment, the tool further comprises a rupturing guide configured for guiding the longitudinal body from an original position to at least one target position, wherein the rupturing guide comprises:

at least one tubular guide which in turn comprises:

a longitudinal conduit with a proximal end and a distal end; the longitudinal conduit comprising a distal appendage at the distal end; and a striking edge, a prolongation of the longitudinal conduit at the proximal end; and wherein the longitudinal conduit is configured for housing therein the longitudinal body, wherein the at least one tubular guide is oriented according to a first longitudinal guiding axis; and the striking edge is configured for receiving a striking force in the direction of the first longitudinal guiding axis; and a guide arch which in turn comprises:

a proximal arch portion which in turn comprises first coupling means configured for securely coupling and uncoupling the proximal arch portion with respect to the tubular guide in a plurality of different positions along the first longitudinal guiding axis;

a distal arch portion which in turn comprises a distal tip oriented according to a second longitudinal guiding axis;

a second coupling means configured for coupling the distal arch portion to the proximal arch portion in a plurality of different positions, such that for each of said positions the first longitudinal guiding axis and the at least one second longitudinal guiding axis form a different angle $\alpha 2$ with respect to one another; and the first longitudinal guiding axis and the at least one second longitudinal guiding axis are comprised in a second sagittal plane.

In this embodiment, the tool contemplates a rupturing guide configured for guiding the longitudinal body from an original position, that position in which the longitudinal body starts to penetrate the first segment of a bone tunnel carved with a conventional rupturing element (for example, a bit or mill), to at least one target position, particularly that in which the longitudinal body is correctly positioned so that the rupturing element moves from the first position to the second position, thereby allowing a second bone tunnel segment to be carved and a widened intraarticular outlet opening to be created.

Advantageously, the use of a rupturing guide allows increasing precision in the placement of the longitudinal body in order to complete the carving of the angled bone tunnel in the target anatomical position, as well as to improve the actual usability of the tool.

First, the rupturing guide comprises at least one tubular guide. Said guide in turn comprises the following elements:

a longitudinal conduit, preferably tubular, with a proximal end and a distal end. This conduit is sized to enable housing the longitudinal body therein. Furthermore, the distal end comprises a distal appendage (for example, a peripheral recess), being understood to be a distal end portion, a prolongation of the longitudinal conduit, the cross-section of which has a diameter smaller than the diameter of the rest of the longitudinal conduit. In a particular embodiment, this peripheral recess comprises polyhedral faces.

A striking edge, a prolongation of the longitudinal conduit at the proximal end. Striking edge shall be understood to mean a part adhered to the edge of the longitudinal conduit at its proximal end.

The guide is oriented according to the mentioned first longitudinal guiding axis, which will coincide with the first longitudinal axis according to which the main body of the longitudinal body is oriented when it is inserted in the rupturing guide. The distal appendage is sized and configured for being inserted in the first segment of the bone tunnel once carved. The diameter thereof is such that the introduction thereof in the first segment of the bone tunnel is allowed with certain tightening and the introduction of the rest of the longitudinal conduit in said bone tunnel is prevented. Preferably, the outer diameter of the appendage is substantially equal to the diameter of the first segment of the bone tunnel or slightly smaller.

To introduce said appendage in the first segment of the bone tunnel, the user must exert a specific striking force on the proximal end of the striking edge in the direction of the first longitudinal guiding axis. This force can be applied, for example, by means of a hammer.

Preferably, the proximal end of the striking edge is substantially flat.

Advantageously, the force applied on the striking edge ensures a play-free penetration of the appendage in the first segment of the bone tunnel. This allows the guide to remain in a stable position, which increases precision in the placement of the longitudinal body for carving the second segment of the bone tunnel in the target anatomical position, as well as for improving the actual usability of the tool.

Second, the rupturing guide comprises a guide arch. As such, a curved element must be understood to comprise a proximal arch portion which in turn comprises first coupling means which allow coupling said proximal arch portion securely to the tubular guide, in a plurality of different positions along the same. The guide arch further comprises a distal arch portion ending in a distal tip, and a second coupling means which allows coupling this distal arch portion to the proximal arch portion in a plurality of different positions.

The distal tip of the arch is oriented according to a second longitudinal guiding axis, which forms an angle $\alpha 2$ with the first longitudinal guiding axis. Said second longitudinal guiding axis varies according to the position in which the proximal portion and the distal portion of the guide arch have been coupled, so the angle $\alpha 2$ varies depending on said coupling. Both longitudinal guiding axes are furthermore comprised in a second sagittal plane.

Preferably, the distal tip of the distal portion is configured for being introduced in the patient's body and thereby fixing the rupturing guide. In one example, the distal portion has an elliptical, cylindrical, or annular configuration, and optionally, the distal tip is sharp.

The fixing of the distal tip in the patient's body advantageously allows achieving the more stable guide position, which allows increasing precision in the placement of the longitudinal body for carving the second segment of the bone tunnel in the target anatomical position, as well as for improving the actual usability of the tool.

Moreover, the first coupling means is configured for securely coupling and uncoupling the proximal arch portion with respect to the tubular guide in a plurality of different positions along the guide. Advantageously, this first coupling means allows the guide arch and the guide to be easily uncoupled, which makes it easier to remove the guide arch once the longitudinal body has been inserted into the guide.

The second coupling means between the proximal arch portion and the distal arch portion allows the guide to be adapted to the carving direction of the first segment of the angled bone tunnel previously decided by the user based on their preferences and on the anatomy of each patient. As mentioned above, said carving is performed with a conventional rupturing element, such as a bit.

Widening of the intraarticular outlet opening of the second segment of the bone tunnel, preferably in a funnel or fan shape, requires the user to turn the longitudinal body from left to right and/or vice versa, with the rupturing movement of the rupturing element activated when the latter is located in the second position. The first sagittal plane will therefore form a certain variable angulation with respect to the second sagittal plane. In a particular embodiment, this widening of the intraarticular outlet opening is generated in one or more planes describing curved surfaces transverse to the second sagittal plane.

In a particular embodiment, the at least one tubular guide further comprises a hole which in turn comprises a first portion and a second portion and the main body of the longitudinal body comprises at least one second projection;

the first portion of the hole is sized and configured for receiving and guiding the second projection from a proximal location to the second portion when the longitudinal body of the rupturing tool is inserted into and moves along the inside of the at least one tubular guide of the rupturing guide; and the second portion is sized and configured for abutting with the second projection when the first sagittal plane of the rupturing tool is rotated an angle $\gamma$ with respect to the second sagittal plane of the rupturing guide.

In this embodiment, the invention contemplates a hole in the guide and a projection in the main body of the longitudinal body the purpose of which is to limit the degree of rotation between the second sagittal plane and the first sagittal plane, that is, to achieve the rotation of the longitudinal body from left to right, or vice versa, up to a maximum angle when it is housed inside the rupturing guide.

The hole comprises two attached portions, the first portion being sized and configured for receiving and guiding the second projection of the main body from a proximal location, that is, from the point at which said portion receives the second projection, to a location in which the projection penetrates the second portion of the hole.

Once the projection is inside the second portion, it slides along said second portion of the hole until abutting with the ends or limits of the second portion. This sliding results from the rotation of the longitudinal body from left to right and vice versa when it is housed inside the rupturing guide. Therefore, the hole as a whole allows limiting the angle which the first sagittal plane can form with the second sagittal plane. Advantageously, it increases the usability and precision of the rupturing tool when creating a widened intraarticular outlet opening of the second segment of the bone tunnel.

In one example, the first portion of the hole is an elongated portion parallel to the second sagittal plane and the second portion of the hole is an elongated portion of a shorter length than the length of the first portion, arranged perpendicular to the second sagittal plane. Both portions form a "T"with one another.

In another example, the first portion is also elongated and arranged parallel to the second sagittal plane, whereas the second portion has a square, triangular, or funnel shape. More particularly, the second portion has a constant cross-section or a decreasing cross-section from its distal end to its proximal end. Alternatively, the second portion comprises two parts, with the first part having a constant cross-section and the second part having a decreasing cross-section (from the distal end to the proximal end of the second portion).

As a result of the second portion of the hole, the user can cause the longitudinal body to move back in the distal-proximal direction in order to widen the intraarticular outlet opening in other planes parallel to the plane in which it has been created initially. Evidently, in this new widening, the user must continue to turn the longitudinal body from left to right so that the first sagittal plane is rotated with respect to the second sagittal plane.

In an alternative embodiment, the at least one tubular guide further comprises at least one longitudinal hole and the main body of the longitudinal body comprises at least one second projection;

wherein the at least one longitudinal hole is sized and configured for receiving and guiding the at least one second projection from a proximal location to a distal location and vice versa.

In this embodiment, the tubular guide comprises at least one hole formed by a single longitudinal portion. This hole cooperates with the second projection of the main body, guiding it from a proximal location (when the rupturing guide receives the longitudinal body) to a distal location (when the second projection abuts with the distal end of the longitudinal hole).

Advantageously, the longitudinal hole allows guiding the longitudinal body of the rupturing tool while back carving the bone tunnel in at least one first back carving direction. Another advantage is that the engagement between the longitudinal hole of the tubular guide and the second projection allows controlling the relative position of both sagittal planes with respect to one another, which increases the reliability of the rupturing tool.

In a particular embodiment, the rupturing guide comprises a plurality of tubular guides, wherein:

the dimensions of the hole; and/or
the shape of the hole; and/or
the dimensions of the first portion of the hole; and/or
the shape of the first portion of the hole; and/or
the dimensions of the second portion of the hole; and/or
the shape of the second portion of the hole of each of the tubular guides is/are different from one another.

In this embodiment, it is contemplated that the tool has more than one tubular guide with holes of different dimensions and shapes. Different options for widening the intraarticular outlet opening with different sizes and depths can thus be provided, that is, the angle of rotation of the first sagittal plane with respect to the second sagittal plane can be limited more or less and the distance by which the user can cause the longitudinal body to move back can be limited more or less to generate more planes of rupture.

Advantageously, the tool is again highly versatile, allowing the dimensions of the ultimately carved bone tunnel to be adapted to the particular application, to the specific surgery type, and to patient's anatomy.

In a particular embodiment, the distal appendage comprises:

a trilobular tip; or
two tips; or
a beveled recess; or
polyhedral faces.

In this embodiment, different types of distal appendage are provided, notwithstanding the probable existence of other types which fall within the context of the invention.

In a particular embodiment, the rupturing movement is a rotational movement and the rupturing tool further comprises a movement transmission and conversion means configured for:

receiving the rotational movement from a rotational movement generator device;

converting the rotational movement into a linear and/or reciprocating movement;

transmitting the linear and/or reciprocating movement to the movement transfer element such that said movement transfer element transfers the linear and/or reciprocating movement to the rupturing element causing it to move from the first position to the at least one second position;

ceasing the linear and/or reciprocating movement when the rotational movement ceases, causing the rupturing element to move from the at least one second position to the first position.

For the rupturing element to receive the rupturing movement and the linear movement required to protrude through the opening of the distal tip and break the bone, this embodiment contemplates that the tool further comprises movement transmission and conversion means. Preferably, said movement transmission and conversion means receives the rupturing movement from a rupturing movement generator device, and transforms it into a linear movement. Additionally, the movement transmission and conversion means transmit the linear movement to the movement transfer element so that it in turn transfers same to the rupturing element, causing it to move from the first position to the at least one second position. When the linear movement ceases, that is, when the movement transmission and conversion means stop receiving rupturing movement from the generator device, the movement transmission and conversion means causes the rupturing element to move from the at least one second position to the first position, that is, to be retracted into the longitudinal body.

Advantageously, when the rupturing movement generator is activated, the tool according to this embodiment enables the rupturing element to move linearly and to perform rupturing movement at the same time, and when the rupturing movement generator is deactivated, the rupturing element is retracted and stops performing rupturing movement.

In one embodiment, the rupturing movement generator device is a drilling device and the movement transmission and conversion means comprises:

a first longitudinal rotary movement transmission element couplable to a movement transmission shaft of the drilling device, the first longitudinal element being configured for receiving the rotary movement from the drilling device and for performing said rotary movement;

a second longitudinal rotary movement transmission element, attached to the proximal part of the movement transfer element and configured for receiving a rotary movement from the first longitudinal element and for performing said rotary movement and a linear movement;

a brake actuator connected to the second longitudinal element and configured for exerting a force for retaining rotation on the second longitudinal element, a return spring configured for exerting a linear return force on the second longitudinal element; and a helical sliding coupling configured for coupling the first longitudinal element to the second longitudinal element;

wherein the helical sliding coupling in turn comprises a longitudinal coupling portion attached to the first longitudinal element comprising a first thread on its outer surface; and a longitudinal coupling conduit attached to the second longitudinal element comprising a second thread on its inner surface;

wherein the first thread of the longitudinal coupling portion and the second thread of the longitudinal coupling conduit are configured for cooperating with one another such that a linear movement of the longitudinal coupling conduit with respect to the longitudinal coupling portion occurs when the longitudinal coupling conduit performs a rotary movement and the longitudinal coupling portion rotates at a speed less than the longitudinal coupling conduit, the thread direction of the helical sliding coupling being in reverse with respect to the direction of the rotary movement of the drilling device.

Throughout this document, brake actuator shall be understood to mean a brake which applies a retaining force on the second longitudinal element such that it partially slows down the rotation of said second longitudinal element.

Throughout this document, helical sliding coupling shall be understood to mean a spindle mechanism comprising a longitudinal portion with an outer thread, for example a screw, and a longitudinal conduit with an inner thread, for example a nut. This spindle mechanism is configured for moving the conduit linearly with respect to the portion when the portion rotates and the rotation of the conduit is partially retained. In the context of the invention, "the rotation of the conduit is partially retained" should be understood to mean that the conduit rotates at a lower speed compared to the portion, due to the action of the brake actuator.

Throughout this document, return spring shall be understood to mean any helical or spiral elastic part arranged such that the force it exerts can be used to return it to its natural shape when it has been modified by pressure or elongation. In the context of the invention, the force of the return spring is used to return the second longitudinal element to a proximal stop position. Preferably, the return spring and the second longitudinal element are coaxial, with the return spring having a distal end attached to another element of the tool in a fixed position and a proximal end attached to the distal end of the second longitudinal element.

When the drilling device is inactive, that is, the movement transfer element is not receiving any rotary movement, the force of the return spring is greater than the force for retaining rotation of the brake actuator, so the second longitudinal element is located in a proximal stop position and the rupturing element is located in the first position.

When the drilling device is active, said drilling device provides a rotary movement to the first longitudinal element and this element, as a result of the sliding coupling, provides said rotary movement to the second longitudinal element. At this point, the brake actuator slows down the second longitudinal element, causing the speed of rotation thereof to decrease in relation to the speed of rotation of the first longitudinal element. At the point where the force for retaining rotation of the brake is greater than the linear return force of the spring, the components of the helical coupling, acting as a spindle screw, cause the second longitudinal element to move forward linearly with respect to the first longitudinal element. This linear forward movement occurs because the thread direction of the helical sliding coupling is in reverse with respect to the direction of the rotary movement received and transmitted by the first longitudinal element coupled to the movement transmission shaft of the drilling device.

It should be highlighted that in conventional spindles, the conduit (or nut) is fully resistant to rotation, so the conduit should not rotate at all, but only moves linearly. In contrast, the operation of the helical sliding coupling of the invention requires the rotation of the conduit to be partially retained by the brake actuator, since this rotation, which corresponds with the rupturing movement, must be transferred to the second longitudinal element, and in turn to the movement transfer element of the tool. Said second longitudinal element and movement transfer element would furthermore move linearly as a result of the action of the helical sliding coupling.

The return spring is gradually compressed during forward movement, with the force that it exerts increasing until reaching a point at which both forces of the spring and of the brake actuator are the same again. At such point, the second longitudinal element is located in a distal position and, at the same time, the rupturing element is located in the at least one second position protruding through the opening of the distal tip.

When the activity of the drilling device ceases, the force of the return spring is again greater than the force for retaining rotation of the brake actuator, given that there is no rotary movement whatsoever. In this case, the second longitudinal element returns to the proximal stop position due to the action of the linear return force of the spring and the rupturing element is retracted.

Optionally, to accelerate the process, the brake actuator comprises pads with pressure springs providing an initial rotation retaining force other than zero.

When the tool is in use, as the rupturing element gradually protrudes, the bone against which it impacts gradually exerts a retention thereon which is further transmitted to the second longitudinal element. This retaining force complements the force provided by the brake actuator, such that the more resistance the bone offers, the greater the forward movement force that must be exerted to cause the rupture.

Advantageously, this movement transmission and conversion means allows the same push-button of the drilling device, to which the rupturing tool is coupled, to simultaneously activate the rotation and the movement of the rupturing element, which increases the usability and precision of the rupturing tool.

In an alternative embodiment, the rupturing movement generator device is a drilling device and the movement transmission and conversion means comprises:

a male-female sliding coupling comprising:

a primary rotor couplable to a movement transmission shaft of the drilling device, the primary rotor being configured for receiving a rotary movement from the drilling device and for performing said rotary movement;

a secondary rotor slidingly coupled to the primary rotor at its proximal end and attached to the proximal part of the movement transfer element at its distal end; wherein the secondary rotor further comprises a groove or indentation with a sinusoidal geometry on its outer face; and wherein the secondary rotor is configured for moving linearly in both directions with respect to the primary rotor as a result of the sliding coupling;

a return spring configured for exerting a return force on the secondary rotor; and a manual activation control connected to a fixed plunger, the manual activation control being configured for causing the fixed plunger to penetrate the groove or indentation of the secondary rotor; wherein, when the secondary rotor receives the rotary movement from the primary rotor and performs said rotary movement, the activation of the control causes the fixed plunger to penetrate the groove or indentation, causing the secondary rotor to perform a linear reciprocating forward and backward movement with respect to the primary rotor, and wherein the secondary rotor transmits said linear reciprocating forward and backward movement, in combination with the rotary movement, to the movement transfer element, the movement transfer element in turn transmitting the linear reciprocating forward and backward movement, in combination with the rotary movement, to the rupturing element, and, wherein, upon removing the fixed plunger from the groove or indentation by deactivating the control, the secondary rotor performs a return movement pushed by the return spring in the distal-proximal direction.

Throughout this document, “manual activation control” shall be understood to mean an actuator which is activated and deactivated by the user at will. This manual activation control radially moves a fixed plunger from a first position, in which the plunger is far from the sinusoidal groove or indentation of the secondary rotor, to a second position, in which the fixed plunger penetrates the sinusoidal groove or indentation of the secondary rotor; and vice versa. Preferably, the mechanism of the activation control is a thrust mechanism comprising a spring. Throughout this document, “sliding coupling” shall be understood to mean a male-female type coupling comprising a primary rotor, understood to be a longitudinal male rod, and a secondary rotor, understood to be a longitudinal female conduit. This coupling between both rotors is a sliding coupling, that is, the secondary rotor can slide or move linearly in both directions with respect to the primary rotor. On one hand, the primary rotor can be coupled to the transmission shaft of a drilling device to receive a rotary movement therefrom. On the other hand, as a result of the coupling between the rotors, the primary rotor transmits said rotary movement to the secondary rotor. Lastly, the secondary rotor, which is attached to the movement transfer element at its distal end also transmits said rotary movement to the movement transfer element which will in turn transmit said movement to the rupturing element.

The secondary rotor further comprises a sinusoidal groove or indentation on its outer face which is configured for receiving and cooperating with the fixed plunger of the activation control.

When the assembly is in operation but the manual control has yet to be activated, that is, the drilling device is active, transmitting a rotary movement to the primary rotor, but the fixed plunger has not penetrated the sinusoidal groove or indentation of the secondary rotor, the rupturing element is located in the first position (inside the main body of the tool). This is due to the fact that the force of the return spring thrusts the secondary rotor to a proximal stop position, causing the rupturing element to be located in the first position inside the main body of the tool.

Once the user decides to activate the manual control, the fixed plunger penetrates the indentation or groove of the secondary rotor This penetration causes the secondary rotor to perform, together with the rotary movement, a linear reciprocating forward and backward movement with respect to the primary rotor as a result of their sliding coupling. Simultaneously, given that the secondary rotor is attached to the proximal part of the movement transfer element, it transmits not only the rotary movement but also the reciprocating movement to said movement transfer element, which in turn transmits both movements to the rupturing element. At such point, the rupturing element simultaneously describes a rotary movement about the first axis of rupture and a reciprocating movement which in turn comprises two movements which take place continuously one after another:

1. a forward movement from the first position to the second position, in which the rupturing element protrudes through the opening of the distal tip
2. a backward movement from the second position to a new position, in which the rupturing element is housed retracted in the distal tip.

The distance that would be travelled by the elements of the tool performing these forward and backward movements is given by the actual geometry of the sinusoidal groove or indentation.

When the assembly is no longer in operation, that is, when the drilling device is inactive and the manual control is deactivated, the rotors stop performing the rotary movement and the reciprocating movement. In this case, as mentioned, the force of the return spring thrusts the secondary rotor to a proximal stop position and the rupturing element returns to the first position, in which it is again located inside the main body.

Preferably, the return spring and the secondary rotor are coaxial.

In an alternative embodiment, the rupturing movement generator device is a drilling device and the movement transmission and conversion means comprises:

a male-female sliding coupling comprising:

a primary rotor couplable to a movement transmission shaft of the drilling device, the primary rotor being configured for receiving a rotary movement from the drilling device and for performing said rotary movement;

a secondary rotor slidingly coupled to the primary rotor at its proximal end; wherein the secondary rotor is configured for moving linearly in both directions with respect to the primary rotor as a result of the sliding coupling, and wherein the secondary rotor comprises a rotary pressure generator device;

a return spring configured for exerting a return force on the secondary rotor;

a fluidic Compartment Comprising a First Chamber, a Second Chamber, and a fluid; wherein the first chamber and the second chamber are in fluidic communication and the fluid is arranged inside the chambers;

the rotary pressure generator device is immersed in the fluid, arranged between the first chamber and the second chamber; and the secondary rotor is attached to the proximal part of the movement transfer element; and wherein:

when the secondary rotor receives a rotary movement from the primary rotor and performs said rotary movement, the rotary pressure generator device in turn receives said rotary movement and generates a thrust force greater than the return force of the return spring, causing the fluid to flow from the first chamber to the second chamber;

The flow of the fluid causes the secondary rotor to perform a linear movement in the proximal-distal direction;

the secondary rotor transmits the linear movement, in combination with the rotary movement, to the movement transfer element, the movement transfer element in turn transmitting the linear movement, in combination with the rotary movement, to the rupturing element, and, when the secondary rotor stops receiving the rotary movement from the primary rotor, the secondary rotor performs a linear movement in the distal-proximal direction pushed by the return spring.

Like for the preceding embodiment, in this embodiment "sliding coupling" shall be understood to mean a male-female type coupling comprising a primary rotor, understood to be a longitudinal male rod, and a secondary rotor, understood to be a longitudinal female conduit. This coupling between both rotors is a sliding coupling, that is, the secondary rotor can slide or move linearly in both directions with respect to the primary rotor.

In this embodiment, on one hand, the primary rotor can be coupled to the transmission shaft of a drilling device to receive a rotary movement therefrom. Moreover, as a result of the coupling between the rotors, the primary rotor transmits said rotary movement to the secondary rotor. The secondary rotor which in turn comprises a rotary pressure generator device transmits the rotary movement to said device. Lastly, the secondary rotor also transmits said rotary movement to the movement transfer element which will in turn transmit said movement to the rupturing element.

When the assembly is in operation, that is, the drilling device is active, transmitting a rotary movement to the primary rotor, the rotary movement is transmitted from the primary rotor to the secondary rotor. The secondary rotor in turn transmits the rotary movement to the rotary pressure generator device which is preferably a propeller or turbine. Since this device is immersed in the fluid of the fluidic compartment, it generates a thrust force greater than the thrust force of the return spring, causing the fluid to flow between both chambers of the fluidic compartment, such that the secondary rotor, comprising the rotary pressure generator device, as a result of the linear sliding coupling between both rotors, moves forward from a first proximal position to a second distal position.

In that sense, in the context of this particular embodiment, the linear sliding coupling has a dual function:

1. transmitting the rotary movement from the drilling device, through the primary rotor and the secondary rotor, to the rotary pressure generator device, and
2. allowing the linear movement of the secondary rotor with respect to the primary rotor.

In that sense, when the secondary rotor and the rotary pressure generator device move forward in the proximal-distal direction, they transmit this linear movement to the movement transfer element which in turn transmits same to the rupturing element. Therefore, the rupturing element is caused to transition from the first position, in which it is located inside the main body, to the second position, in which it protrudes partially through the opening of the distal tip. Simultaneously, the rupturing element describes a rotary movement about the first axis of rupture as a result of the transmission of this movement (drilling device—primary rotor—secondary rotor—movement transfer element—rupturing element).

When the assembly is not in operation, that is, when the drill is inactive, the force of the return spring thrusts the secondary rotor in the distal-proximal direction to a proximal stop position, in which the rupturing element is located in the first position again.

Preferably, the return spring and the secondary rotor are coaxial.

Advantageously, this movement transmission and conversion means allows the same push-button of the drilling device, to which the rupturing tool is coupled, to simultaneously activate the rotation and the movement of the rupturing element, which increases the usability and precision of the rupturing tool.

Additionally, the invention provides a rupturing system for minimally invasive surgical interventions, comprising:

- a rupturing movement generator device configured for generating and performing a rupturing movement;
- at least one rupturing tool according to the first inventive aspect; couplable to the rupturing movement generator device at least by means of the movement transfer element;

and wherein the rupturing movement generator device is further configured for transferring the rupturing movement to the movement transfer element.

In this case, the invention contemplates not only the rupturing tool, but also said tool together with a rupturing movement generator device.

In one embodiment, the rupturing tool of the system is disposable. In another alternative or additional embodiment, at least one part of the rupturing movement generator device is disposable.

The advantages set forth above for the tool can be extrapolated to this system.

Alternatively, the invention provides a rupturing system for minimally invasive surgical interventions comprising:

- a rupturing movement and linear and/or reciprocating movement generator device configured for generating and performing a rupturing movement and a linear and/or reciprocating movement;
- at least one rupturing tool according to the first inventive aspect, the rupturing tool not comprising movement transmission and conversion means and being couplable to the rupturing movement and linear and/or reciprocating movement generator device at least by means of the movement transfer element; wherein the rupturing movement and linear and/or reciprocating movement generator device is further configured for transferring the rupturing movement and the linear and/or reciprocating movement to the movement transfer element.

In this embodiment, the invention contemplates not only the rupturing tool, but also said tool together with a rupturing movement and linear and/or reciprocating movement generator device.

For the rupturing element of the tool to receive the rupturing movement and the linear movement required to protrude through the opening of the distal tip and break the bone, this system contemplates that the rupturing movement and linear and/or reciprocating movement generator provides both movements to the movement transfer element of the tool so that said tool in turn transfers same to the rupturing element causing it to move from the first position to the at least one second position. When the action of the rupturing movement and linear and/or reciprocating movement generator ceases, the movement transfer element stops receiving the rupturing movement and the linear and/or reciprocating movement, which causes the rupturing element to move from the at least one second position to the first position; i.e., to be retracted into the main body.

Advantageously, when the rupturing movement and linear and/or reciprocating movement generator is activated, this system enables the rupturing element to move linearly and perform the rupturing movement at the same time, and when the rupturing movement and linear and/or reciprocating movement generator is deactivated, the rupturing element is retracted and stops performing the rupturing movement.

Additionally, the advantages set forth above for the rupturing tool without movement transmission and conversion means can be extrapolated to this system.

In one embodiment, the rupturing tool of the system is disposable. In another alternative or additional embodiment, at least one part of the rupturing movement and linear and/or reciprocating movement generator device is disposable.

In a particular embodiment, the rupturing movement and linear and/or reciprocating movement generator device comprises mechanical and/or electronic and/or electromagnetic means.

This embodiment describes different types of means integrated in the rupturing movement and linear and/or reciprocating movement generator device, notwithstanding another type of means that falls within the context of the invention.

In this embodiment, all the rupturing systems of the invention are one-piece systems.

In a particular embodiment, all the rupturing systems of the invention further comprise adjustable control means for controlling the depth of forward movement of the rupturing element configured for adjusting the depth of forward movement of the rupturing element when it transitions from the first position to the at least one second position. Advantageously, controlling the depth of forward movement allows the user to adapt the tool to the anatomy of each patient.

In a particular example, the rupturing movement and linear movement generator device comprises electromagnetic means and the adjustable control means for controlling the depth of forward movement comprise an electronic card which can be configured for controlling the linear forward movement of the rupturing element.

All the advantages derived from the rupturing tool of the first inventive aspect are applicable to any of the rupturing systems comprising said rupturing tool.

All the features and/or the steps of the methods described in this specification (including the claims, description, and drawings) can be combined in any combination, except for combinations of such mutually exclusive features.

DESCRIPTION OF THE DRAWINGS

These and other features and advantages of the invention will be shown more clearly based on the following detailed description of a preferred embodiment, provided solely by way of illustrative and non-limiting example in reference to the attached figures.

FIGS. 1*a*-1*d:*

FIGS. 1*a*-1*d* show different views of the rupturing tool.

FIGS. 2*a*-2*d* show in detail different views of the rigidity provision element of the rupturing tool. FIG. 2*e* shows in detail different types of rigidity provision elements.

FIG. 3*a*-3*c:*

FIG. 3*a*-3*c* show a rupturing tool with a first embodiment of the movement transmission and conversion means comprising a mechanical helical sliding coupling.

FIG. 4*a*-4*g:*

FIGS. 4*a*-4*g* show a rupturing tool with a second embodiment of the movement transmission and conversion means comprising a mechanical sinusoidal coupling.

FIGS. 5*a*-5*b* show a rupturing tool with a third embodiment of the movement transmission and conversion means comprising a hydraulic coupling.

FIGS. 6*a*-6*b* show the rupturing tool according to an embodiment of the invention in which the tool comprises a rupturing guide.

FIGS. 7*a*-7*f* show in detail the rupturing guide of the rupturing tool according to an embodiment of the invention.

FIGS. 8*a*-8*b* show different views of a plurality of tubular guides of the rupturing guide of the tool according to an embodiment of the invention.

FIG. 9 shows examples of configurations of the rupturing element according to different embodiments of the invention.

FIGS. 10*a*-10*i:*

FIGS. 10*a*-10*i* show a rupturing system for surgical interventions in which the rupturing tool is coupled to an orthopedic drill.

FIGS. 11*a*-11*c* show a rupturing system for surgical interventions in which the rupturing tool is attached to an orthopedic drill.

FIG. 12*a* shows the cylindrical geometry of a tunnel back carved with a conventional rupturing tool. FIG. 12*b* shows the funnel-shaped geometry of an angled bone tunnel carved by means of the rupturing tool of the present invention. FIG. 12*c* shows different geometries of a straight bone tunnel carved by means of the rupturing tool of the present invention.

FIGS. 13*a*-13*f* illustrate the steps of a method for repairing a damaged supraspinatus tendon by means of the rupturing system of the invention.

FIGS. 14*a*-14*g* illustrate the steps of a method for restoring the anterior cruciate ligament of the right knee by means of the rupturing system of the invention.

DETAILED DESCRIPTION OF THE INVENTION

Figure 1D:
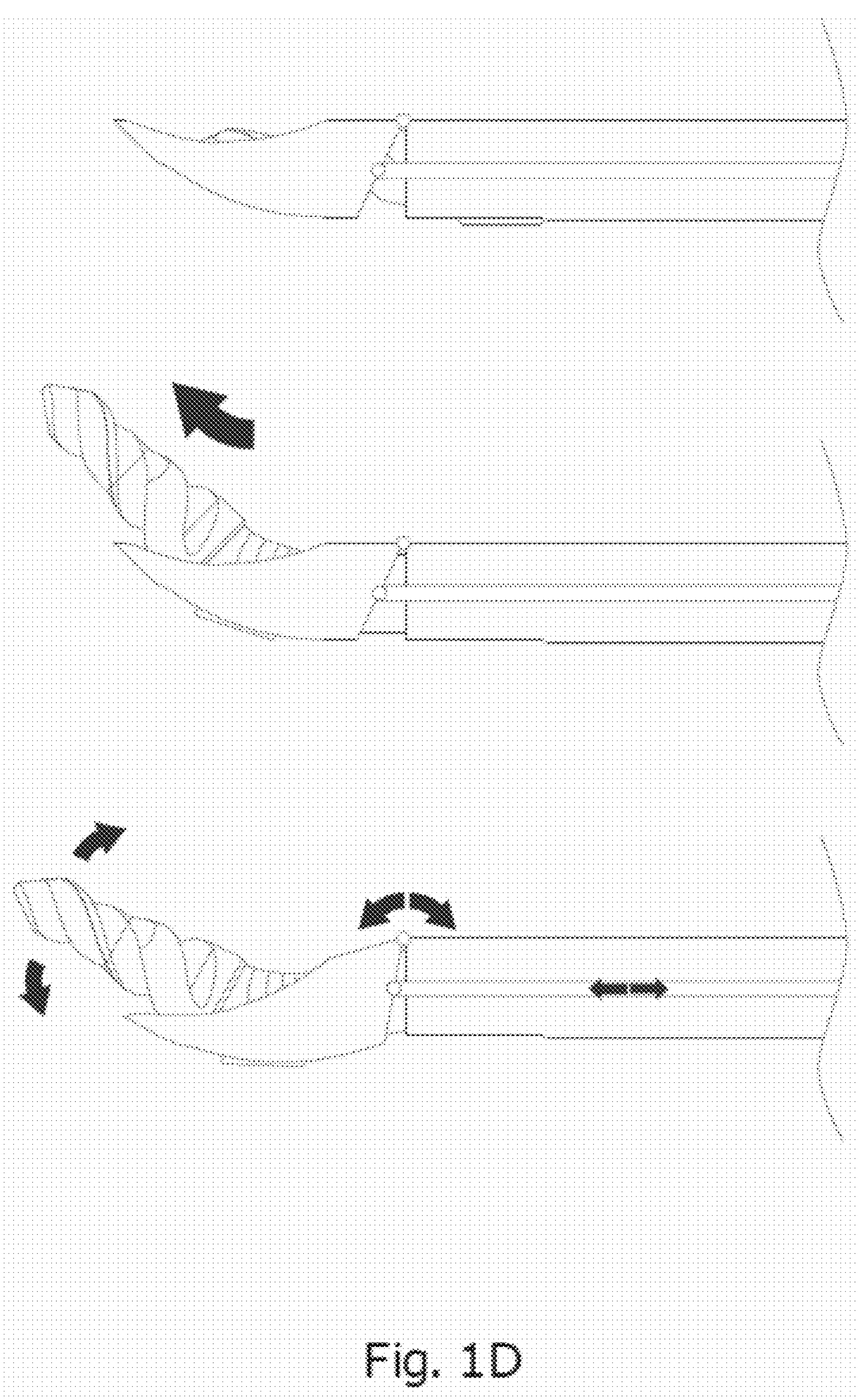

FIGS. 1*a*-1*c* show the outer perspective view of the rupturing tool with the rupturing element retracted (FIG. 1*a*), extended (FIG. 1*b*), and with all the elements in an exploded view (FIG. 1*c*).

FIG. 1*a* shows a preferred embodiment of the rupturing tool (100) for surgical interventions comprising a longitudinal body (110) which in turn comprises a main body (111) and a distal tip (112) attached to the main body (111). Preferably, the longitudinal body (110) is tubular, as shown in FIG. 1*a*. In other embodiments, the longitudinal body (110) is in the shape of a concave channel or conduit. In a particular embodiment, the main body (111) has a cylindrical configuration with a diameter of between 3 mm and 7 mm.

Additionally, the rupturing tool (100) comprises a rupturing element and a rigidity provision means, not shown in FIG. 1*a*.

FIG. 1*b* shows the same tool, but it can be seen therein that the main body (111) is oriented according to a first longitudinal axis (101) and the opening (115) of the distal tip (112) is oriented according to a second longitudinal axis (102).

Additionally, from this figure it is derived that the first longitudinal axis (101) and the at least one second longitudinal axis (102) form with respect to one another an angle $\alpha$ (which can be equal to or greater than zero degrees), and that the first longitudinal axis (101) and the second longitudinal axis (102) are comprised in a first sagittal plane (103).

In a particular embodiment, the angle $\alpha$ between the first longitudinal axis (101) and the second longitudinal axis (102) is an angle of between 25° and 65°. In a more particular embodiment, the angle $\alpha$ is 45°.

In this embodiment of FIG. 1*b*, the distal tip (112) is securely attached to the main body (111) as a prolongation thereof, that is, the longitudinal body (110) is one-piece.

In these figures, the distal tip (112) forms of a curved ramp with the main body (111). In other embodiments, the ramp is straight.

Additionally, part of the rupturing assembly (120) can be seen in FIG. 1*b* protruding through the opening (115) of the distal tip (112).

The rupturing assembly (120) of the rupturing tool (100) comprises:

- a rupturing element (121) comprising a first axis of rupture (121.1) and configured for receiving and performing a rupturing movement about the first axis of rupture (121.1) and for receiving and performing a linear movement, moving along the longitudinal body (110) from a first position to at least one second position, and vice versa, wherein:
  - if the rupturing element (121) is located in the first position, the rupturing element (121) is oriented according to the first longitudinal axis (101) inside the main body (111); and
  - if the rupturing element (121) is located in the second position, the rupturing element (121) is oriented according to the at least one second longitudinal axis (102) protruding at least partially through the opening (115) of the distal tip (112); and
- a movement transfer element (122), comprising a proximal part (122.1), a flexible or articulated distal part (122.2), and a second axis of rupture (122.3), the movement transfer element (122) being securely attached to the rupturing element (121) by the flexible or articulated distal part (122.2) and being configured for:
  - receiving and performing a rupturing movement about the second axis of rupture (122.3) and for transferring the rupturing movement to the rupturing element (121); and
  - receiving and performing a linear movement, moving along the longitudinal body (110); and for transferring the linear movement to the rupturing element (121).

FIG. 1*a* shows the rupturing element (121) located in the first position, that is, the rupturing element (121) is located inside the main body (111) and oriented according to the first longitudinal axis (101).

FIG. 1*b* shows the rupturing element (121) located in the second position, that is, the rupturing element (121) is oriented according to the second longitudinal axis (102) protruding at least partially through the distal tip (112) through the opening (115) of said tip (112).

In a particular embodiment, the rupturing element (121) has a length of between 10 mm and 25 mm.

FIG. 1*c* shows an exploded view of the same tool (100) as that illustrated in FIGS. 1*a* and 1*b*.

The movement transfer element (122) which, besides the second axis of rupture (122.3), comprises a proximal part (122.1) and a flexible or articulated distal part (122.2) can be seen in detail in this FIG. 1*c*.

As mentioned above, the movement transfer element (122) is securely attached to the rupturing element (121). Said attachment is established by the flexible or articulated distal part (122.2) of the movement transfer element (122).

FIG. 1*c* furthermore shows the rigidity provision means (130), which is configured for providing the flexible or articulated distal part (122.2) of the movement transfer element (122) with rigidity in every plane other than the first sagittal plane (103) when the rupturing element (121) is located in the at least one second position (shown in FIG. 1*b*).

In a preferred embodiment, the rupturing movement is a rotary movement. In other embodiments, the movement is a vibratory or reciprocating movement.

In these figures, the rupturing tool (100) further comprises at least one first attachment and/or coupling means (140) configured for attaching or coupling the movement transfer element (122) to a rupturing movement generator device (200, 200') which is not shown. Additionally, the tool (100) comprises a support body (160.1, 170.1, 180.1) partially surrounding the movement transfer element (122) and second attachment and/or coupling means (150) configured for attaching or coupling the support body (160.1, 170.1, 180.1) to the rupturing movement generator device (200, 200').

In a particular embodiment in which the rupturing movement is a rotational movement, the rupturing tool (100) further comprises a movement transmission and conversion means (not shown in FIGS. 1*a*-1*c*). This means is configured for:

- receiving the rotational movement from a rotational movement generator device, for example a drill;
- converting the rotational movement into a linear and/or reciprocating movement;
- transmitting the linear and/or reciprocating movement to the movement transfer element (122) such that said movement transfer element (122) transfers the linear and/or reciprocating movement to the rupturing element (121) causing it to move from the first position to the at least one second position;
- the linear and/or reciprocating movement ceasing when the rotational movement ceases, causing the rupturing element (121) to move from the at least one second position to the first position.

Preferably, the movement transmission and conversion means is integrated inside the support body (160.1, 170.1, 180.1).

A reference ring (116) surrounding the longitudinal body (110), where said ring can move along the body (110), can furthermore be seen in these FIGS. 1*a*-1*c*. This ring (118), which is completely optional, is used as a reference for the user who is using the rupturing tool (100), in particular, it is used to inform the user of the depth of back milling.

FIG. 1*d* shows an alternative embodiment to that of FIGS. 1*a*-1*d*, in which the distal tip (112) is attached to the main body (111) by means of an attachment element configured for positioning said distal tip (112) in a plurality of angular positions such that, for each of said plurality of angular positions, a second different longitudinal axis (102) is formed, each of which forms a different angle α with the first longitudinal axis (101). In this case, the distal tip (112) can be positioned in a plurality of different angular positions and the rupturing element (121), in the second position, will be oriented according to one of said plurality of different angular positions.

FIGS. 2*a*-2*d* show in detail different views of the rigidity provision element (130).

Figures 2A, 2B, 2C, 2D:
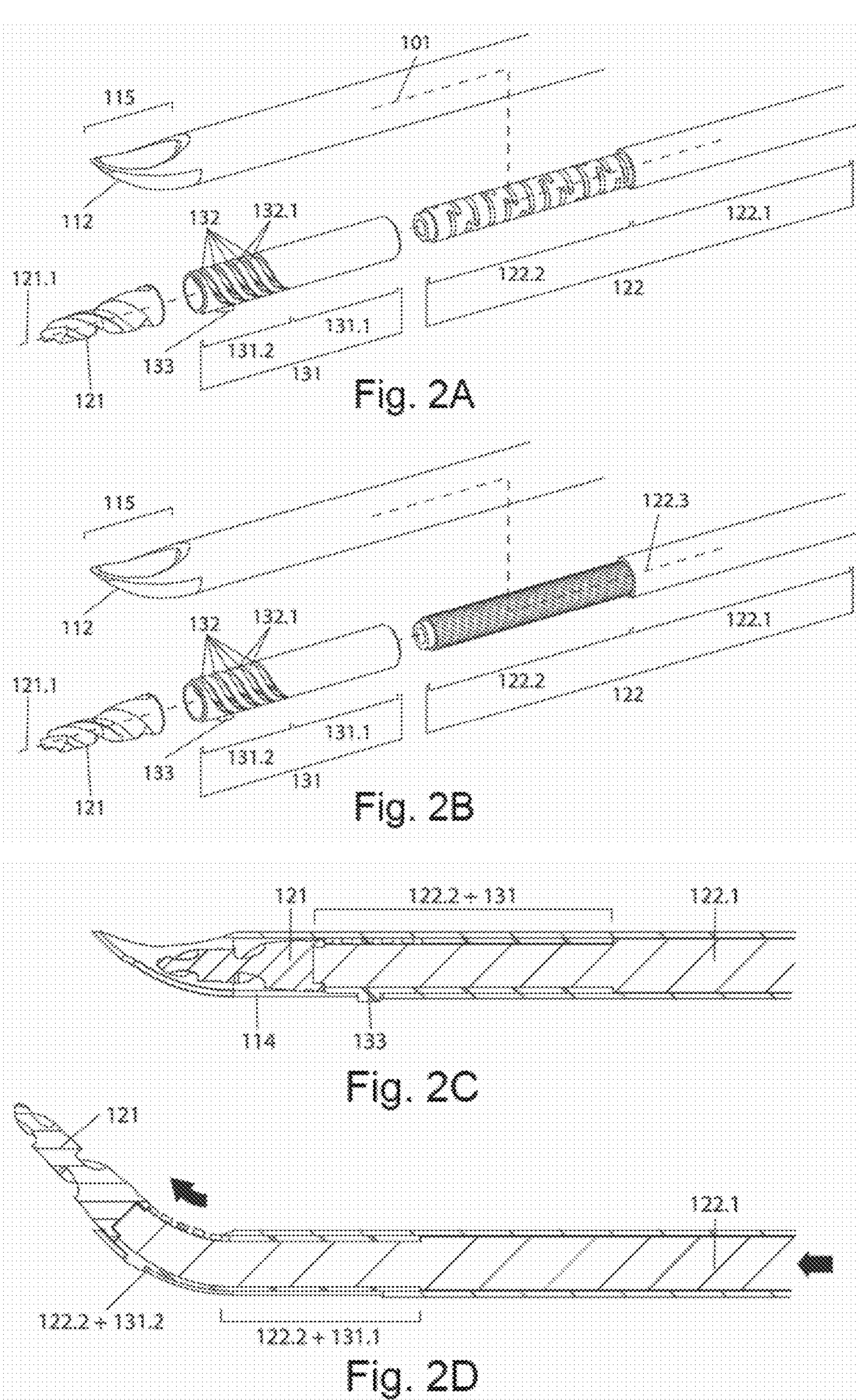
FIGS. 2*a*-2*e:*

FIGS. 2*a* and 2*b* show the exploded perspective views of the rigidity provision element (130) together with other parts of the tool (100) with which it interacts.

Said element (130) comprises a tubulated element (131) which in turn comprises a proximal portion (131.1) and a distal portion (131.2).

This tubulated element (131) surrounds the flexible or articulated distal part (122.2) of the movement transfer element (122), housing said flexible or articulated part (122.2) therein. Furthermore, the tubulated element (131) has dimensions suitable for being housed inside the longitudinal body (110) and can move along the inside of said body. This movement is possible because the tubulated element houses the movement transfer element (122), that is, when the movement transfer element (122) moves linearly to cause the rupturing element (121) to protrude through the opening of the distal tip (112), the tubulated element (131) also moves integrally. Additionally, the movement transfer element (122) performs a rupturing movement about the second axis of rupture (122.3) and the rupturing element (121) also performs said rupturing movement about the first axis of rupture (121.1) without the tubulated element (131) interfering in said rupturing movements.

The difference between FIGS. 2*a* and 2*b* lies in the different configurations of the flexible or articulated distal part (122.2) of the movement transfer element (122). In FIG. 2*a*, said flexible or articulated distal part (122.2) has a configuration comprising a grooved surface, whereas in FIG. 2*b*, the flexible or articulated distal part (122.2) has a braided configuration. In other embodiments, other configurations of the flexible or articulated distal part (122.2) are feasible in the context of the invention.

Additionally, the tubulated element (131) comprises at least one elongated notch (132) arranged on the upper part of the distal portion (131.2) forming an angle β greater than 0 degrees and less than or equal to 90 degrees with respect to the first sagittal plane (103). Said angle β can be the same for all the notches (132), in the case where there are more than one, or can be different.

Each of these notches (132) separates the upper part of the distal portion (131.2) into two different segments (132.1), spaced apart by a specific separation, when the rupturing element is located in the first position. The separation defined by each notch (132) can be the same or different, provided that the total sum of the separations of all the notches (132) is substantially zero when the distal portion (131.2) of the tubulated element (131) is located in the distal tip (112) of the tool (that is, when the rupturing element (121) is located in the second position).

In one example, the notches (132) have a trapezoidal geometry, and/or a winding geometry, and/or a sinusoidal geometry, and/or any other geometry, provided that they are arranged forming an angle β (or several angles β) with respect to the first sagittal plane (103).

In another example, the tubulated element (131) comprises a modular system consisting of portions that are coupled to one another configuring a winding body in a single sagittal plane, such that the total sum of the separations between portions is substantially zero when the distal portion (131.2) of the tubulated element (131) is located in the distal tip (112) of the tool.

In another example, the tubulated element (131) comprises a tube made of superelastic nitinol, with or without notches, and an outer polymer layer.

FIGS. 2*c* and 2*d* show in detail the location of the rigidity provision element (130) when the rupturing element (121) is located in the first position or in the second position, respectively.

In FIG. 2*c*, that is, when the rupturing element (121) is in the first position, the two portions (131.1, 131.2) of the tubulated element (131) are oriented according to the first longitudinal axis (101), since they are positioned inside the main body (110). In FIG. 2*d*, that is, when the rupturing assembly (120) and the rigidity provision element (130) have been moved, the rupturing element (121) is located in the second position and only the proximal portion (131.1) of the tubulated element (131) remains oriented according to the first longitudinal axis (101). In other words, said proximal portion (131.1) is still located inside the main body (110) whereas the flexible or articulated distal portion (131.2) of the tubulated element (131) is oriented according to the second longitudinal axis (102) or one of the second longitudinal axes (102). In this second case, the flexible or articulated distal portion (131.2) is positioned in the distal tip (112) of the tool (100), acquiring a curved shape.

This means that, in the first case, the notches (132) remain open, whereas in the second case, the notches (132) are virtually closed, that is, the walls of consecutive segments (132.1) contact one another due to the actual curved position of the tubulated element (131). Therefore, the tubulated element (131) allows providing rigidity to the flexible or articulated distal part (122.2) of the movement transfer element (122) in all the planes except in the first sagittal plane (103), along which said flexible or articulated part (122.2) has acquired a curved shape. This same rigidity is transferred to the rupturing element (121) when it is located in the at least one second position.

Additionally, in FIGS. 2*c* and 2*d* it can be seen that the longitudinal body (110) comprises a distal longitudinal groove (114) and the tubulated element (131) comprises a first projection (133). In other examples, more than one distal longitudinal groove (114) and more than one tubulated element (131) or more than one first projection (133) is possible.

The distal longitudinal groove (114) is sized for receiving the first projection (133) and configured for cooperating with said first projection (133), guiding it in the direction of the sagittal plane (103) shown with an arrow in FIG. 2*d*. The movement of the tubulated element (131) occurs simultaneously with the linear movement of the rupturing element (121) when it moves from the first position to the second position, and vice versa.

At the same time, the first projection (133) is sized for penetrating the distal longitudinal groove (114) and is configured for cooperating with said distal longitudinal groove (114), moving along said groove (114) when the rupturing element (121) moves from the first position to the second position, and vice versa. The distal edge of the distal longitudinal groove (113) acts as a stop for the first projection (133) when the rupturing element (121) is located in the second position, such that in this at least one second position the separations between segments (132.1) of the tubulated body (131) is substantially zero, the rupturing element (121) thereby acquiring rigidity in this at least one second position.

Figure 2E:
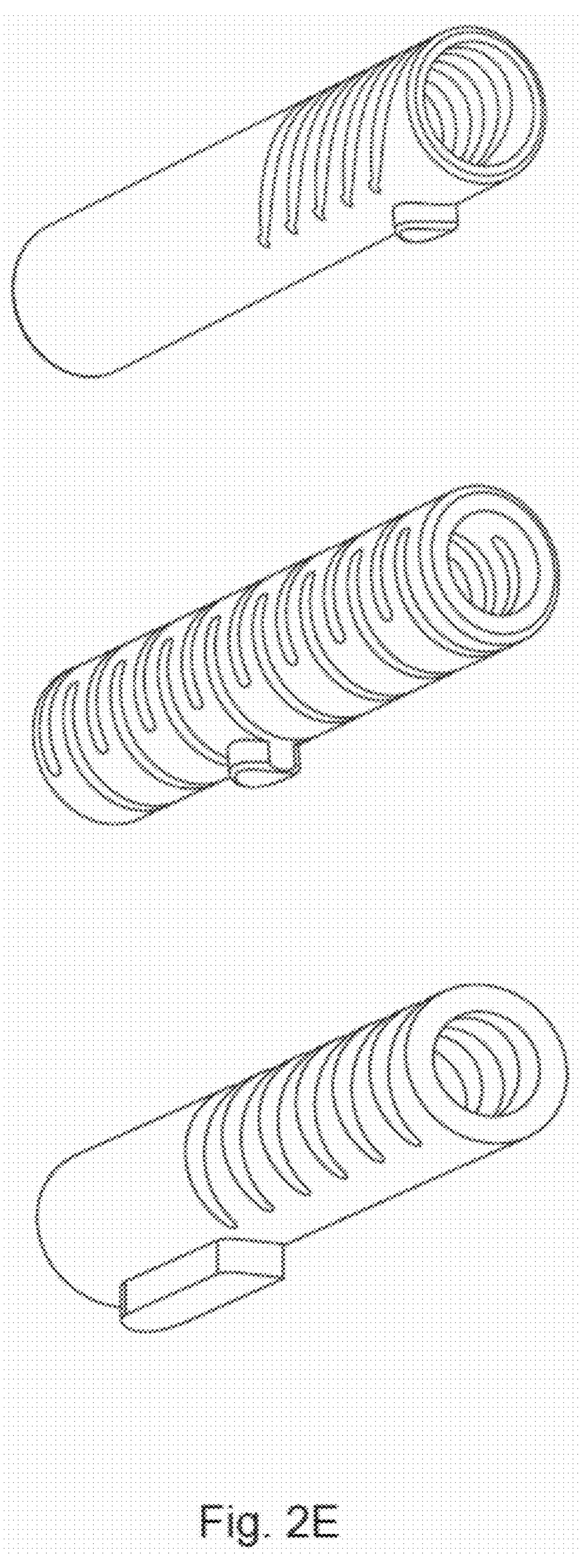

FIG. 2*e* shows in detail different types of rigidity provision elements (130).

FIGS. 3*a*-3*c* show an embodiment of the rupturing tool (100) in which said tool (100) comprises movement transmission and conversion means (160). For this embodiment, the rupturing movement generator device (200, 200') is a rotary movement generator device (200, 200'), preferably a drilling device.

The movement transmission and conversion means (160) of This embodiment comprises:

- a first longitudinal rotary movement transmission element (161) couplable to a movement transmission shaft of the drilling device (200, 200'), the first longitudinal element (161) being configured for receiving the rotary movement from the drilling device (200, 200') and for performing said rotary movement;
- a second longitudinal rotary movement transmission element (162), attached to the proximal part (122.3) of the movement transfer element (122) and configured for receiving a rotary movement from the first longitudinal element (161) and for performing said rotary movement and a linear movement;
- a brake actuator (163) connected to the second longitudinal element (162) and configured for exerting a force for retaining rotation on the second longitudinal element (162),
- a return spring (164) configured for exerting a linear return force on the second longitudinal element (162); and
- a helical sliding coupling (165) configured for coupling the first longitudinal element (161) to the second longitudinal element (162);

wherein the helical sliding coupling (165) in turn comprises a longitudinal coupling portion (161.1) attached to the first longitudinal element (161) comprising a first thread (161.2) on its outer surface; and a longitudinal coupling conduit (162.1) attached to the second longitudinal element (162) comprising a second thread (162.2) on its inner surface;

wherein the first thread (161.2) of the longitudinal coupling portion (161.1) and the second thread (162.2) of the longitudinal coupling conduit (162.1) are configured for cooperating with one another such that a linear movement of the longitudinal coupling conduit (162.1) with respect to the longitudinal coupling portion (161.1) occurs when the longitudinal coupling conduit (162.1) performs a rotary movement and the longitudinal coupling portion (161.1) rotates at a speed less than the longitudinal coupling conduit (162.1), the thread direction of the helical sliding coupling (165) being in reverse with respect to the direction of the rotary movement of the drilling device.

FIG. 3*a* shows a view of the assembly of said movement transmission and conversion means (160) integrated in the support body (160.1). The shape and dimensions of said support body (160.1) may vary. FIGS. 3*b* and 3*c* show side sectional views of the support body (160.1) so as to enable observing the operation of the movement transmission and conversion means (160) of this embodiment. In particular, FIG. 3*b* shows the situation in which the drilling device (not shown) is not in operation and the second longitudinal element (162) is in a first position. FIG. 3*c* shows the situation in which the drilling device (not shown) is in operation and the second longitudinal element (162) is in a second position, linearly moved with respect to the first position.

In more detail, FIG. 3*a* shows the situation in which the drilling device is inactive, that is, when the movement transfer element (122) is not receiving any rotary movement. In this case, the force of the return spring (164) is greater than the force for retaining rotation of the brake actuator (163), so the second longitudinal element (162) is located in a proximal stop position and the rupturing element (not shown in this figure) is located in the first position.

FIG. 3*b* shows the situation in which the drilling device (200) is active. Said drilling device provides a rotary movement to the first longitudinal element (161) and this element, as a result of the helical sliding coupling (165), provides said rotary movement to the second longitudinal element (162). At this point, the brake actuator (163) increases the force for retaining rotation it transmits to the second longitudinal element (162), causing the speed of rotation of the second longitudinal element (162) to decrease in relation to the speed of rotation of the first longitudinal element (161). At the point where the force for retaining rotation of the brake (163) is greater than the linear return force of the spring (164), the components of the helical sliding coupling (165), acting as a spindle screw, cause the second longitudinal element (162) to move linearly forward with respect to the first longitudinal element (161). This linear forward movement occurs because the thread direction of the helical sliding coupling (165) is in reverse with respect to the direction of the rotary movement received and transmitted by the first longitudinal element (161) coupled to the movement transmission shaft of the drilling device.

The return spring (164) is gradually compressed during forward movement, with the force that it exerts increasing until reaching a point at which both forces of the spring (164) and of the brake actuator (163) are the same again. At such point, the second longitudinal element (162) is located in a distal position, and, at the same time, the rupturing element (121) is located in the at least one second position protruding through the opening (115) of the distal tip (112).

When the activity of the drilling device ceases, the force of the return spring (164) is again greater than the force for retaining rotation of the brake actuator (163), given that there is no rotary movement whatsoever. In this case, the second longitudinal element (162) returns to the proximal stop position as a result of the action of the linear return force of the spring (164) and the rupturing element (121) is retracted, returning to the situation shown in FIG. 3.

Optionally, to accelerate the process, the brake actuator (163) comprises pads with pressure springs providing an initial rotation retaining force other than zero. FIGS. 4*a*-4*g* show an embodiment of the rupturing tool (100) in which said tool (100) comprises manually activated movement transmission and conversion means (170). For this embodiment, the rupturing movement generator device (not shown) is a rotary movement generator device, preferably a drilling device.

The movement transmission and conversion means (170) of this embodiment comprises:

- a male-female sliding coupling (173) comprising:
  - a primary rotor (171) couplable to a movement transmission shaft of the drilling device (200, 200'), the primary rotor (171) being configured for receiving a rotary movement from the drilling device (200, 200') and for performing said rotary movement;
  - a secondary rotor (172) slidingly coupled to the primary rotor (171) at its proximal end and attached to the proximal part (122.1) of the movement transfer element (122) at its distal end; wherein the secondary rotor (172) further comprises a groove or indentation (172.1) with a sinusoidal geometry on its outer face; and wherein the secondary rotor (172) is configured for moving linearly in both directions with respect to the primary rotor (171) as a result of the sliding coupling;

a return spring (174) configured for exerting a return force on the secondary rotor (172); and a manual activation control (175) connected to a fixed plunger (176), the manual activation control (175) being configured for causing the fixed plunger (176) to penetrate the groove or indentation (172.1) of the secondary rotor (172);

wherein, when the secondary rotor (172) receives the rotary movement from the primary rotor (171) and performs said rotary movement, the activation of the control (175) causes the fixed plunger (176) to penetrate the groove or indentation (172.1), causing the secondary rotor (172) to perform a linear reciprocating forward and backward movement with respect to the primary rotor (171), and wherein the secondary rotor (172) transmits said linear reciprocating forward and backward movement, in combination with the rotary movement, to the movement transfer element (122), the movement transfer element (122) in turn transmitting the linear reciprocating forward and backward movement, in combination with the rotary movement, to the rupturing element (121), and, wherein, upon removing the fixed plunger (176) from the groove or indentation (172.1) by the deactivation of the control (175), the secondary rotor (172) performs a return movement pushed by the return spring (174) in the distal-proximal direction.

Figure 4A:
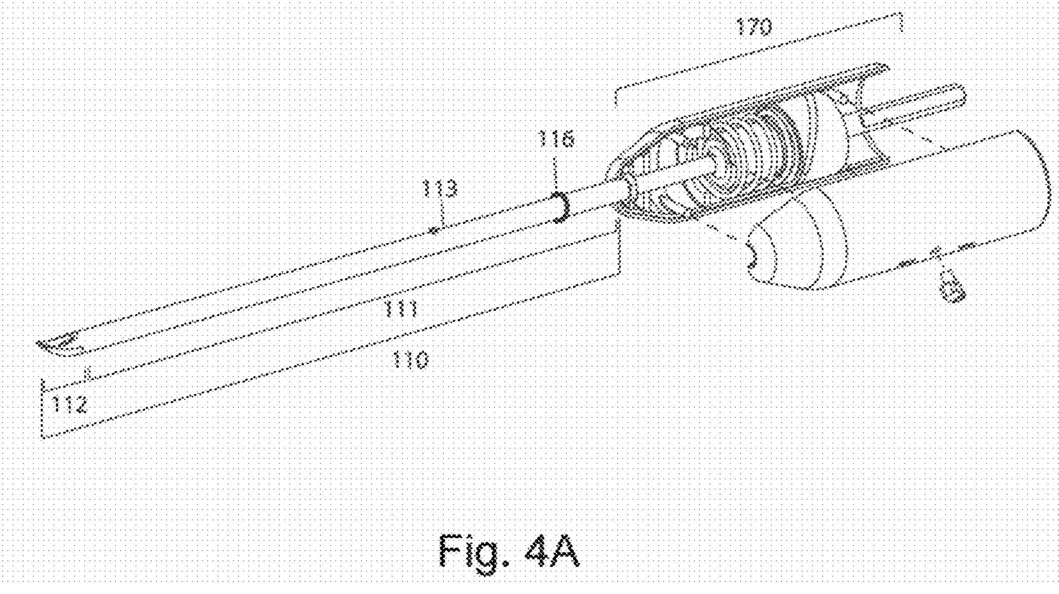
Figure 4B:
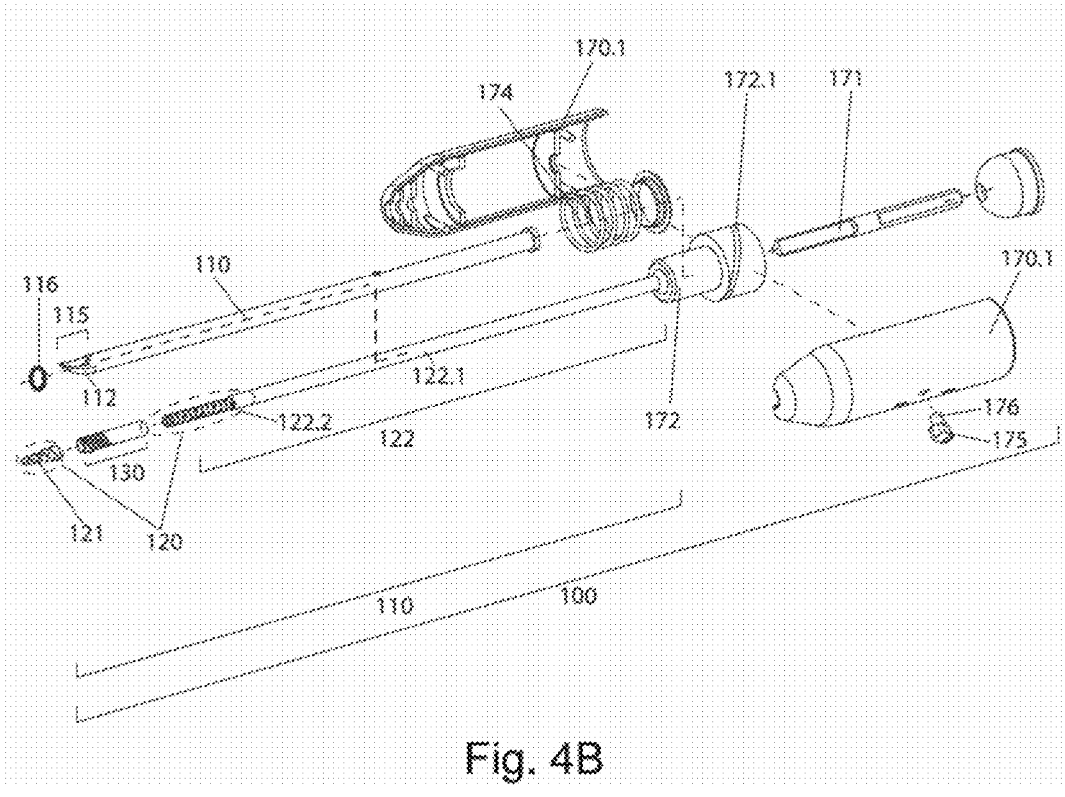
Figures 4C, 4D:
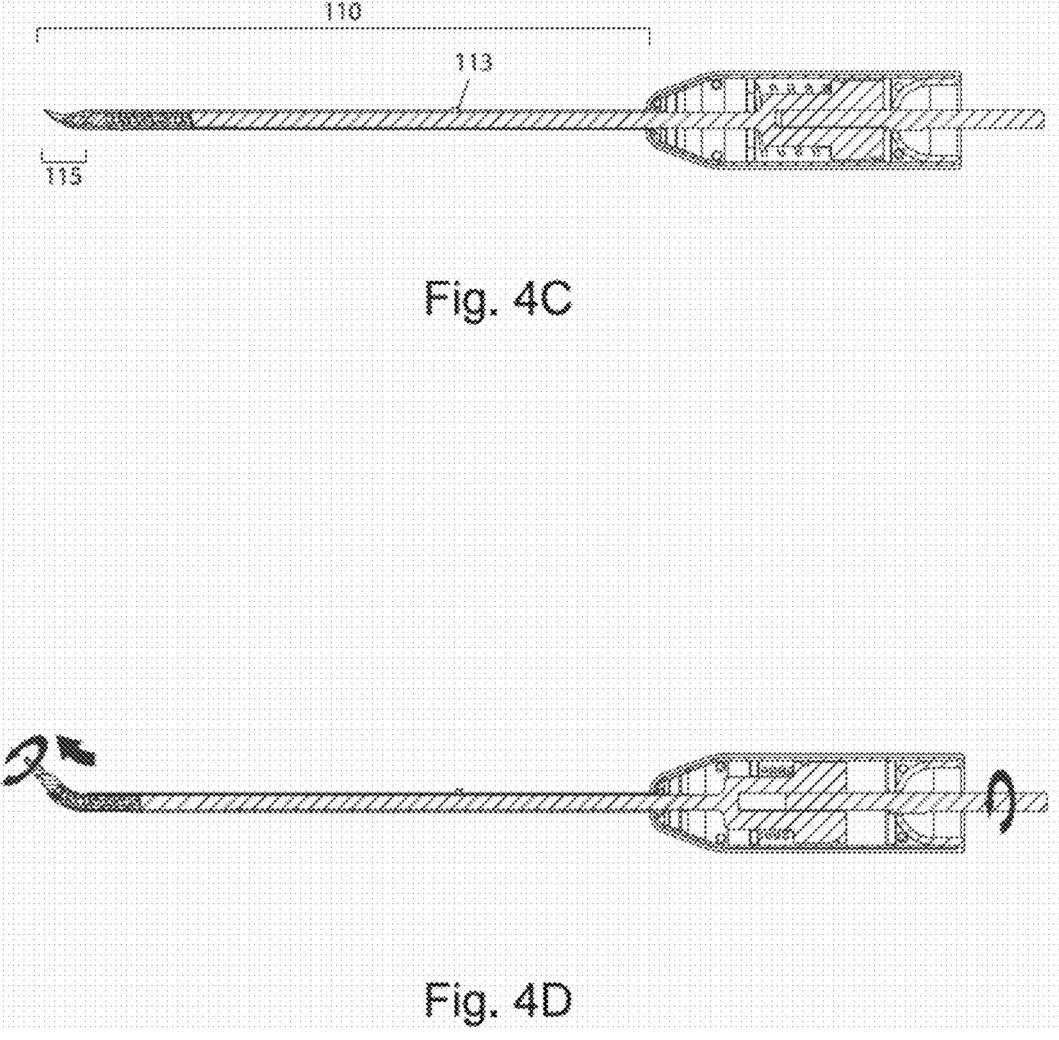

FIG. 4*a* shows said movement transmission and conversion means (170) integrated in the support body (170.1). The shape and dimensions of this support body (170.1) may vary. FIG. 4*b* shows an exploded view of the tool of this embodiment. FIGS. 4*c*-4*d* show side sectional views of the rupturing tool (100) of this embodiment and FIGS. 4*e*-4*g* show side sectional views of the support body (170.1) of said tool (100) to enable observing the operation of the movement transmission and conversion means (170) of this embodiment.

In this embodiment, when the assembly is in operation but the manual control (175) has yet to be activated, that is, the drilling device (200, 200') is active, transmitting a rotary movement to the primary rotor (171), but the fixed plunger (176) has not penetrated the sinusoidal groove or indentation (172.1) of the secondary rotor (172), the rupturing element (121) is located in the first position (inside the main body (111) of the tool (100)). This is because the force of the return spring (174) thrusts the secondary rotor (172) to a proximal stop position, causing the rupturing element (121) to be located in the first position inside the main body (111) of the tool (100).

Once the user decides to activate the manual control (175), the fixed plunger (176) penetrates the indentation or groove (172.1) of the secondary rotor (172). This penetration causes the secondary rotor (172) to perform, together with the rotary movement, a linear reciprocating forward and backward movement with respect to the primary rotor (171) as a result of their sliding coupling (173). Simultaneously, given that the secondary rotor (172) is attached to the proximal part (122.1) of the movement transfer element (122), it transmits not only the rotary movement but also the reciprocating movement to said movement transfer element (122), which in turn transmits both movements to the rupturing element (121). At such point, the rupturing element (121) simultaneously describes a rotary movement about the first axis of rupture and a reciprocating movement which in turn comprises two movements which take place continuously one after another:

1. a forward movement from the first position to the second position, in which the rupturing element (121) protrudes through the opening (115) of the distal tip (112), and
2. a backward movement from the second position to a new position, in which the rupturing element (121) is housed retracted in the distal tip (115).

The distance that would be travelled by the elements of the tool (100) performing these forward and backward movements is given by the actual geometry of the sinusoidal groove or indentation (172.1).

When the assembly is no longer in operation, that is, when the drilling device (200, 200') is inactive and the manual control (175) is deactivated, the rotors (171, 172) stop performing the rotary movement and the reciprocating movement. In this case, as mentioned, the force of the return spring (174) thrusts the secondary rotor (172) to a proximal stop position and the rupturing element (121) returns to the first position, in which it is again located inside the main body (111).

In more detail, FIG. 4*c* shows the situation in which the drilling device (not shown) is inactive, that is, when the movement transfer element (122) is not receiving any rotary movement. In this case, the force of the return spring (174) thrusts the secondary rotor (172) to a proximal stop position and the rupturing element (121) is in the first position.

FIG. 4*d* shows the situation in which the drilling device (not shown) is active, and the manual activation control (175) is pressed. Said drilling device provides a rotary movement to the primary rotor (171) and said rotor provides said rotary movement to the secondary rotor (172). Additionally, the fixed plunger (176) cooperates with the sinusoidal groove or indentation (172.1) such that the secondary rotor (172) performs a linear reciprocating forward and backward movement which it transmits, together with the rotary movement, to the movement transfer element (122), which in turn transmits both movements to the rupturing element (121).

Upon releasing the fixed plunger (176) by means of the manual control, the secondary rotor (172), pushed by the return spring (174), performs a return movement to the starting position and the rupturing element (121) is retracted, returning to the situation shown in FIG. 4*c*.

Figures 5A, 5B:
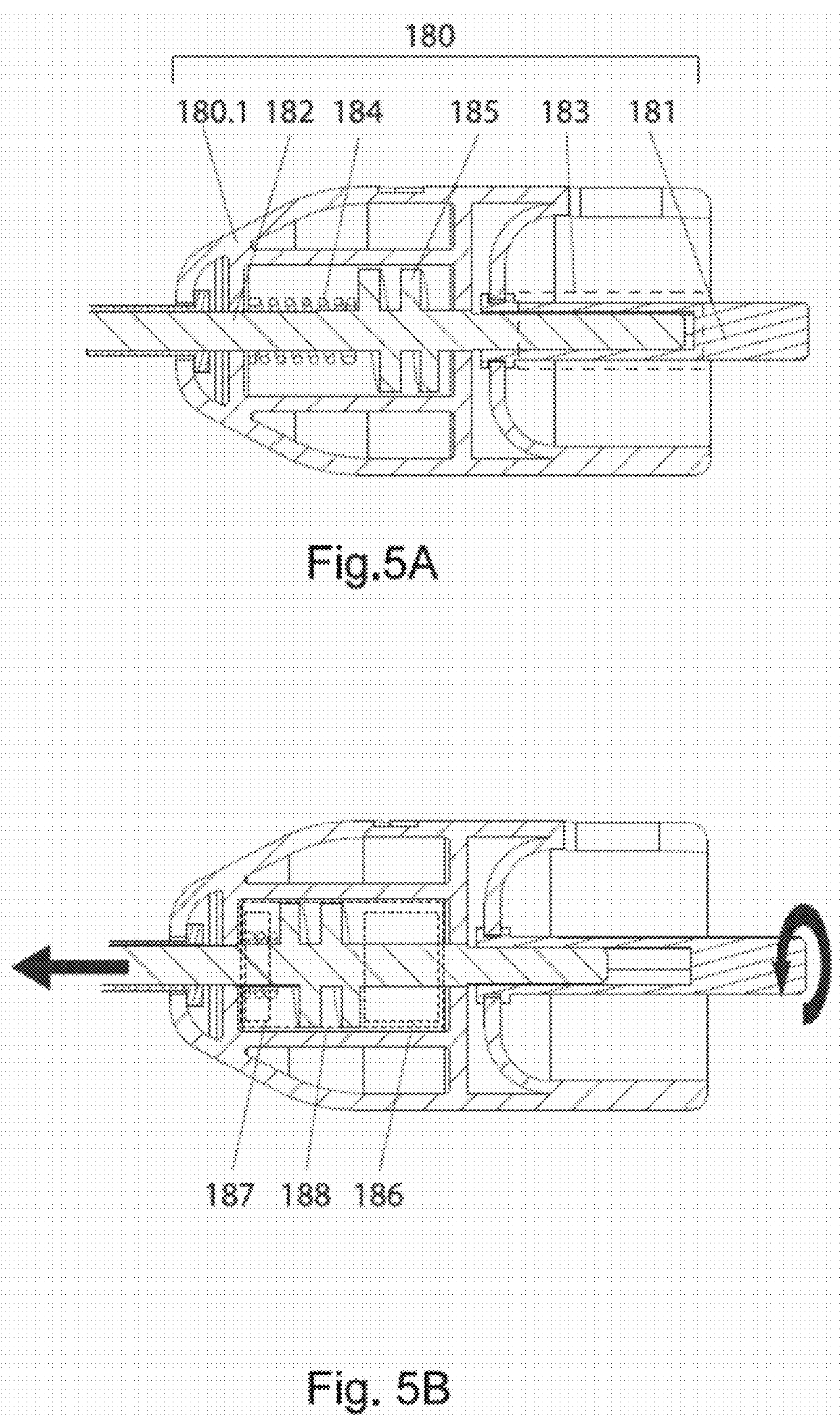
FIGS. 5*a*-5*b:*

FIGS. 5*a* and 5*b* show another embodiment of the invention in which the movement transmission and conversion means (180) comprises an automatically activated hydraulic system. For this embodiment, the rupturing movement generator device (not shown) is a rotary movement generator device, preferably drilling device.

The movement transmission and conversion means (180) of this embodiment comprises:

a male-female sliding coupling (183) comprising:

a primary rotor (181) couplable to a movement transmission shaft of the drilling device (200, 200'), the primary rotor (181) being configured for receiving a rotary movement from the drilling device (200, 200') and for performing said rotary movement;

a secondary rotor (182) slidingly coupled to the primary rotor (181) at its proximal end; wherein the secondary rotor (182) is configured for moving linearly in both directions with respect to the primary rotor (181) as a result of the sliding coupling, and wherein the secondary rotor (182) comprises a rotary pressure generator device (185);

a return spring (184) configured for exerting a return force on the secondary rotor (182);

a fluidic compartment comprising a first chamber (186), a second chamber (187), and a fluid (188); wherein the first chamber (186) and second chamber (187) are in fluidic communication and the fluid (188) is arranged inside the chambers (186, 187);

the rotary pressure generator device (185) is immersed in the fluid (188), arranged between the first chamber (186) and second chamber (187); and the secondary rotor (182) is attached to the proximal part (122.1) of the movement transfer element (122); and wherein:

when the secondary rotor (182) receives a rotary movement from the primary rotor (181) and performs said rotary movement, the rotary pressure generator device (185) in turn receives said rotary movement and generates a thrust force greater than the return force of the return spring (184), causing the fluid (188) to flow from the first chamber (186) to the second chamber (187);

the flow of the fluid (188) causes the secondary rotor (182) to perform a linear movement in the proximal-distal direction;

the secondary rotor (182) transmits the linear movement, in combination with the rotary movement, to the movement transfer element (122), the movement transfer element (122) in turn transmitting the linear movement, in combination with the rotary movement, to the rupturing element (121), and, when the secondary rotor (182) stops receiving the rotary movement from the primary rotor (181), the secondary rotor (182) performs a linear movement in the distal-proximal direction pushed by the return spring (184).

FIG. 5*a* shows this movement transmission and conversion means (180). FIG. 5*b* shows by means of arrows the rotary and linear movements received and performed by the movement transmission and conversion means (180).

When the assembly is in operation, that is, the drilling device (200, 200') is active, transmitting a rotary movement to the primary rotor (181), the rotary movement is transmitted from the primary rotor (181) to the secondary rotor (182). The secondary rotor (182) in turn transmits the rotary movement to the rotary pressure generator device (185) which is preferably a propeller or turbine. Since this device (185) is immersed in the fluid (188) of the fluidic compartment, it generates a thrust force greater than the thrust force of the return spring (184), causing the fluid to flow between both chambers (186, 187) of the fluidic compartment, such that the secondary rotor (182), comprising the rotary pressure generator device (185), as a result of the linear sliding coupling (183) between both rotors (181, 182), moves forward from a first proximal position to a second distal position.

In that sense, in the context of this particular embodiment, the linear sliding coupling (183) has a doble function:

1. transmitting the rotary movement from the drilling device (200, 200'), through the primary rotor (181) and the secondary rotor (182), to the rotary pressure generator device (185), and
2. allowing the linear movement of the secondary rotor (182) with respect to the primary rotor (181).

In that sense, when the secondary rotor (182) and the rotary pressure generator device (185) move forward in the proximal-distal direction, they transmit this linear movement to the movement transfer element (122) which in turn transfers same to the rupturing element (121). Therefore, the rupturing element (121) is caused to transition from the first position, in which it is located inside the main body (111), to the second position, in which it partially protrudes through the opening (115) of the distal tip (112). Simultaneously, the rupturing element (121) describes a rotary movement about the first axis of rupture because of the transmission of this movement (drilling device (200, 200')—primary rotor (181)—secondary rotor (182)—movement transfer element (122)—rupturing element (121)).

When the assembly is not in operation, that is, when the drill (200, 200') is inactive, the force of the return spring (184) pushes the secondary rotor (182) in the distal-proximal direction to a proximal stop position in which the rupturing element (121) is located in the first position again.

In one embodiment, the fluid is a hydraulic oil for medical use; in another even more preferred embodiment, the fluid is sterilized water.

Figures 6A, 6B:
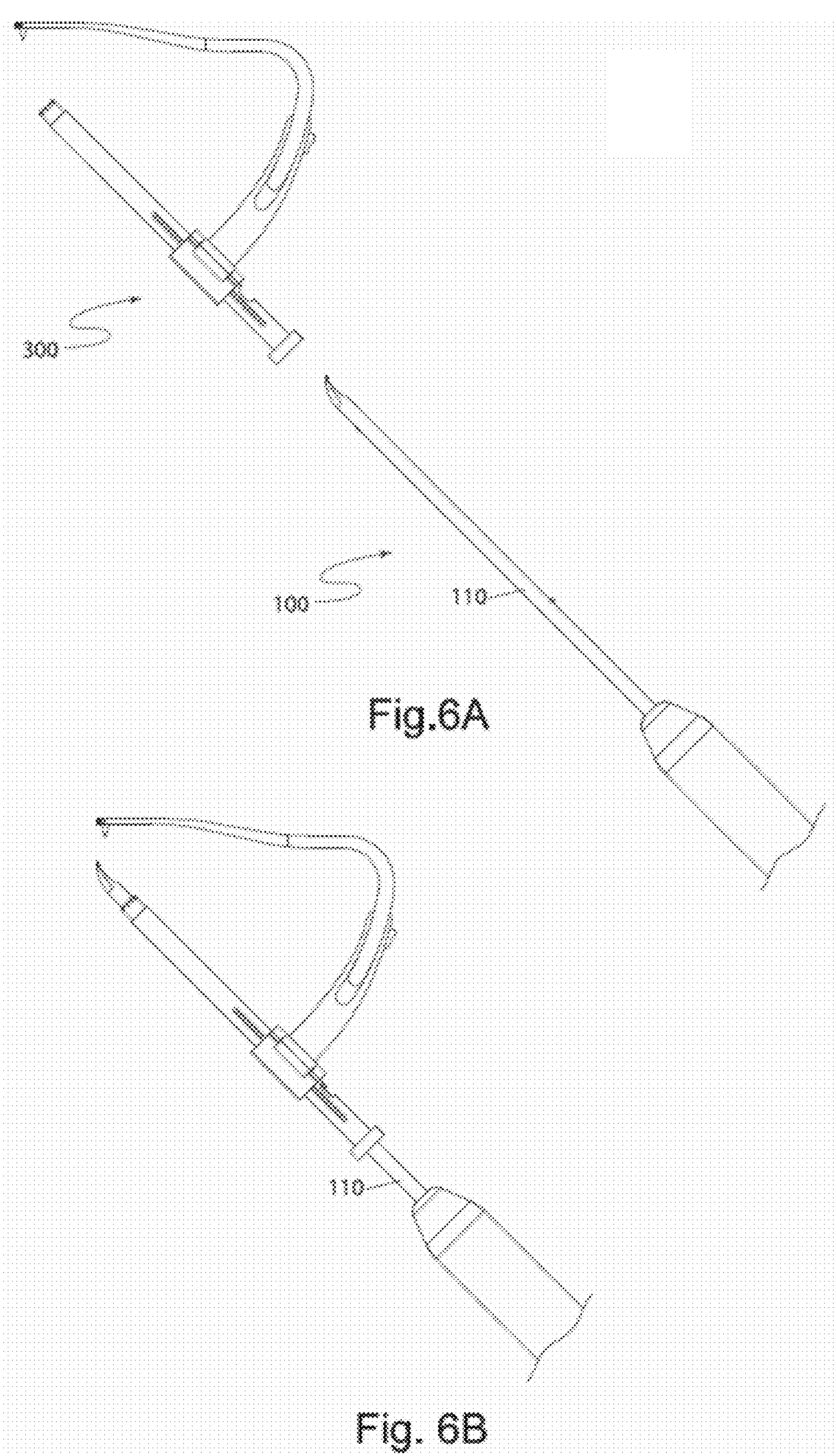
FIGS. 6*a*-6*b:*

FIGS. 6*a*-6*b* show an embodiment of the rupturing tool (100) in which said rupturing tool (100) further comprises a rupturing guide (300).

This rupturing guide (300) is configured for guiding the longitudinal body (110) from an original position, in which the longitudinal body (110) starts to penetrate the first segment of a bone tunnel, to a target position, in which the longitudinal body (110) is correctly positioned so that the rupturing element (121) moves from the first position to the second position, thereby allowing a second bone tunnel segment to be carved and a widened intraarticular outlet opening to be generated.

FIG. 6*a* shows the rupturing tool (100) with a rupturing guide (300) when the longitudinal body (110) is not inserted into the rupturing guide (300) and FIG. 6*b* shows the rupturing tool (100) with a rupturing guide (300) when the longitudinal body (110) is inserted into the rupturing guide (300).

FIGS: 7*a*-7*f* show the rupturing guide (300) in detail.

Figures 7A, 7B:
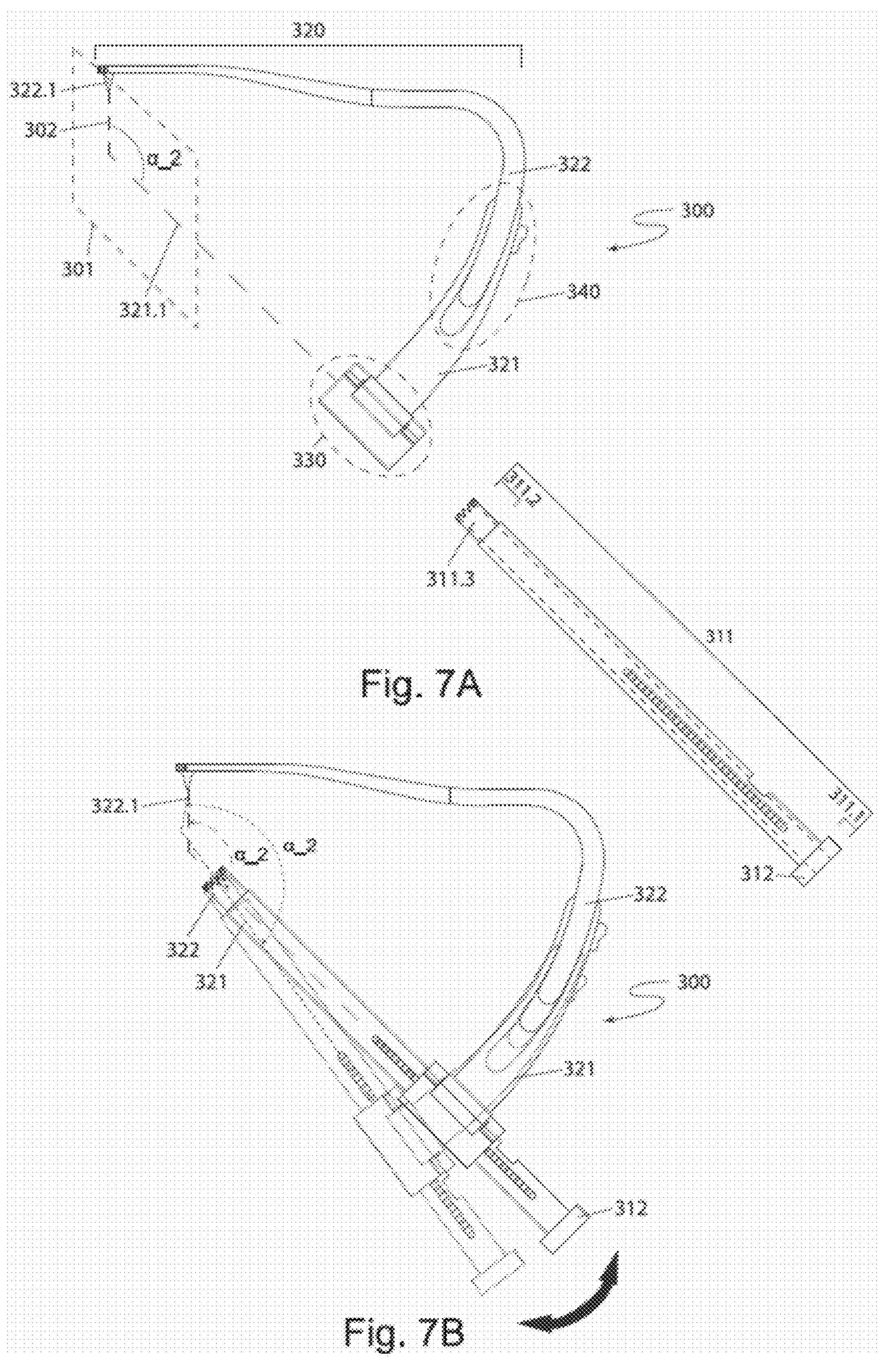
FIGS. 7*a*-7*f:*

FIG. 7*a* shows an exploded perspective view of the rupturing guide (300). As can be seen, this rupturing guide (300) comprises a tubular guide (310) which in turn comprises a longitudinal conduit (311) with a proximal end (311.1) and a distal end (311.2), the longitudinal conduit (311) comprising a distal appendage (311.3) at the distal end (311.2); and a striking edge (312), a prolongation of the longitudinal conduit (311) at the proximal end (311.1).

The longitudinal conduit (311) is configured for housing therein the longitudinal body (110), and the at least one tubular guide (310) is oriented according to a first longitudinal guiding axis (321.1).

The striking edge (312) is configured for receiving a striking force in the direction of the first longitudinal guiding axis (321.1).

In this figure, the distal appendage (311.3) is a peripheral recess. Other examples of distal appendage (311.3) comprise a trilobular tip, or two tips, or a beveled recess, or polyhedral faces.

The rupturing guide (300) further comprises a guide arch (320) which in turn comprises:

a proximal arch portion (321) with a first coupling means (330) configured for securely coupling and uncoupling the proximal arch portion (321) with respect to the tubular guide (310) in a plurality of different positions along the first longitudinal guiding axis (321.1);

a distal arch portion (322) which in turn comprises a distal tip (322.2) oriented according to a second longitudinal guiding axis (322.1); and second coupling means (340) configured for coupling the distal arch portion (322) to the proximal arch portion (321) in a plurality of different positions, such that for each of said positions the first longitudinal guiding axis (321.1) and the at least one second longitudinal guiding axis (322.1) form a different angle $\alpha 2$ with respect to one another.

As can be seen in FIG. 7*a*, both longitudinal guiding axes (321.1, 322.1) are comprised in a second sagittal plane (301).

FIG. 7*b* shows a non-exploded perspective view of the rupturing guide (300). This figure illustrates how the distal arch portion (322) is coupled by means of the second coupling means (340) in two different positions to the proximal arch portion (321). In these two positions, the first longitudinal guiding axis (321.1) and the second longitudinal guiding axis (322.1) form a different angle $\alpha 2$ with respect to one another.

Additionally, FIG. 7*b* shows how the guide arch (320) is securely assembled on a tubular guide (310) as a result of the first coupling means (330), particularly in a position from among the plurality of different positions in which it can be placed along said tubular guide (310). In this particular example, the first coupling means (330) of the guide arch (312) is in the form of a cylindrical clamp or clip, as seen in detail in FIGS. 7*c* and 7*d*. To assemble the guide arch (320) on the tubular guide (310), the first coupling means (330) is opened according to the direction of the arrow and once positioned in the desired position, the clamp or clip is closed such that said clamp or clip surrounds the tubular guide (310) in a fixed position.

Figures 7C, 7D:
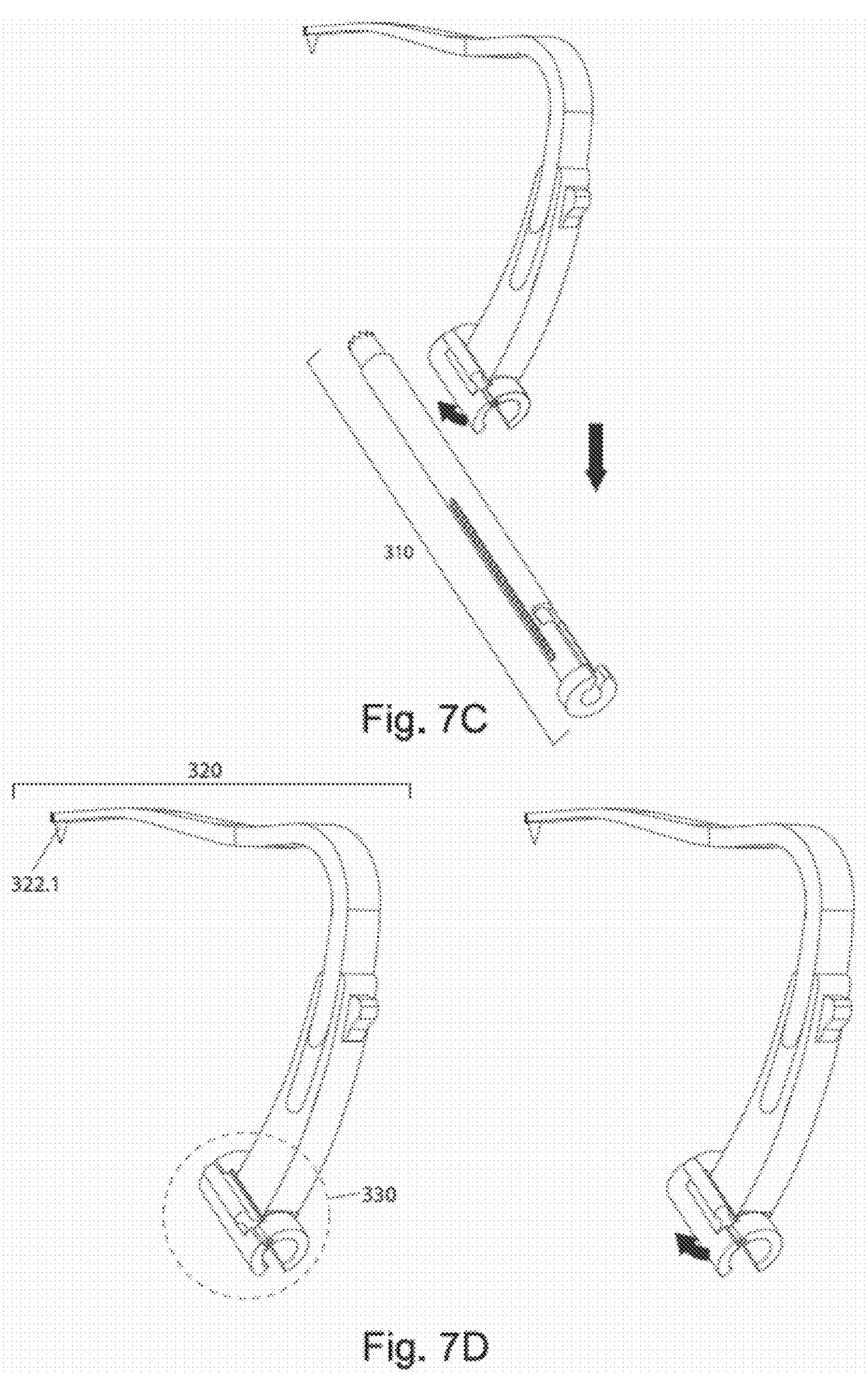

FIG. 7*d* shows by means of arrows how the guide arch (320) is disassembled from the tubular guide (310), that is, opening the clamp or clip in the direction of the top arrow.

Figures 7E, 7F:
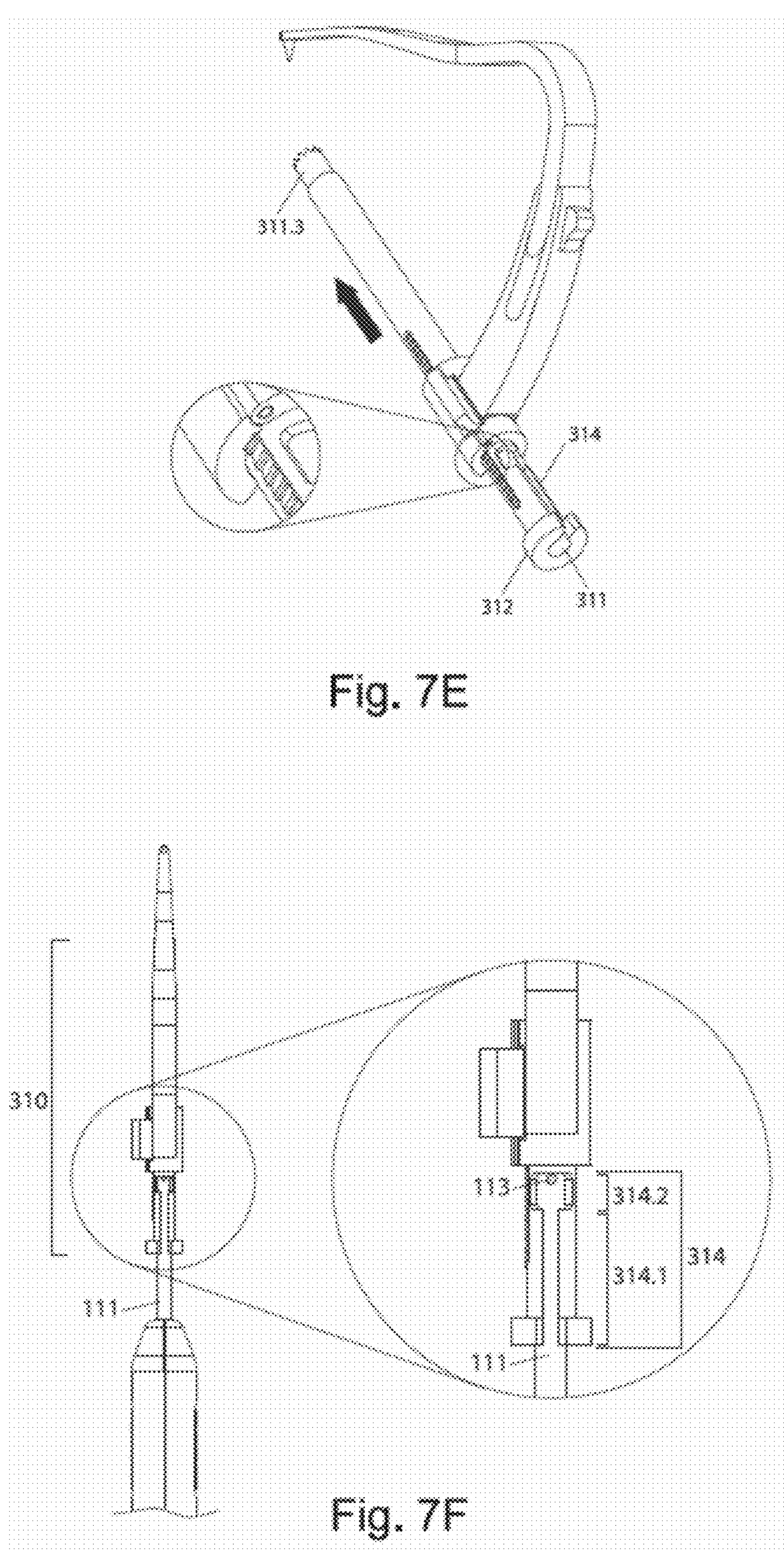

FIG. 7*e* shows in detail a particular embodiment in which the first coupling means (330) comprises a longitudinal ratchet. Said longitudinal ratchet comprises a succession of wedge-shaped teeth or projections arranged in the tubular guide (310) and at least one complementary, also wedge-shaped tooth or projection in the guide arch (320), configured and sized for fitting between two of the consecutive teeth or projections of the tubular guide (310). In that sense, as the tubular guide (310) moves with respect to the guide arch (320), the at least one complementary tooth or projection of the guide arch (320) goes from one position to another along the ratchet, with each of said positions being located between two consecutive teeth or projections of the guide. In that sense, as a result of this first coupling means (330) of the guide arch, the proximal arch portion (321) is allowed to be securely coupled in a plurality of different positions along the at least one tubular guide (310).

FIG. 7*f* shows in detail a particular embodiment of the interconnection between the main body (111) of the longitudinal body (110) and the tubular guide (310). In this embodiment, the tubular guide (310) further comprises a hole (314) which in turn comprises a first portion (314.1) and a second portion (314.2) which, as can be seen in the figure, are attached to one another. In turn, the main body (111) of the longitudinal body (110) comprises a second projection (113).

The first portion (314.1) of the hole (324) is sized and configured for receiving and guiding the second projection (113) from a proximal location, in which the second projection (113) is introduced in said first portion (314.1), to a distal location, in which the second projection (113) is introduced in the second portion (314.2). This occurs when the longitudinal body (110) of the rupturing tool (100) is inserted into and moves along the inside of the tubular guide (310) of the rupturing guide (300).

The second portion (314.2) is sized and configured for abutting with the second projection (113) when the first sagittal plane (103) of the rupturing tool (100) is rotated an angle $\gamma$ with respect to the second sagittal plane (301) of the rupturing guide (300).

In that sense, once the second projection (113) is located inside the second portion (314.2), it slides in a direction perpendicular to the second sagittal plane (301) along said second portion (314.2) of the hole (314) until abutting with the ends or limits of the second portion (314.2). This sliding results from the rotation of the longitudinal body (110) from left to right and vice versa when it is housed inside the rupturing guide (300). In that sense, the hole (314) as a whole allows limiting the angle which the first sagittal plane (103) can form with the second sagittal plane (301).

In this example, the first portion (314.1) of the hole (314) is an elongated portion parallel to the second sagittal plane (301) and the second portion (314.2) of the hole (314) is a quadrilateral-shaped portion. Both portions form a "T" with one another.

As mentioned throughout the document, widening of the intraarticular outlet opening is generated in a plane which is perpendicular to the second sagittal plane (301). As a result of the second portion (314.2) of the hole (314) according to this embodiment, the user can cause the longitudinal body (110) to move back in the distal-proximal direction in order to widen the intraarticular outlet opening in other planes parallel to the plane in which the tunnel was initially created. Evidently, in this new widening, the user must continue to turn the longitudinal body (110) from left to right so that the first sagittal plane is rotated with respect to the second sagittal plane.

In a particular embodiment, the tubular guide (310) comprises a single longitudinal hole (314) and the main body (111) of the longitudinal body (110) comprises at least one second projection (113), wherein the longitudinal hole (314) is sized and configured for receiving and guiding the at least one second projection (113) from a proximal location to a distal location and vice versa.

Figures 8A, 8B:
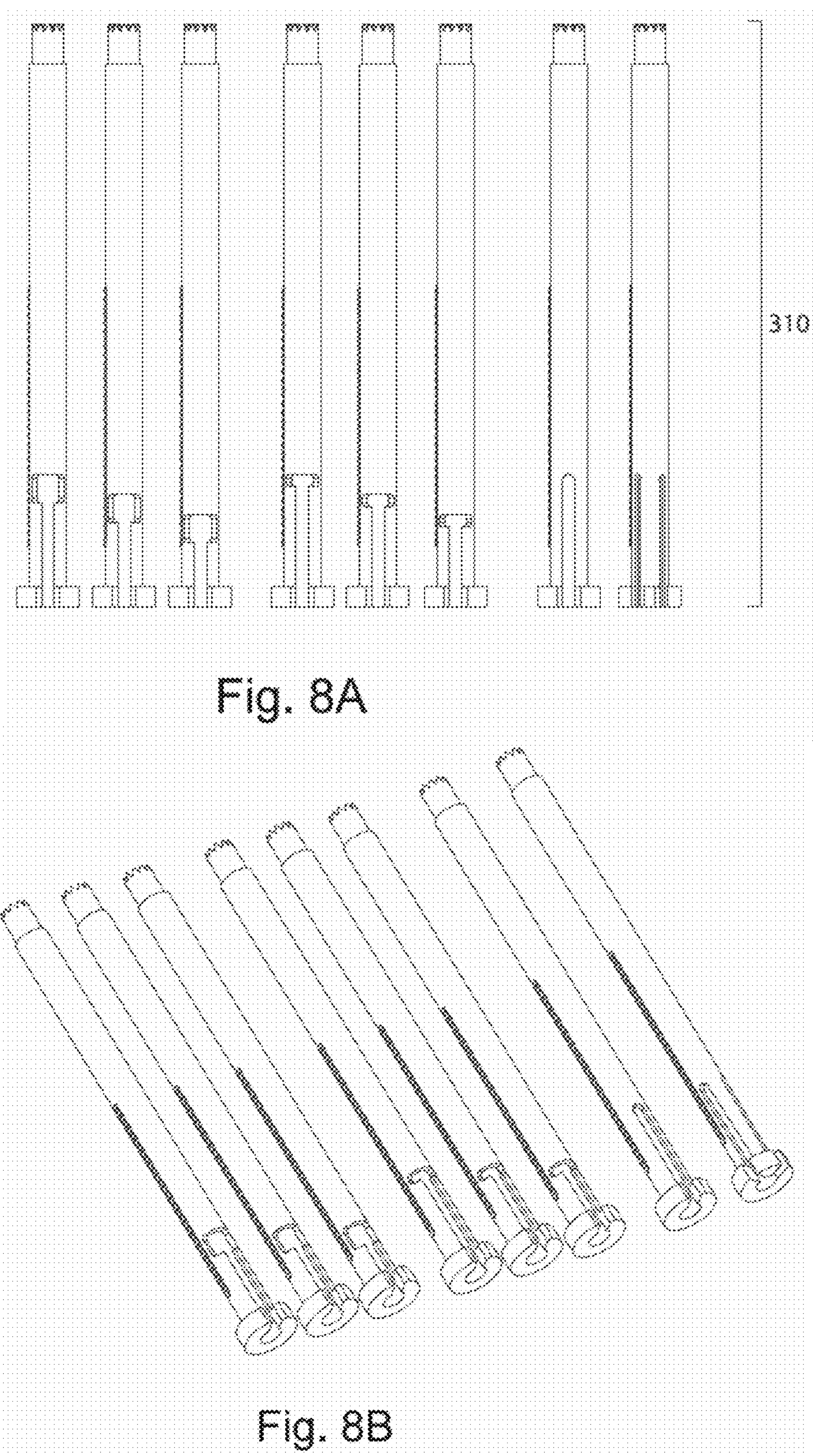
FIGS. 8*a*-8*b:*

FIGS. 8*a*-8*b* show a top view and a perspective view of a plurality of tubular guides (310). The hole (314) of all of said guides is different in shape and/or dimensions. For example, a tubular guide (310) with a single hole and several tubular guides (310) with holes (314) comprising a first portion (314.1) and a second portion (314.2) of different shapes and sizes are shown.

Figure 9:
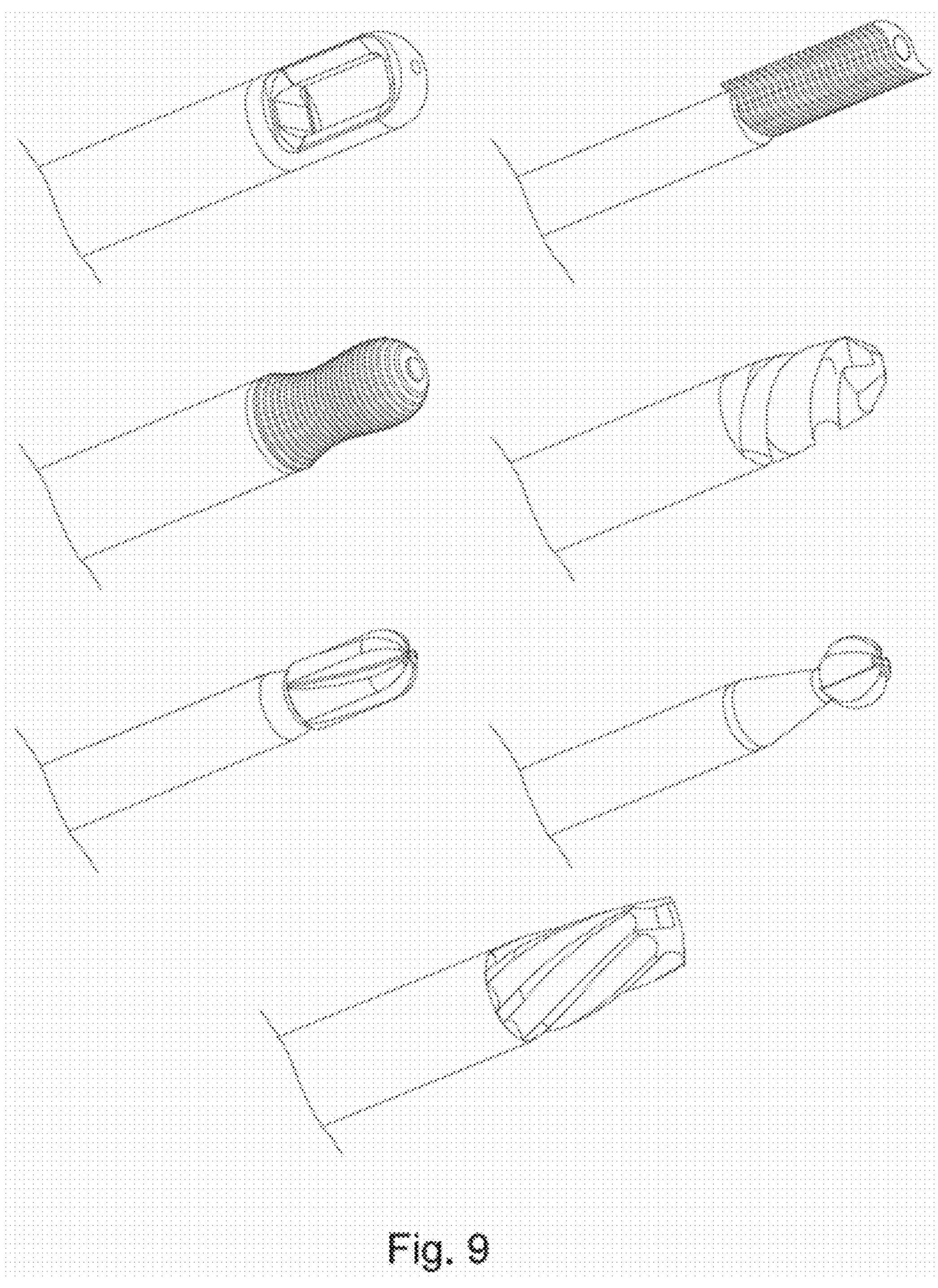
FIG. 9.

FIG. 9 shows different examples of configurations of the rupturing element (121).

FIGS. 10*a*-10*i* show a rupturing system (400) for surgical interventions comprising a rupturing movement generator device (200) and a rupturing tool (100) according to any of the preceding embodiments.

The rupturing movement generator device (200), in this case a drilling device (200), is configured for generating and performing a rupturing movement, in this particular example, a rotary movement. Additionally, it is configured for transferring the rupturing movement to the movement transfer element (122).

Figures 10A, 10B, 10C:
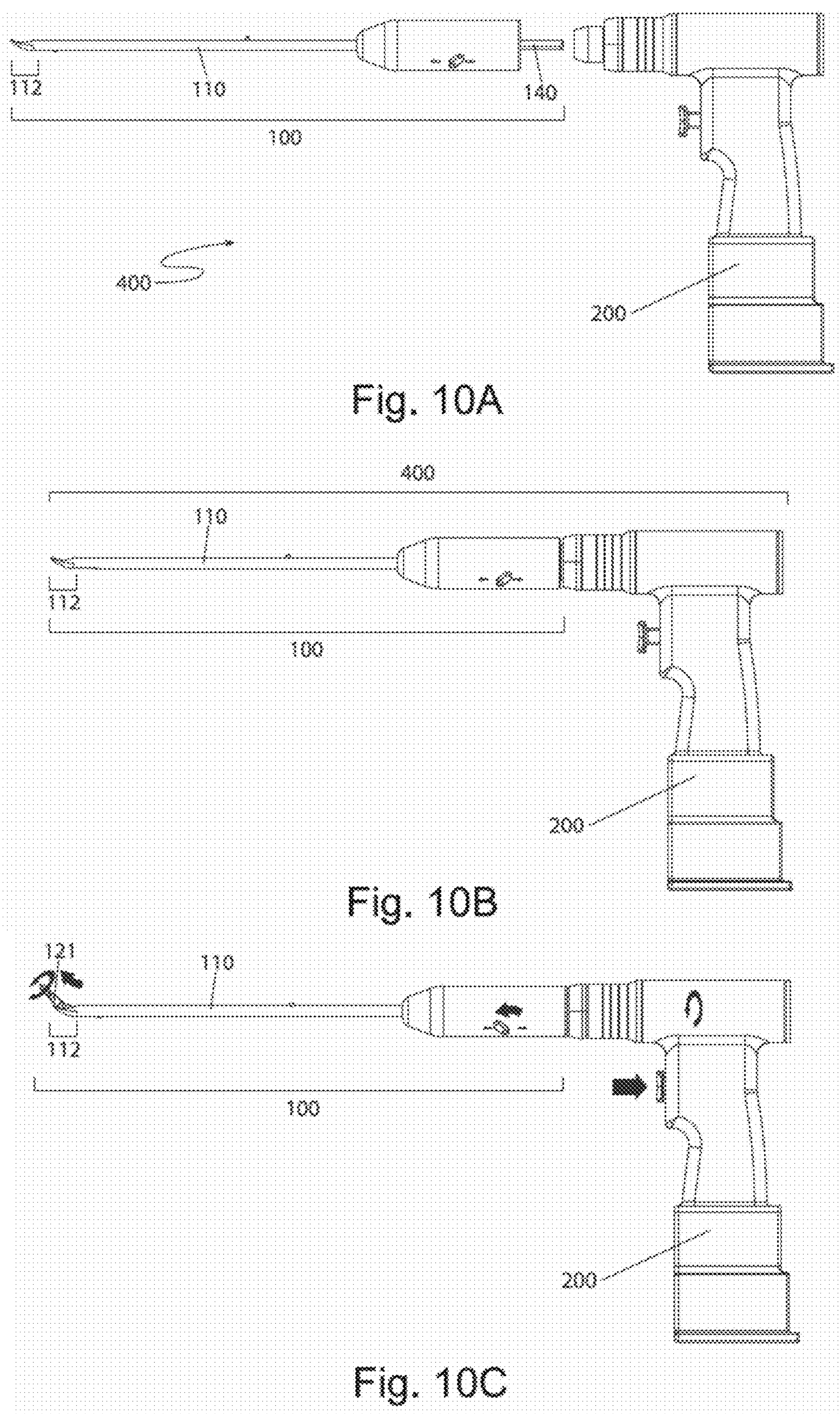

In particular, FIG. 10*a* shows a side view of the system (400) with the tool (100) uncoupled from the rupturing movement generator device (200).

FIG. 10*b* shows a side view of the system (400) with the tool (100) coupled to the rupturing movement generator device (200) which is inactive.

FIG. 10*c* shows a side view of the system (400) indicating by means of arrows that the rupturing movement generator device (200) is activated (arrow pointing at the trigger of the drill), which causes the rotation and forward movement of the rupturing assembly (120), causing the rupturing element (121) to be located in the second position protruding through the opening (115) of the distal tip (112). The rupturing tool (100) of FIGS. 10*d*-10*f* is couplable to the rupturing movement generator device (200) by means of the movement transfer element (122). To that end, the rupturing tool (100) comprises a first attachment and/or coupling means (140) shown in detail in FIG. 10*f*, configured for coupling the movement transfer element (122) to the rupturing movement generator device (200).

The rupturing tool (100) of FIGS. 10*g*-10*i* is couplable to the rupturing movement generator device (200) by means of the movement transfer element (122) and by means of the support body (160.1, 170.1, 180.1) as a result of a first and a second attachment and/or coupling means (140, 150). The assembly of the first and second attachment and/or coupling means (140, 150) is shown in detail in FIG. 6*i*, which is configured for coupling the movement transfer element (122) and the support body (160.1, 170.1, 180.1) to the rupturing movement generator device (200).

Figures 11A, 11B, 11C:
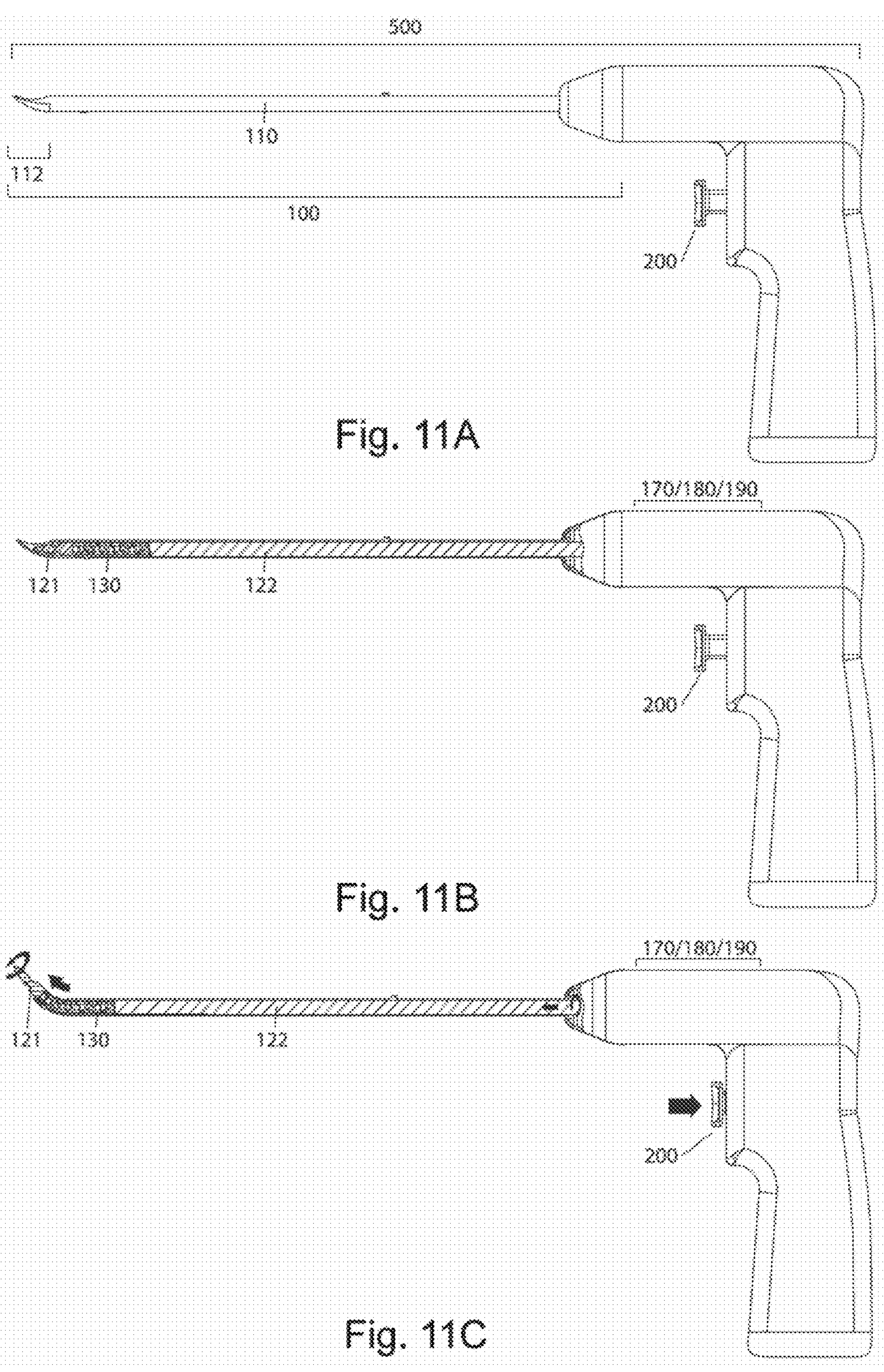
FIGS. 11*a*-11*c:*

FIGS. 11*a*-11*c* show a rupturing system (500) for surgical interventions comprising:

- a rupturing movement generator device and linear reciprocating movement generator (200') configured for generating and performing a rupturing movement, and for generating and performing a linear or reciprocating movement;
- a rupturing tool (100) without movement transmission and conversion means;

wherein the rupturing movement and linear or reciprocating movement generator device (200') is further configured for transferring the rupturing movement and the linear or reciprocating movement to the movement transfer element (122).

In this example, the rupturing tool (100) is furthermore attached to the rupturing movement and linear or reciprocating movement generator device (200') by a first attachment and/or coupling means (140) and by a second attachment and/or coupling means (150).

In the particular example of FIGS. 11*a*-11*c*, the rupturing movement and linear movement generator device (200') comprises mechanical and/or electromagnetic and/or electronic means for generating rupturing movement and linear or reciprocating movement which are activated simultaneously with one and the same push-button.

In particular, FIG. 11*a* shows a side view of the system (500).

FIG. 11*b* shows a section view of the system (500), in which the rupturing element (121) is located in the first position.

FIG. 11*c* shows a section view of the system (500), in which the rupturing element (121) is located in the second position. Additionally, it is indicated by means of arrows that the drilling device (200') is activated (arrow pointing at the trigger of the drill), which causes the rotation and forward movement of the rupturing assembly (120), causing the rupturing element (121) to be located in the second position protruding through the opening of the distal tip (112) executing simultaneous rotary and reciprocating movements.

For any of the systems (400, 500) described in the present application, the first sagittal plane of the rupturing tool (100) can maintain a fixed position with respect to the sagittal plane of the rupturing movement generator device.

In a particular embodiment not depicted in the figures, the first sagittal plane (103) of the rupturing tool (100) can rotate between a plurality of positions, for each of which the first sagittal plane (103) of the rupturing tool (100) rotates with respect to the sagittal plane of the rupturing movement generator device (200, 200').

Advantageously, the rotation of the first sagittal plane (103) of the rupturing tool (100) with respect to the sagittal plane of the rupturing movement generator device (200, 200') allows maintaining the sagittal plane of the rupturing movement generator device (200, 200') in a fixed position and rotating only the rupturing tool (100), which facilitates the usability and precision of the rupturing tool (100).

In a particular embodiment, the rupturing system (400, 500) comprises a disposable rupturing tool (100).

In another particular embodiment, the rupturing system (400, 500) comprises a rupturing tool (100) and a rupturing movement generator device (200, 200') which are disposable, with the exception of the motor and the battery of the rupturing movement generator device (200, 200').

Figures 12A, 12B, 12C:
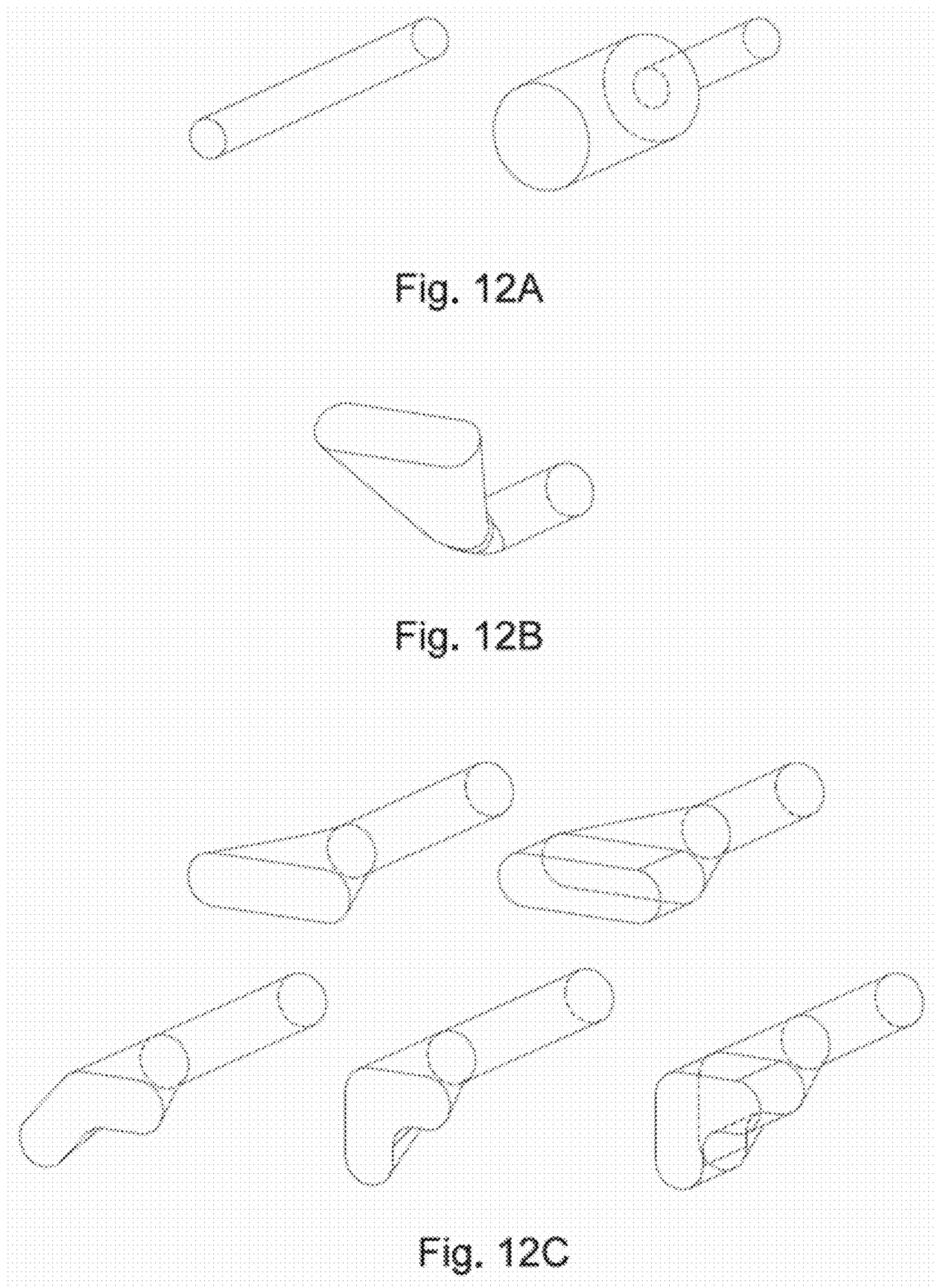
FIG. 12*a*-12*c:*

FIG. 12*a* shows the state of the art in bone tunnel back milling by means of rupturing tools with a single axis of rotation which coincides with the axis of rupture: back milling only provides cylindrical widening of the first bone tunnel.

FIG. 12*b* shows an angled bone tunnel created and widened by means of the rupturing tool of the present invention.

FIG. 12*c* shows different examples for widening a straight bone tunnel by means of the rupturing tool of the present invention.

First example of a surgical procedure performed by means of the rupturing system of the present invention, particularly for repairing the supraspinatus tendon of the shoulder joint.

Figure 13A:
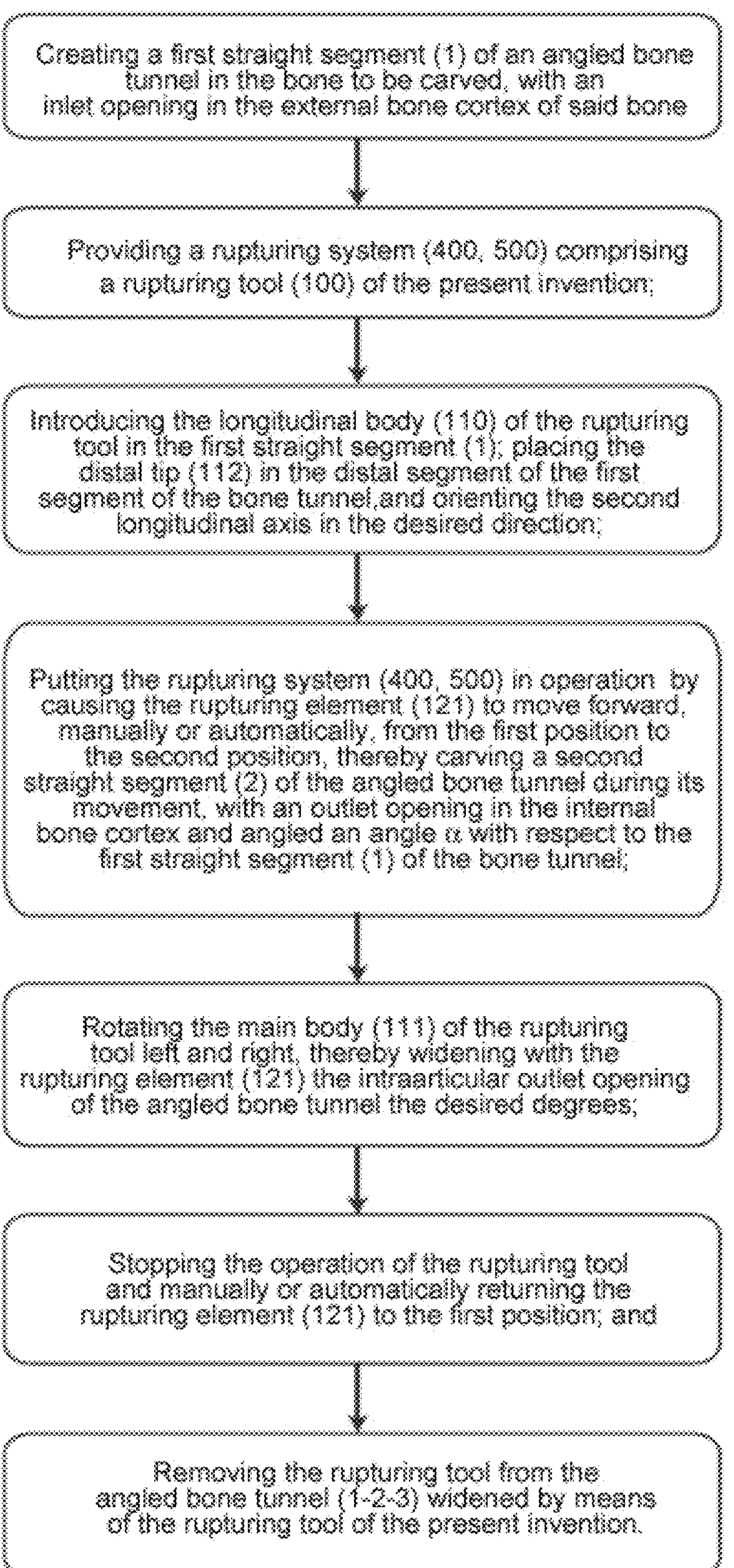
FIGS. 13*a*-13*f:*

In a second inventive aspect, complementary to the first inventive aspect, the invention provides a first method for carving an angled bone tunnel with widened intraarticular outlet opening in a human or animal body during connective tissue repair. This method is illustrated in FIG. 13*a* by means of a flow chart.

The method comprises the following steps:

a) creating a first straight segment (1) of an angled bone tunnel in the bone to be carved, with an inlet opening in the external bone cortex of said bone;

b) providing a rupturing system (400, 500) comprising a rupturing tool (100) of the present invention;

c) introducing the longitudinal body (110) of the rupturing tool in the first straight segment (1); placing the distal tip (112) in the distal segment of the first segment of the bone tunnel, and orienting the second longitudinal axis in the desired direction;

d) putting the rupturing system (400, 500) in operation by causing the rupturing element (121) to move forward, manually or automatically, from the first position to the second position, thereby carving a second straight segment (2) of the angled bone tunnel during its movement, with an outlet opening in the internal bone cortex and angled an angle $\alpha$ with respect to the first straight segment (1) of the bone tunnel;

e) rotating the main body (111) of the rupturing tool left and right, thereby widening with the rupturing element (121) the intraarticular outlet opening of the angled bone tunnel by the desired degrees;

f) stopping the operation of the rupturing tool and manually or automatically returning the rupturing element (121) to the first position; and g) removing the rupturing tool from the angled bone tunnel (1-2-3) widened by means of the rupturing tool of the present invention.

In this embodiment, step a) is performed with any tool capable of carving a straight bone tunnel in a bone, for example, a bit or a mill coupled to a surgical drill.

In a particular embodiment, the connective tissue to be repaired is a supraspinatus muscle tendon of the shoulder joint.

Figure 13B:
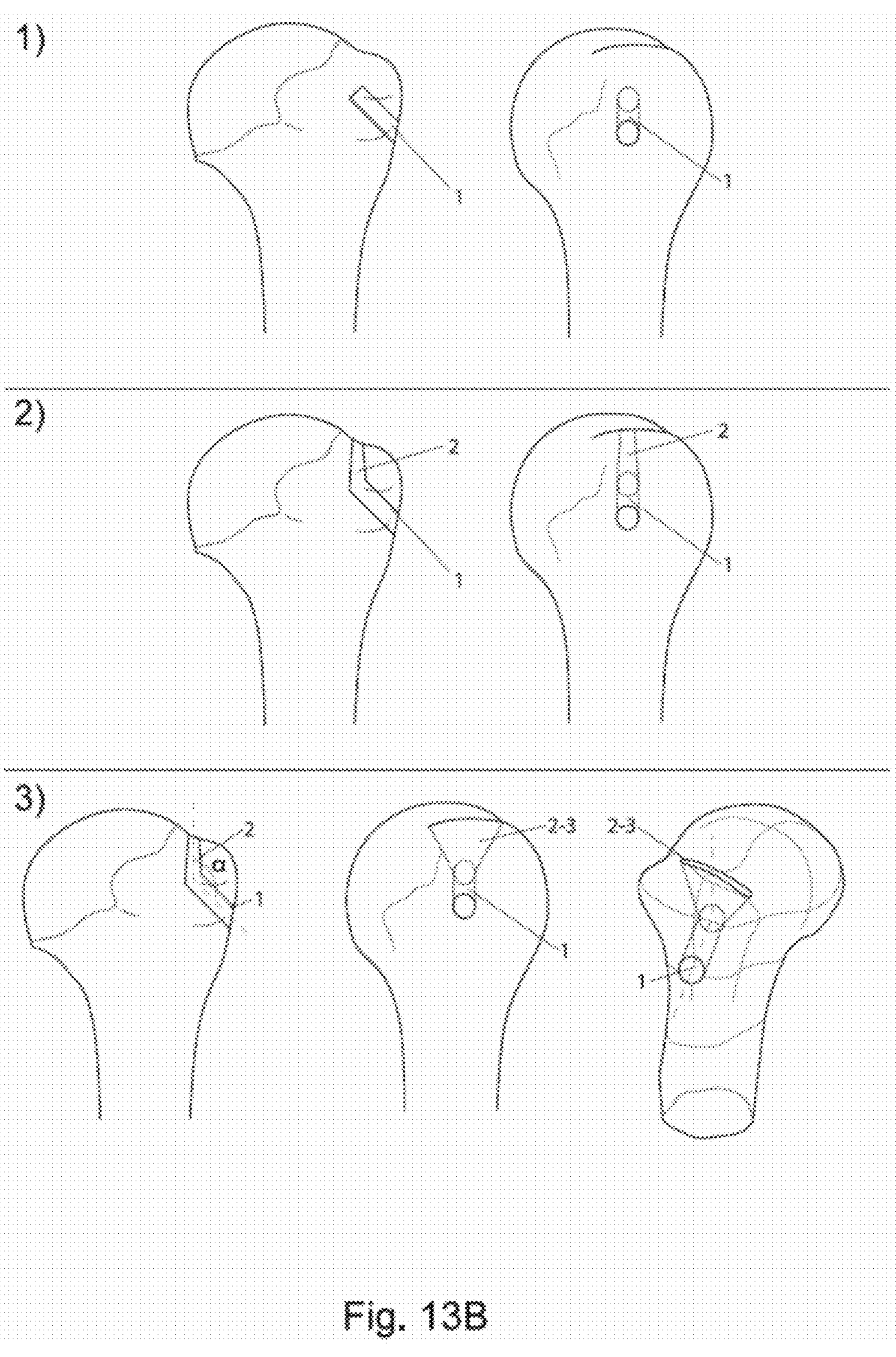

FIG. 13*b* shows in detail the different segments of the bone tunnel carved in the greater tubercle of the humerus:

1) side and front views of the first straight segment (1) of the bone tunnel.

2) side and front views of the first straight segment (1) and of the second straight segment (2) of the bone tunnel.

3) side, front, and perspective views of the complete bone tunnel with the intraarticular outlet opening (2-3) widened by means of using any of the systems of the invention.

Figure 13C:
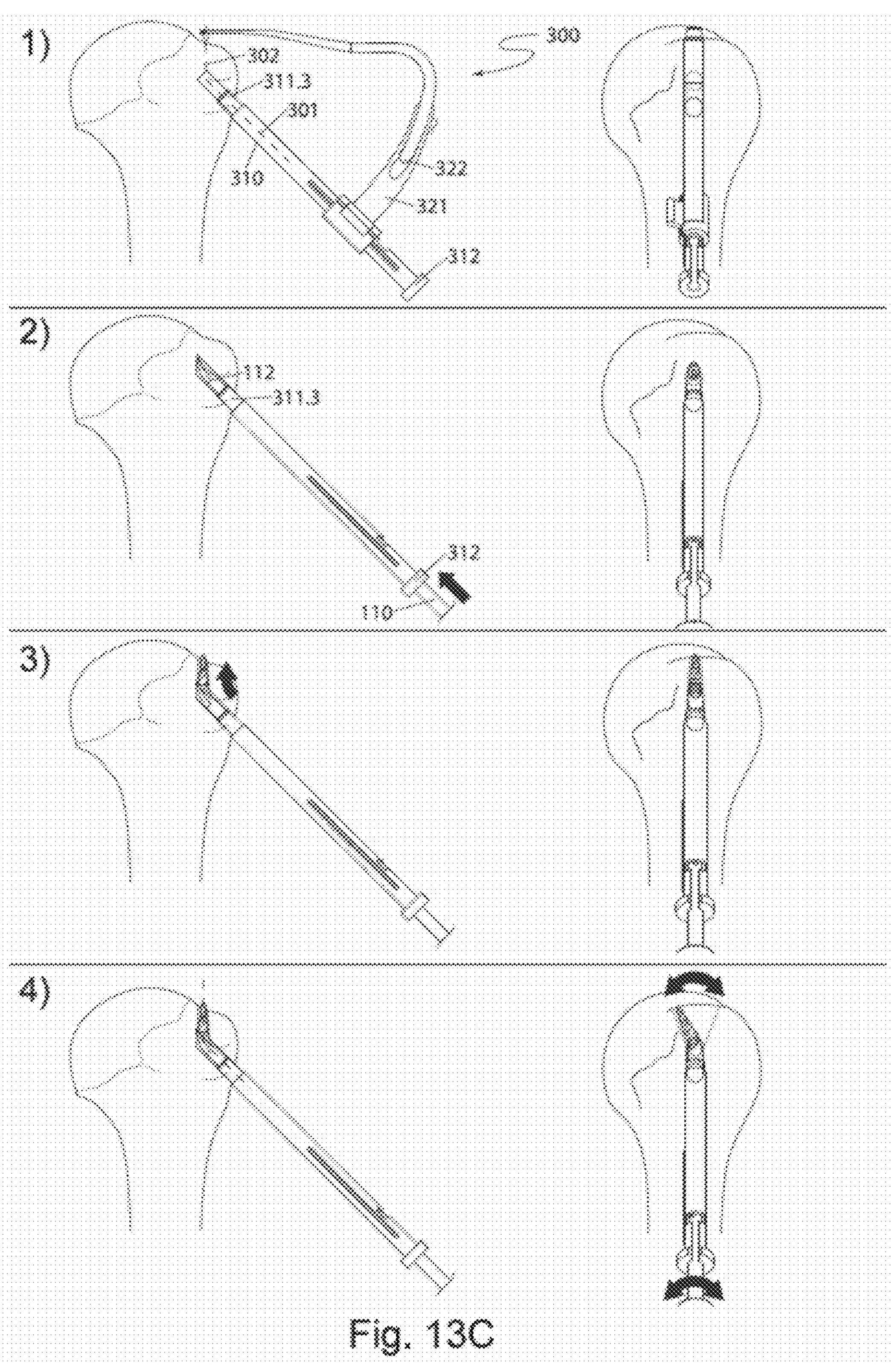

FIG. 13*c* shows a more preferred particular embodiment, in which the rupturing system (400, 500) used in the method comprises a rupturing tool (100) which in turn comprises a rupturing guide (300).

In this embodiment of the method, steps b) and c) comprises the following sub-steps:

b1) inserting the distal tip (322.2) of the distal portion (322) of the guide arch (320) of the rupturing guide (300) into the patient's body, positioning said distal tip (322.2) approximately in the center of the original insertion footprint;

b2) with the guide arch (320) parallel to the coronal plane, positioning the distal end of the tubular guide (310) of the rupturing guide (300) in the external bone cortex of the bone to be carved at an approximate distance of between 15 and 25 mm in distance from the greater tubercle;

b3) carving a first straight segment of the angled bone tunnel using a bit with laser depth marking;

b4) removing the bit and applying a striking force on the striking edge (312) of the tubular guide (310) so that the distal appendage (311.3) of the tubular guide (310) penetrates the first segment (1) of the bone tunnel;

b5) introducing the longitudinal body (110) of the rupturing tool (100) in the longitudinal conduit (311) of the tubular guide (310);

b6) uncoupling the guide arch (320) from the tubular guide (310);

Preferably, in step b2), a tubular guide (310) the positioning hole (314) of which must have a length which adapts to the patient's anatomy, is selected.

Additionally, with the rupturing tool (100) comprising a rupturing guide (300), step e) of the method would comprise the following sub-step:

e) with the rupturing system (400, 500) activated and the longitudinal body (110) of the rupturing tool (100) inserted into the longitudinal conduit (311), rotating the longitudinal body (110) right and left with respect to the second sagittal plane (303), thereby widening the outlet opening of the second bone tunnel (2) in the shape of a fan or funnel (3).

In an even more particular embodiment, rotating the longitudinal body (110) right and left with respect to the second sagittal plane (303) is limited by the interaction between the hole (314) of the tubular guide (300) and the first projection (113) of the longitudinal body (110).

In another embodiment, the method further comprises a sub-step of causing the longitudinal body (110) to move back in the distal-proximal direction and/or of causing the longitudinal body (110) to move forward in the proximal-distal direction, by a specific distance, while the system (400) is activated, and rotating the longitudinal body (110) right and left with respect to the second sagittal plane (303), thereby widening the outlet opening of the second bone tunnel (2) in the shape of a fan or funnel (3) in one or more planes parallel to the plane in which it was initially created in step e).

Figure 13D:
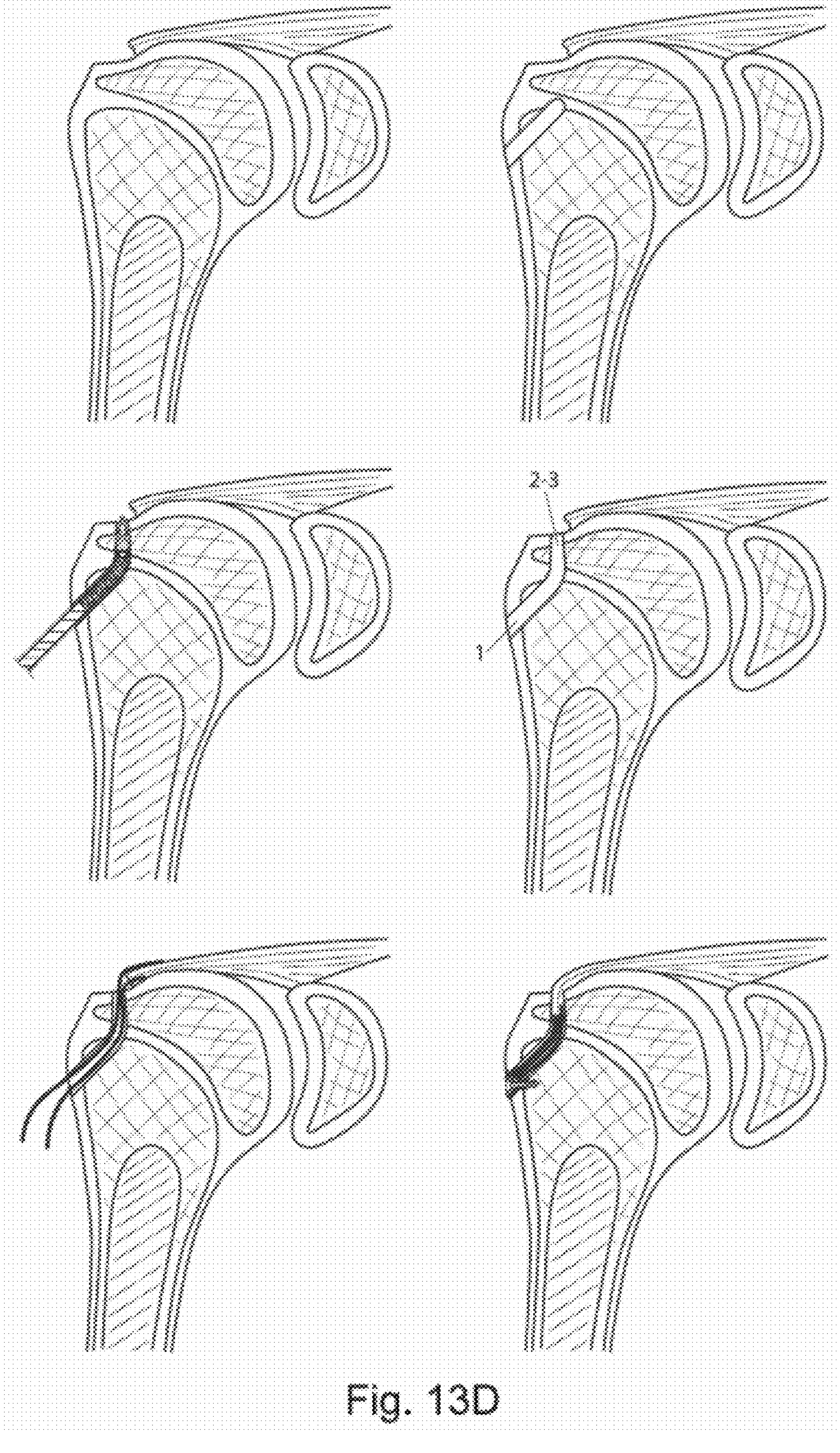

FIG. 13*d* shows a musculoskeletal diagram of the bone tunnel (1-2-3) carved with one of the systems (400, 500) of the invention and the insertion of a graft for repairing a supraspinatus muscle tendon of the shoulder joint.

In the particular example of repairing the damaged supraspinatus muscle tendon of the rotator cuff, the dimensions of the intraarticular outlet opening of the bone tunnel to be created must be such that they allow the insertion of the end of the damaged tendon which, at the height of the rotator chord, has measurements of between 4 mm and 5 mm in thickness and between 20 mm and 25 mm in width. However, these particular measurement ranges provided in the preceding examples must be adapted based on each anatomy and on the final application for which the rupturing tool is used which, in a general use, is suitable for rupturing any connective tissue and/or cartilage tissue and/or bone tissue, in medicine or veterinary.

Once the angled bone tunnel is created and the intraarticular outlet opening widened into a fan or funnel by means of any of the rupturing systems (400, 500) of the invention, the end of the supraspinatus muscle tendon being repaired is sutured and the suture bands are passed through the widened angled bone tunnel (1-2-3), for example, by means of a curved suture passer. FIG. 13*d* shows on the bottom left part the end of the tendon which already passes through the anatomically widened opening of the bone tunnel and the suture bands which come out of the bone tunnel. FIG. 13*d* shows on the bottom right part the suture bands (20) retained by means of a cortical polysuture fixing device (10) which can be, for example, the one described in patent U.S. Pat. No. 5,630,824 or the one described in European patent EP3141216 B1.

Figure 13E:
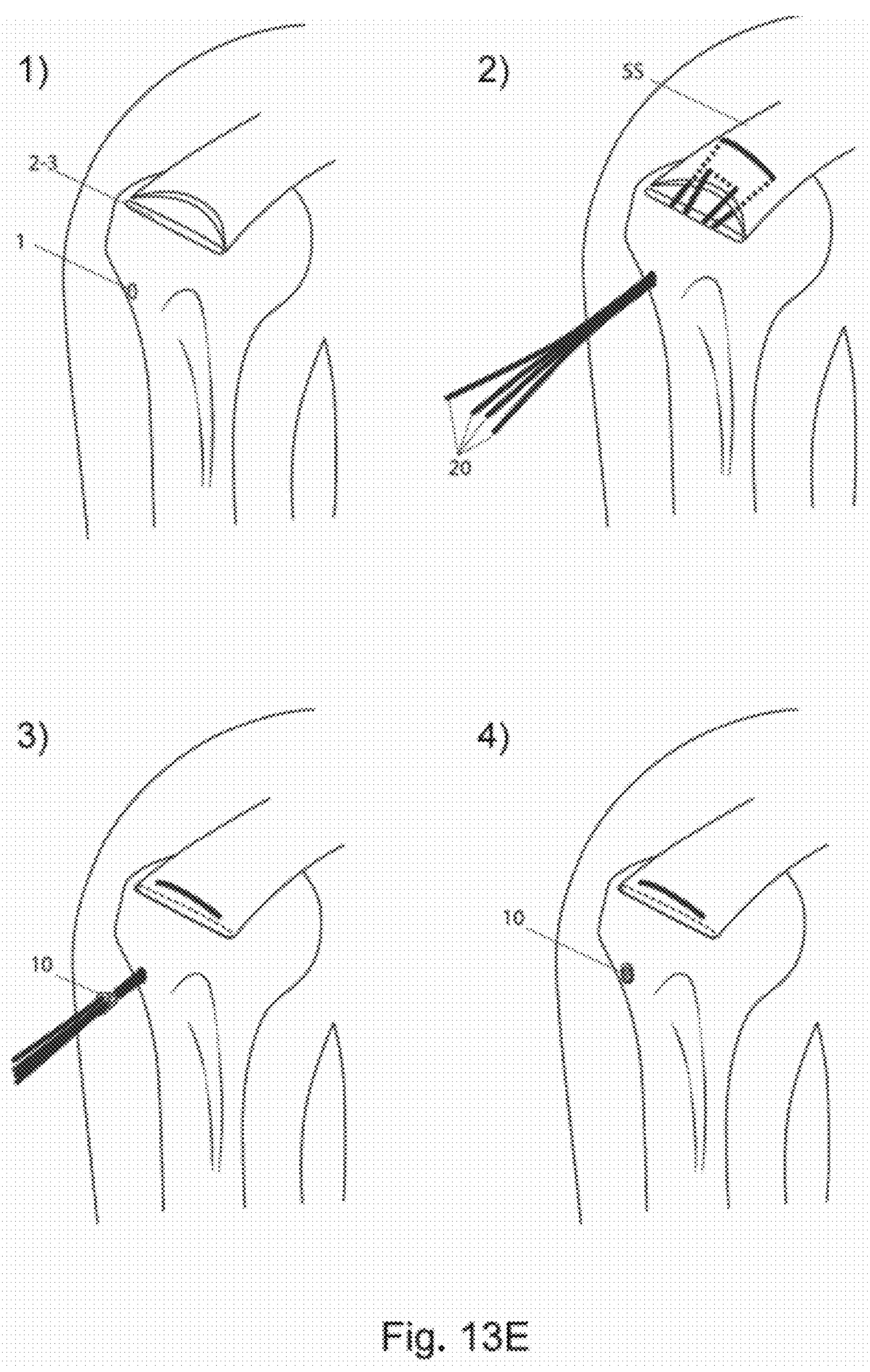

FIG. 13*e* shows perspective views of the same method illustrated in the figures in the center part and in the bottom part of FIG. 13*d*. In particular, the figure shows the repair of a partial supraspinatus muscle tendon rupture by means of a widened angled bone tunnel (1-2-3) created with any of the rupturing systems (400, 500) of the invention and using suture bands (20) with which the end of the tendon is passed through the anatomically widened opening of the bone tunnel. The bottom right part of the figure shows the suture bands (20) retained by means of a cortical polysuture fixing device (10) which can be, for example, the one described in patent U.S. Pat. No. 5,630,824 or the one described in European patent EP3141216 B1.

Figure 13F:
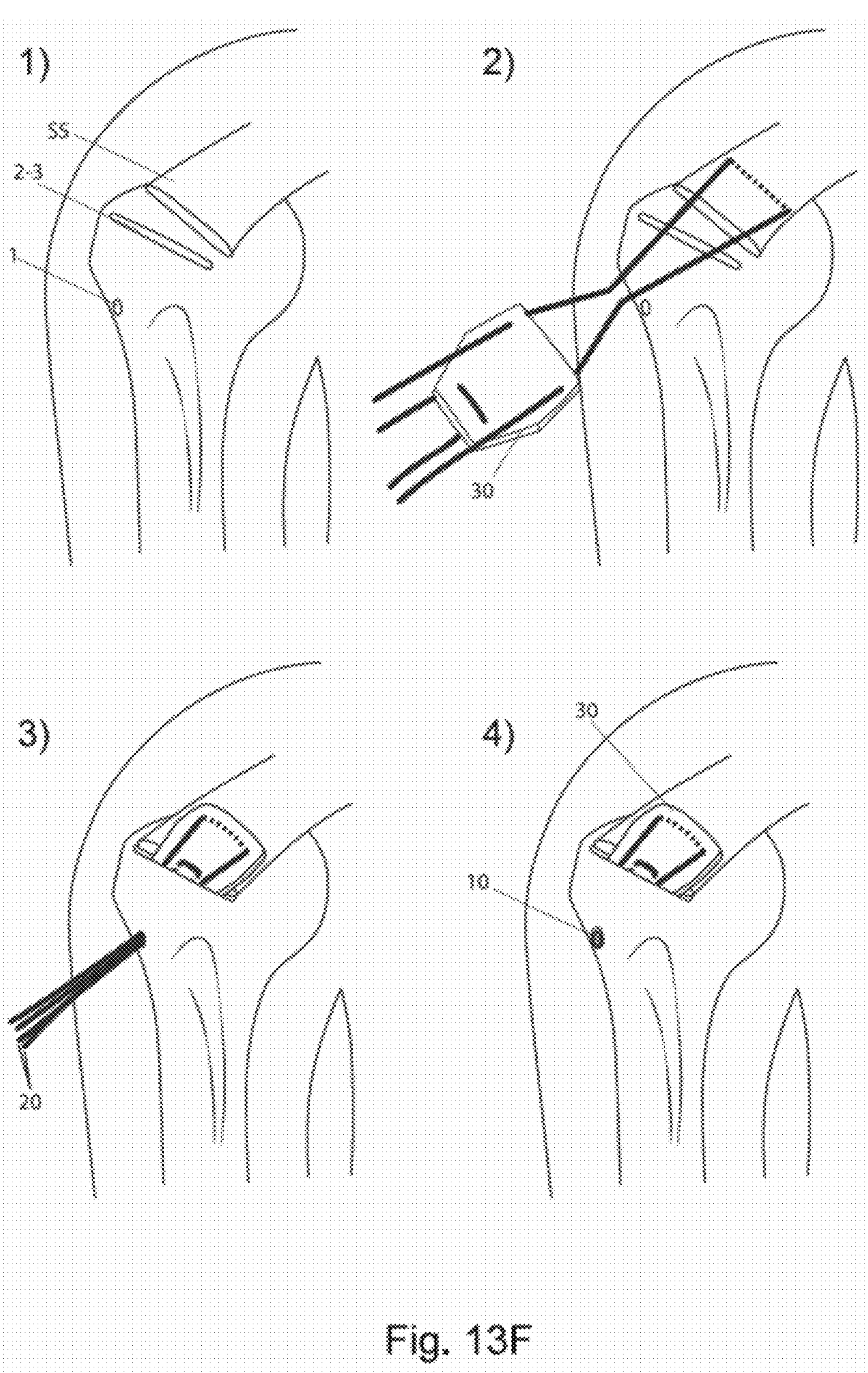

FIG. 13*f* shows a general view of the steps of a method for repairing a complete supraspinatus muscle tendon rupture. This method requires creating an angled bone tunnel (1-2-3) widened by means of any of the rupturing systems (400, 500) of the invention, and the use of augmentation tissue (30) and suture bands (20) with which the end of the augmentation tissue (30) is passed through the anatomically widened opening of the bone tunnel. FIG. 13*f* shows on the bottom right part the suture bands (20) retained by means of a cortical polysuture fixing device (10) which can be, for example, the one described in patent U.S. Pat. No. 5,630,824 or the one described in European patent EP3141216 B1.

In a particular embodiment, the augmentation tissue (30) is a decellularized dermal tissue. In another particular embodiment, the augmentation tissue (30) comprises biodegradable biopolymer fibers. In another particular embodiment, the augmentation tissue (30) comprises a bioabsorbable poly(lactic-co-glycolic acid) (PLGA) aligned microfiber scaffold.

Taking into account that failure rates of up to 68% are reported for complete supraspinatus muscle tendon ruptures (Jost B, Pfirrmann C W A, Gerber C. *Clinical outcome after structural failure of rotator cuff repairs. J Bone Joint Surg Am* 2000; 82:304-14.), in both cases, the objective is to achieve revascularization of the end of the tendon through the osteointegration of the augmentation tissue (30)

Second example of a surgical procedure performed by means of the rupturing system of the present invention, particularly for repairing the anterior cruciate ligament of the knee joint.

Figure 14A:
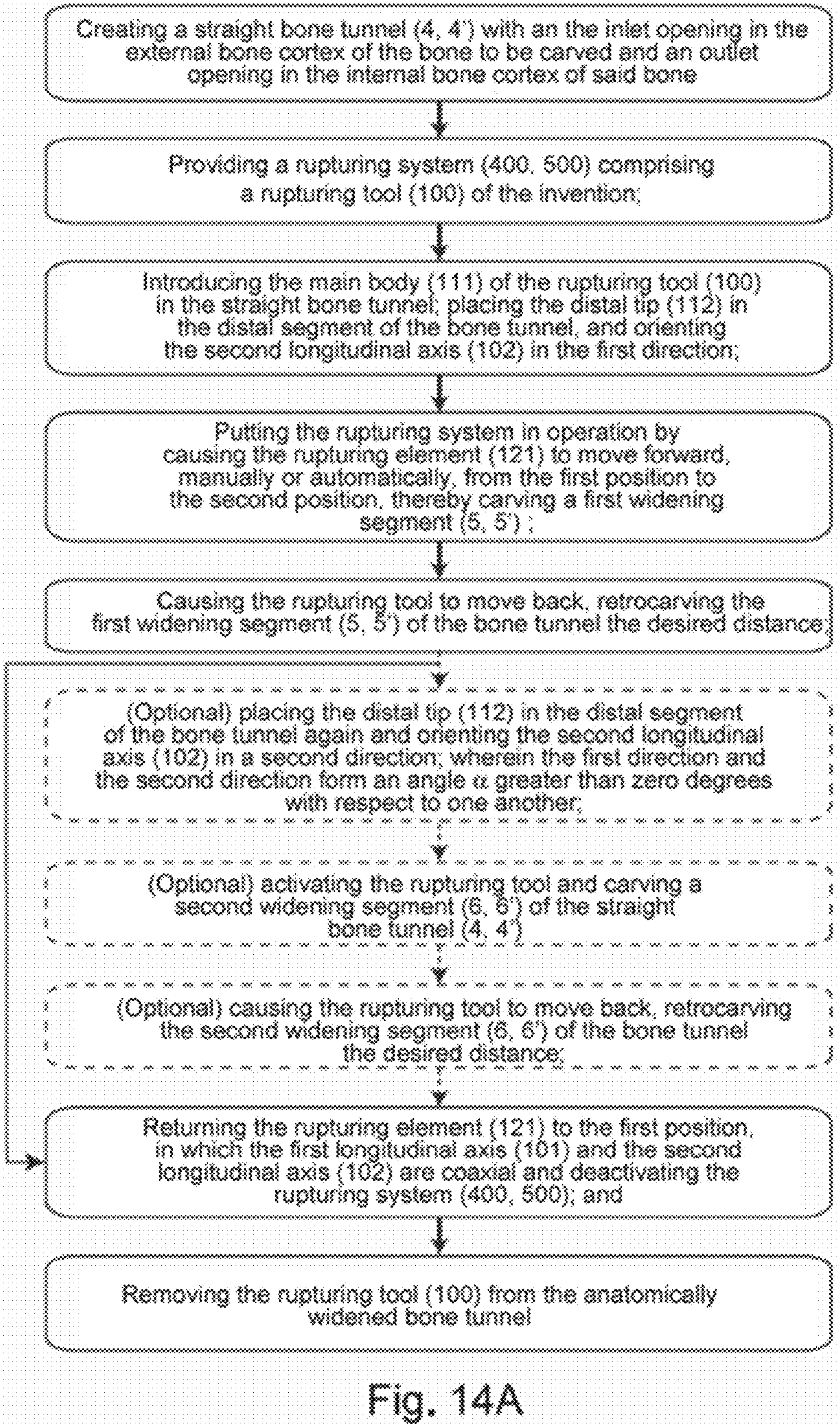
FIGS. 14*a*-14*g:*

In a third inventive aspect, likewise complementary to the first inventive aspect, the invention provides a second method for carving and/or back carving an anatomical bone tunnel in a human or animal body during connective tissue repair. This method is illustrated in FIG. 14*a* by means of a flow chart.

The method comprises the following steps:

a) creating a straight bone tunnel (4, 4') with an inlet opening in the external bone cortex of the bone to be carved and an outlet opening in the internal bone cortex of said bone;
b) providing a rupturing system (400, 500) comprising a rupturing tool (100) of the invention;
c) introducing the main body (111) of the rupturing tool (100) in the straight bone tunnel; placing the distal tip (112) in the distal segment of the bone tunnel, and orienting the second longitudinal axis (102) in a first direction;
d) putting the rupturing system in operation by causing the rupturing element (121) to move forward, manually or automatically, from the first position to the second position, thereby carving a first widening segment (5, 5') during its movement;
e) causing the rupturing tool to move back, back carving the first widening segment (5, 5') of the bone tunnel the desired distance;
f) (optional) placing the distal tip (112) in the distal segment of the bone tunnel again and orienting the second longitudinal axis (102) in a second direction; wherein the first direction and the second direction form an angle α greater than zero degrees with respect to one another;
g) (optional) activating the rupturing tool and carving a second widening segment (6, 6') of the straight bone tunnel (4, 4');
h) (optional) causing the rupturing tool to move back, back carving the second widening segment (6, 6') of the bone tunnel the desired distance;
i) returning the rupturing element (121) to the first position, in which the first longitudinal axis (101) and the second longitudinal axis (102) are coaxial and deactivating the rupturing system (400, 500); and
j) removing the rupturing tool (100) from the anatomically widened bone tunnel.

Throughout the description, "back carving" should be understood to mean the action of moving a rupturing element back from a first distal position in a bone tunnel to a second proximal position in the bone tunnel, such that by means of this action the bone tunnel segment travelled by the rupturing element is widened.

Steps d), e) and f) are optional, such that in a particular embodiment a single widening segment is carved. This particular embodiment is particularly indicated for anatomical restorations of the ACL using a single semitendinosus graft which is folded configuring three branches, with two free ends and two bent ends.

In a particular embodiment, the connective tissue on which the preceding method is carried out is a cruciate ligament of the knee joint.

In a particular embodiment, the user who is carrying out the method with the rupturing tool can use a reference ring (116) in order to know the depth of back carving. Said ring (116) is placed around and can move along the longitudinal body (110).

In a particular embodiment, the user carries out the method with the rupturing tool (100) of the invention comprising a rupturing guide (300). In a more particular embodiment, the tool (100) comprises a reference ring (116), which is placed around the longitudinal body (110) and can move along said body (110), which thereby allows knowing the depth of back carving.

More particularly, while widening the straight bone tunnel for ACL, the user places the reference ring (116) touching the proximal end of the first coupling means (322) of the guide arch (320) of the rupturing guide (300) when the distal tip (112) protrudes through the intraarticular opening of the straight bone tunnel to be widened. Then, the user rotates the rupturing tool, including the tubular guide (310), to the desired position and starts the back carving, such that the distance by which the reference ring is separated from the proximal end of the first coupling means (322) indicates to the user the depth of back carving.

Figure 14B:
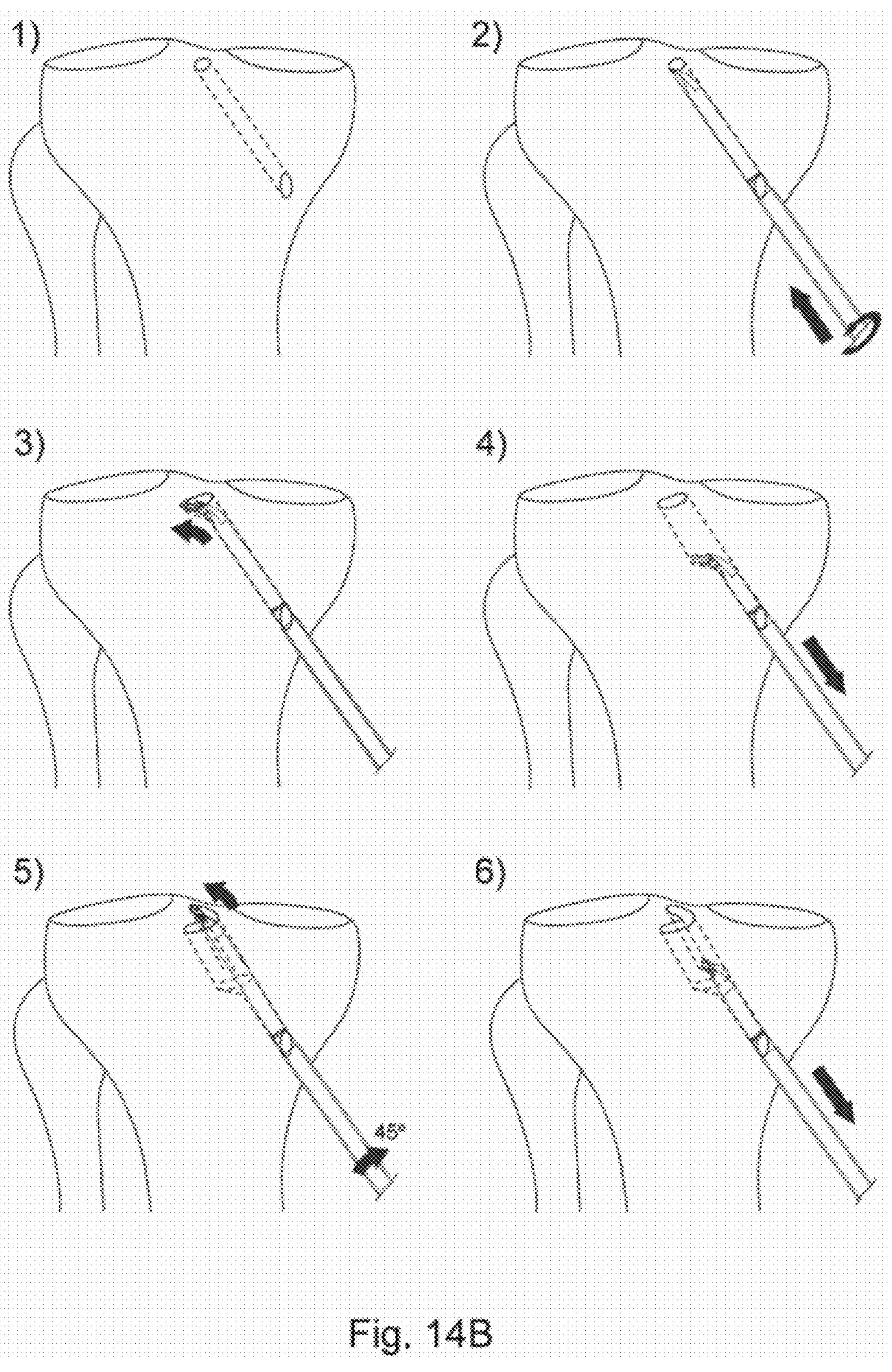

FIG. 14*b* shows the steps of the preceding method performed on the tibia:

1. point 1 shows a straight bone tunnel (4) created by means of a rupturing tool, for example a drill, with an inlet opening in the external bone cortex of the bone to be carved and an outlet opening in the internal bone cortex of said bone;
2. point 2 shows how the longitudinal body (110) of the rupturing tool (100) is introduced through the straight bone tunnel (4) with the rupturing system (500) deactivated;
3. point 3 shows how the rupturing tool (100) is rotated for orienting the second longitudinal axis (102) in a first direction and activating the rupturing system (400, 500), the rupturing element (121) extending through the distal tip (112) of the tool (100);
4. point 4 shows how the rupturing tool (100) is caused to move back a specific distance along the straight bone tunnel (4) to carve a first widening segment (5) of the straight bone tunnel (4); then, the rupturing system (400, 500) would be deactivated and the longitudinal body (110) would be introduced again until the end of the straight bone tunnel (4);
5. point 5 shows how the rupturing tool (100) is rotated for orienting the second longitudinal axis (102) in a second direction, wherein the first direction and the second direction form with respect to one another an approximate angle of 45 degrees; additionally, at this point, the re-activation of the system (500) to extend the rupturing element (121) through the distal tip (112) of the tool (100) is shown;

6. lastly, point 6 shows how the rupturing tool (100) is made to move back a specific distance along the straight bone tunnel (4) to carve the second widening segment (6) of the straight bone tunnel (4).

After these actions, the rupturing system (400, 500) would be deactivated to retract the rupturing element (121), and lastly the rupturing tool (100) would be removed from the straight bone tunnel (4) with first and second widening segments (5, 6).

Figure 14C:
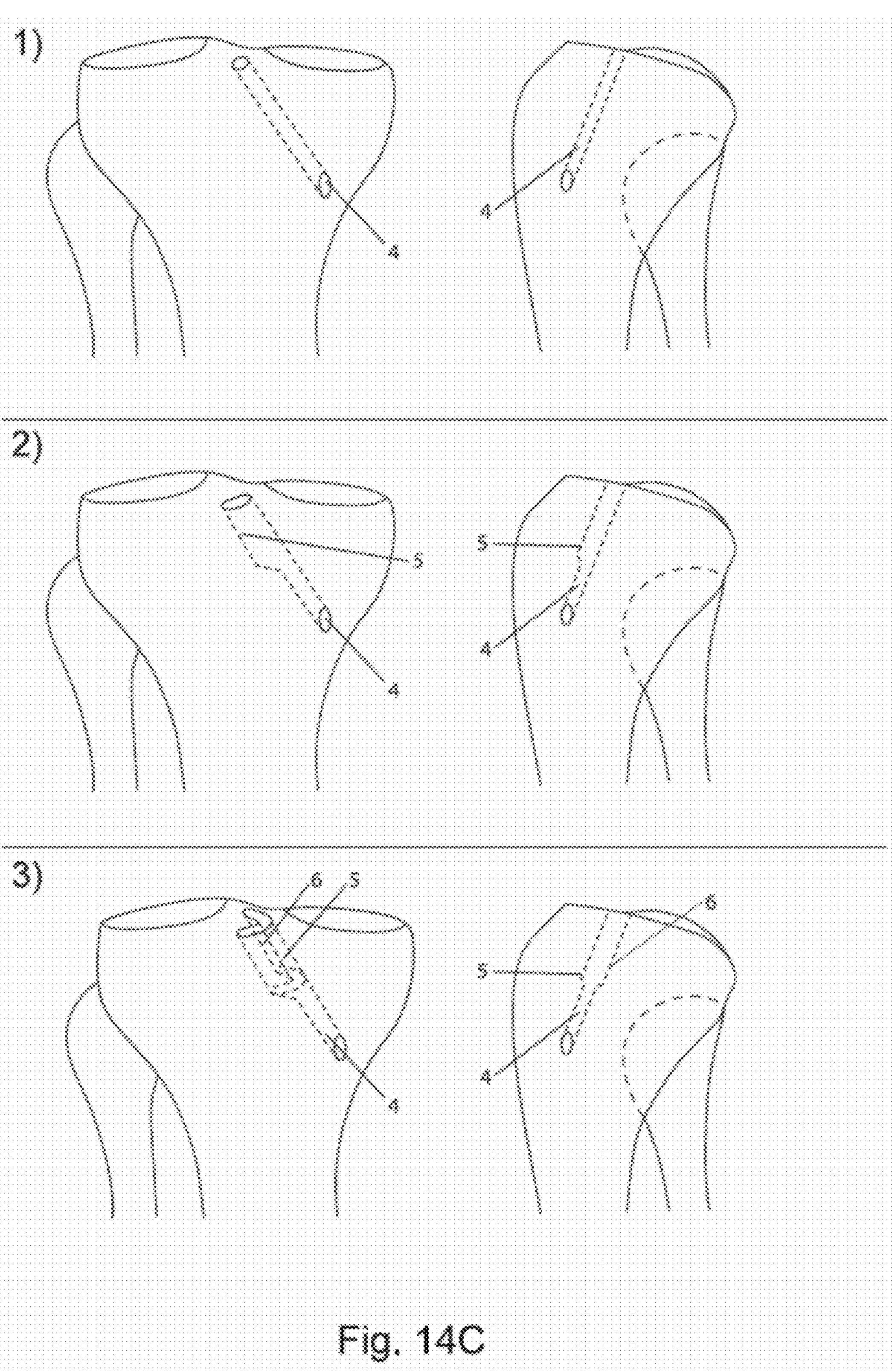

FIG. 14*c* shows in detail the straight bone tunnel (4) with first and second widening segments (5, 6) carved in the tibia:

1) perspective views of the straight bone tunnel (4).

2) perspective views of the straight bone tunnel (4) with a first widening segment (5) carved by means of the rupturing tool of the invention.

3) perspective views of the straight bone tunnel (4) with first and second widening segments (5, 6) carved by means of the rupturing tool of the invention.

Figure 14D:
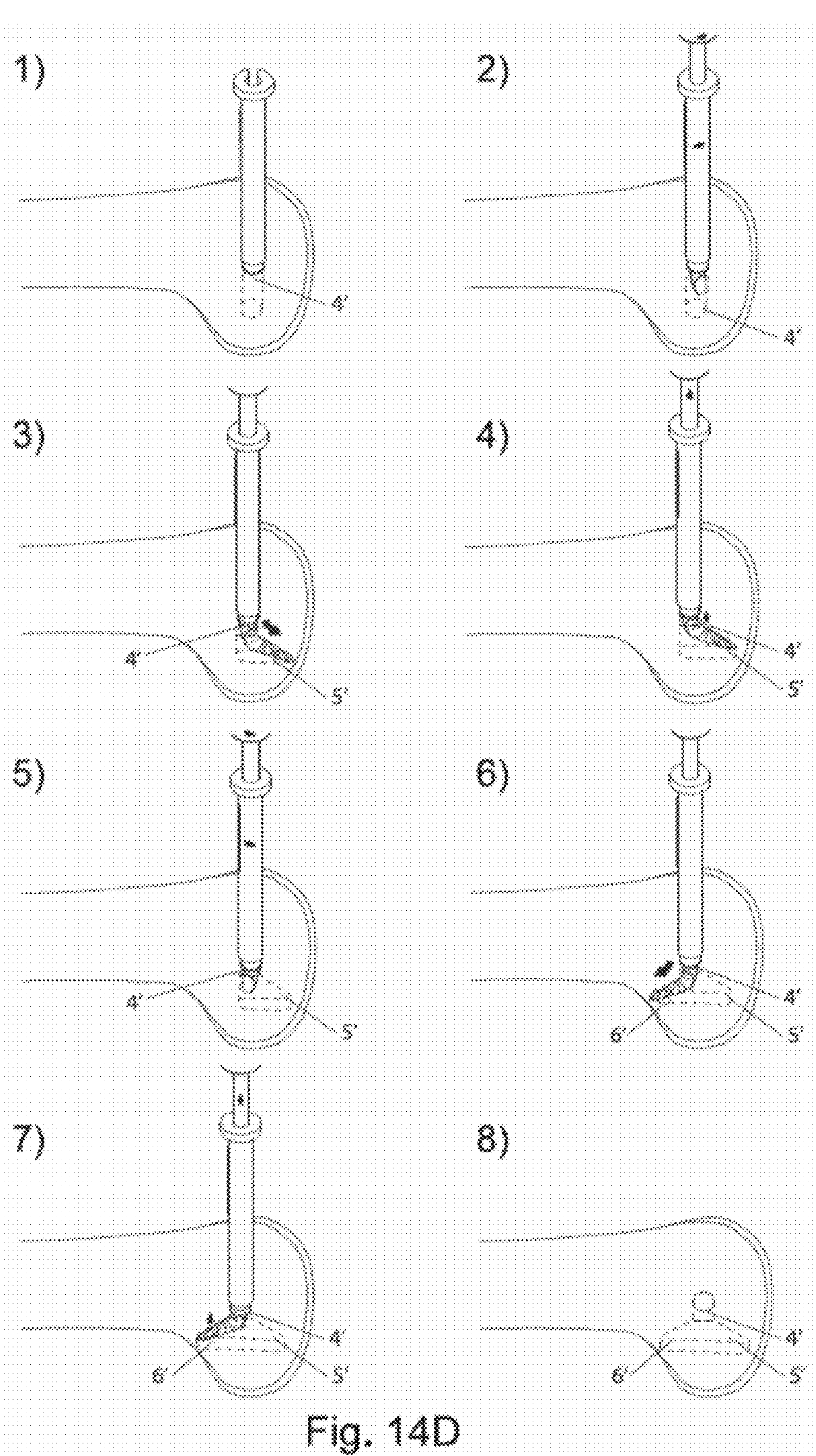

FIG. 14*d* Shows the Steps of the Preceding Method Performed on the Femur:

point 1 shows a straight bone tunnel (4') created by means of a rupturing tool, for example a drill, with an inlet opening in the external bone cortex of the bone to be carved and an outlet opening in the internal bone cortex of said bone, and further shows how the longitudinal body (110) of the rupturing tool (100) is introduced through the straight bone tunnel (4'), with the rupturing system (400, 500) deactivated;

point 2 shows how the rupturing tool (100) is rotated for orienting the second longitudinal axis (102) in a first direction;

points 3 and 4 show the activation of the rupturing system (400, 500), the rupturing element (121) extending through the distal tip (112) of the tool (100) to retrocarve a first widening segment (5') of the straight bone tunnel (4');

point 5 shows the deactivation of the rupturing system (400, 500) and its subsequent rotation, such rotation seeks to orient the second longitudinal axis (102) of the tool (100) in a second direction, wherein the first direction and the second direction form an angle of 180 degrees with respect to one another;

point 6 and 7 show the re-activation of the system (400, 500) to extend the rupturing element (121) through the distal tip (112) of the tool (100) to retrocarve second widening segment (6') of the straight bone tunnel (4');

after these actions, the rupturing system (400, 500) would be deactivated to retract the rupturing element (121) until the second position, and lastly the tool would be removed, leaving a carved straight bone tunnel (4') with first and second widening segments (5',6'), as shown in point 8 of FIG. 14*d*.

Figure 14E:
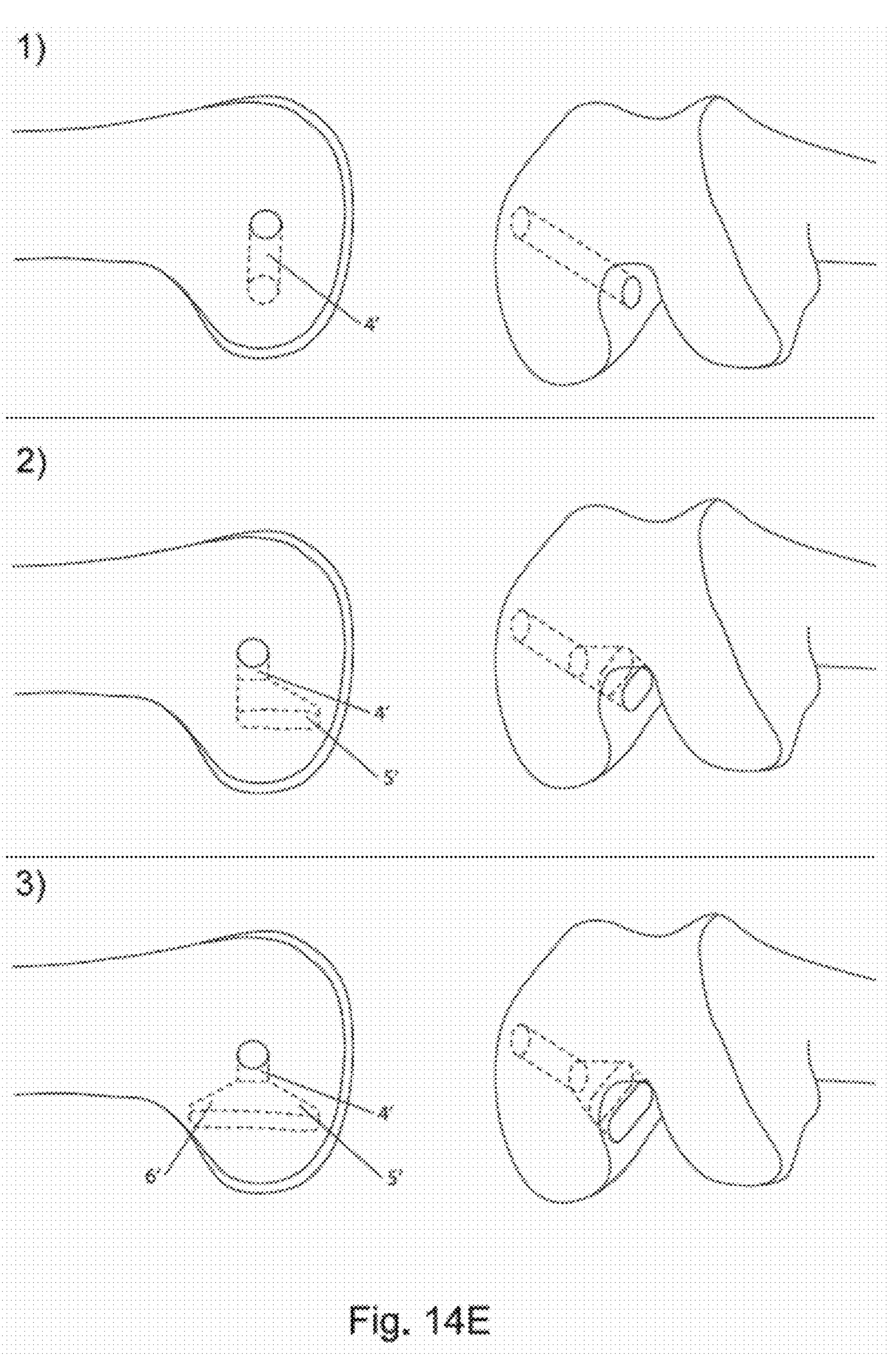

FIG. 14*e* shows in detail the straight bone tunnel (4') with first and second widening segments (5, 6) carved in the femur:

1) perspective views of the straight bone tunnel (4).

2) perspective views of the straight bone tunnel (4) with a first widening segment (5) carved with the system of the invention (500).

3) perspective views of the straight bone tunnel (4) with first and second widening segments (5',6') carved with the system of the invention (400, 500).

In the particular example of reconstructing the anterior cruciate ligament, the intraarticular outlet opening of the bone tunnel to be created must be such that it allows the insertion of fibrous substance which, in the Caucasian population, generally has measurements of between 2 and 4 mm in thickness and between 12 mm and 18 mm in width. However, these particular measurement ranges provided in the preceding examples must be adapted based on the particular anatomy of other populations, based on the particular anatomy of specific patients, and based on the type of implant and/or technique used, and/or on the final application for which the rupturing tool is used, in medicine or veterinary.

Figure 14F:
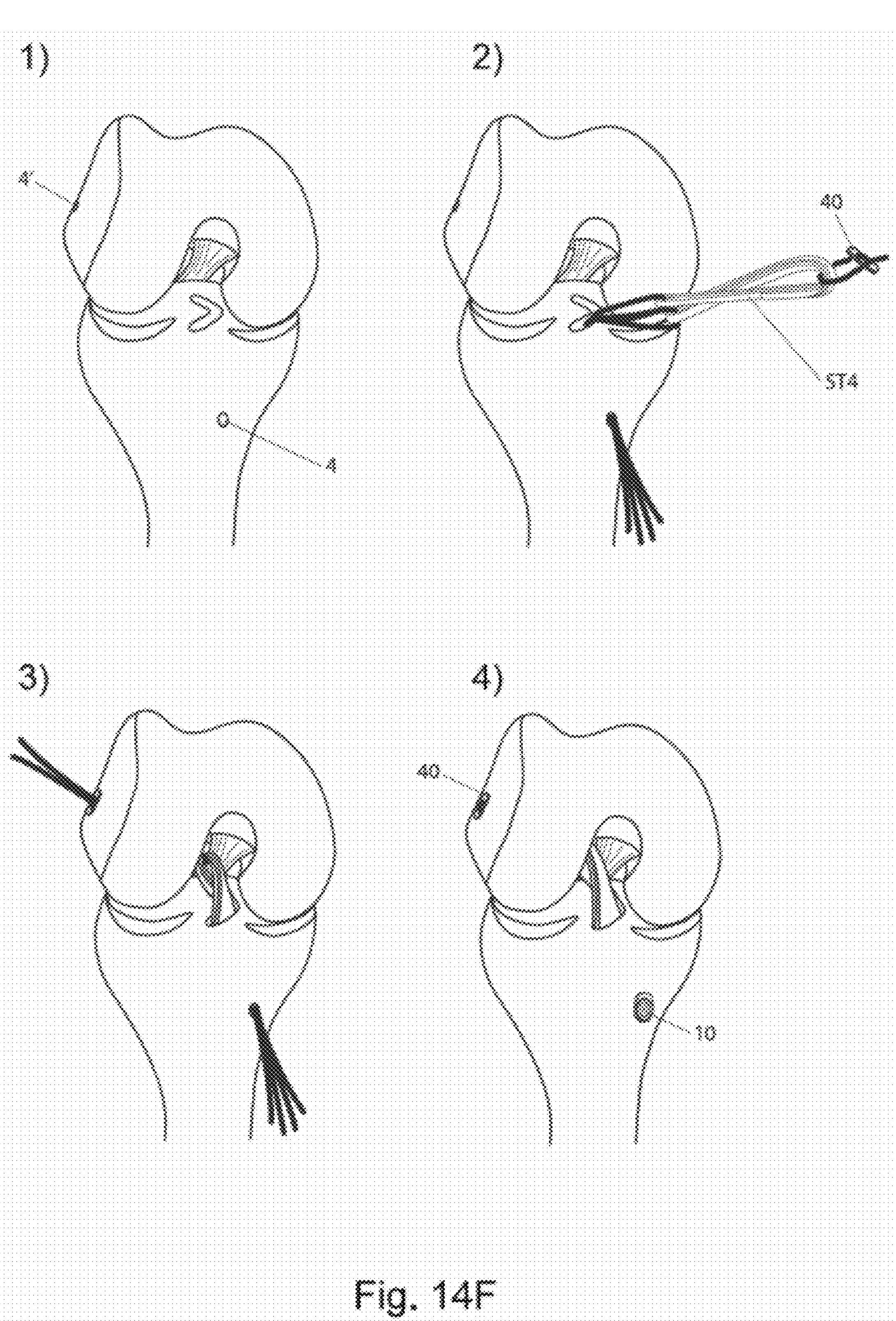

FIG. 14*f* shows a general view of the steps of a method for restoring the anterior cruciate ligament (ACL) of the right knee. In particular, step 1) shows a general view of the joint with the bone tunnels anatomically widened by means of the rupturing tool of the invention. Step 2) illustrates the introduction in the tibial bone tunnel of the suture bands with which both branches of the quadruple-folded semitendinosus graft are pulled into the tibial bone tunnel. Step 3) shows the suture bands at the femoral end of the implant being introduced in the femoral bone tunnel. Step 4) illustrates the anatomical twisting of the implant achieved upon restoring the C-shaped insertion footprint of the original ACL.

Figure 14G:
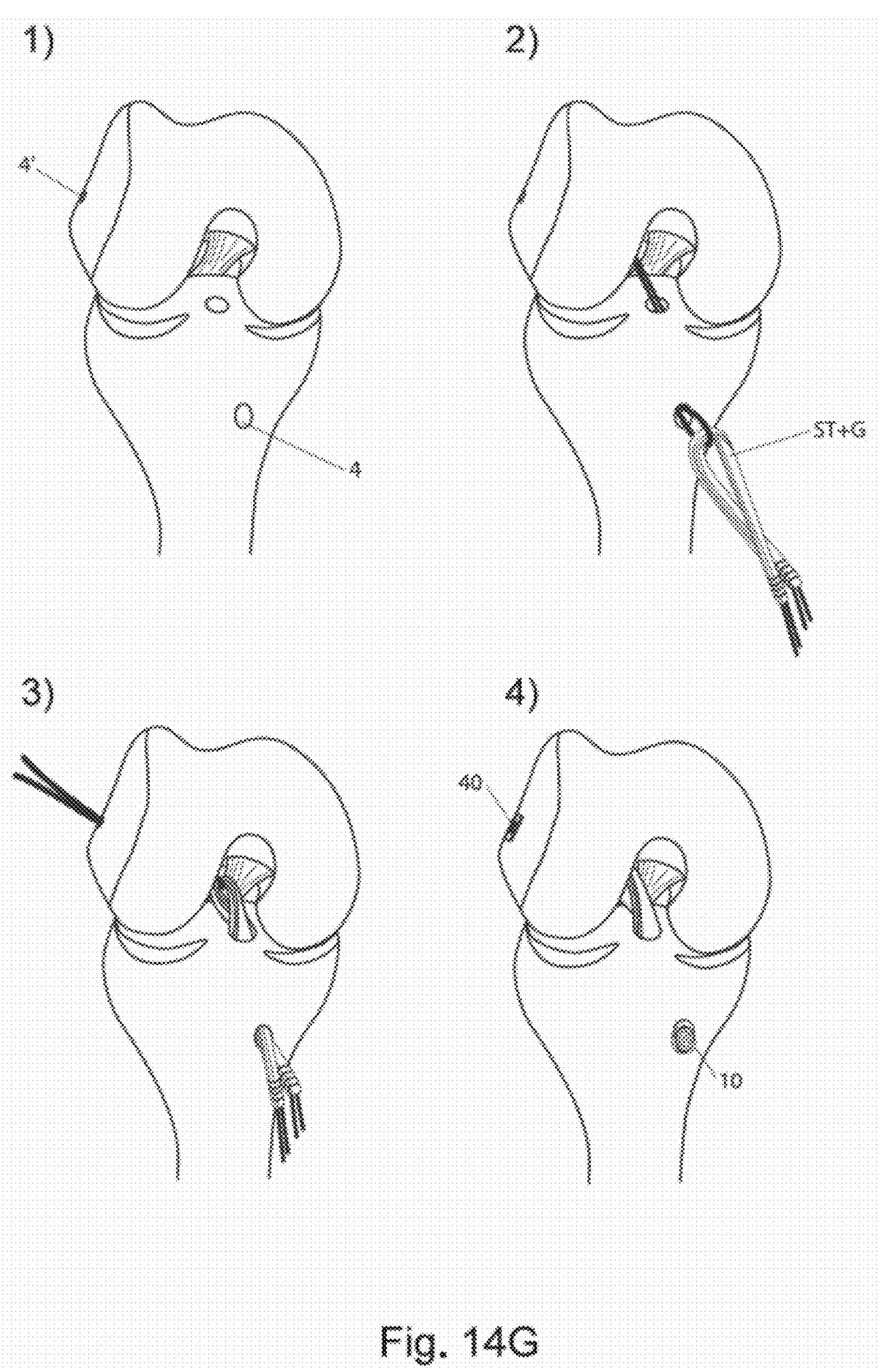

FIG. 14*g* shows a general view of the steps of a method for restoring the anterior cruciate ligament (ACL) of the right knee. In particular, step 1) shows a general view of the joint with the femoral bone tunnel anatomically widened by means of the rupturing tool of the invention, and a conventional cylindrical tibial bone tunnel. Steps 2) and 3) illustrate the introduction of a semitendinosus-gracilis implant in the joint. Step 4) shows the anatomical twisting of the implant which, in this case, is achieved by retaining the ends of the implant on both sides of a cortical fixing device (10) such as the one described in European patent EP3141216 B1 and in European patent application EP3897455 A1.

In a preferred illustrative embodiment as "embodiment 1", it is presented a rupturing tool (100) for minimally invasive surgical interventions, comprising:

a longitudinal body (110) which in turn comprises a main body (111) oriented according to a first longitudinal axis (101); and a distal tip (112) attached to the main body (111) comprising an opening (115) oriented according to at least one second longitudinal axis (102), the distal tip (112) forming a ramp with respect to the main body (111);

wherein the first longitudinal axis (101) and the at least one second longitudinal axis (102) form with respect to one another an angle α equal to or greater than zero degrees, and wherein the first longitudinal axis (101) and the at least one second longitudinal axis (102) are comprised in a first sagittal plane (103);

a rupturing assembly (120) comprising:

a rupturing element (121) comprising a first axis of rupture (121.1) and configured for receiving and performing a rupturing movement about the first axis of rupture (121.1) and for receiving and performing a linear movement, moving along the longitudinal body (110) from a first position to at least one second position, and vice versa, wherein:

if the rupturing element (121) is located in the first position, the rupturing element (121) is oriented according to the first longitudinal axis (101) inside the main body (111); and if the rupturing element (121) is located in the second position, the rupturing element (121) is oriented according to the at least one second longitudinal axis (102) protruding at least partially through the opening (115) of the distal tip (112); and a movement transfer element (122), comprising a proximal part (122.1), a flexible or articulated distal part (122.2), and a second axis of rupture (122.3), the movement transfer element (122) being securely attached to the rupturing element (121) by the flexible or articulated distal part (122.2) and being configured for:

receiving and performing a rupturing movement about the second axis of rupture (122.3) and for transferring the rupturing movement to the rupturing element (121); and receiving and performing a linear movement, moving along the longitudinal body (110); and for transferring the linear movement to the rupturing element (121);

at least one rigidity provision means (130) configured for providing rigidity to the rupturing assembly (120) when the rupturing element (121) is located in the second position protruding at least partially through the opening (115) of the distal tip (112).

"Embodiment 2". The rupturing tool (100) according to the preceding "embodiment", wherein the distal tip (112) is attached to the main body (111):

securely, as a prolongation of said main body (111); or by means of an attachment element configured for positioning the tip (112) in a plurality of angular positions such that, for each of said plurality of angular positions, the at least one second longitudinal axis (102) forms a different angle $\alpha$ with the first longitudinal axis (101).

"Embodiment 3". The rupturing tool (100) according to any of the preceding "embodiments", wherein the rigidity provision means (130) comprises a tubulated element (131) which in turn comprises a proximal portion (131.1) and a distal portion (131.2); wherein the tubulated element (131):

is sized and configured for moving along the longitudinal body (110);

is sized and configured for housing at least partially therein the flexible or articulated distal part (122.1) of the movement transfer element (122), is configured for orienting the distal portion (131.2) according to the first longitudinal axis (101) when the rupturing element (121) is located in the first position; and is configured for orienting the distal portion (131.2) according to the at least one second longitudinal axis (102) when the rupturing element (121) is located in the at least one second position.

"Embodiment 4". The rupturing tool (100) according to the preceding "embodiment", wherein the tubulated element (131) further comprises at least one elongated notch (132) arranged in the distal portion (131.2) forming at least one angle $\beta$ greater than 0 degrees and less than or equal to 90 degrees with respect to the first sagittal plane (103), wherein:

each of the at least one elongated notch (132) separates two different segments (132.1) of the distal portion (131.2) of the tubulated body (131); and the sum of the separations between segments (132.1) of the tubulated body (131) is substantially zero when the rupturing element (121) is located in the at least one second position.

"Embodiment 5". The rupturing tool (100) according to any of "embodiments 3 or 4", wherein the longitudinal body (110) further comprises at least one distal longitudinal groove (114) and the tubulated element (131) further comprises at least one first projection (133), wherein the at least one distal longitudinal groove (114) comprises a distal limit and a proximal limit;

the at least one distal longitudinal groove (114) is sized for receiving the at least one first projection (133) and configured for cooperating with said first projection (133) guiding the tubulated element (131) in the direction of the sagittal plane (103) when the rupturing element (121) moves from the first position to the at least one second position, and vice versa; and the at least one first projection (133) is sized for penetrating the at least one distal longitudinal groove (114) and configured for cooperating with said distal longitudinal groove (114), moving along the distal longitudinal groove (114) when the rupturing element (121) moves from the first position to the at least one second position, and vice versa; and the at least one first projection (133) abuts with a distal limit of the at least one distal longitudinal groove (114) when the rupturing element (121) is located in the at least one second position.

"Embodiment 6". The rupturing tool (100) according to any of the preceding "embodiments", further comprising at least one first attachment and/or coupling means (140) configured for attaching or coupling the movement transfer element (122) to a rupturing movement generator device (200, 200').

"Embodiment 7". The rupturing tool (100) according to any of the preceding "embodiments", further comprising a support body (160.1, 170.1, 180.1) at least partially surrounding the movement transfer element (122) and second attachment and/or coupling means (150) configured for attaching or coupling the support body (160.1, 170.1, 180.1) to a rupturing movement generator device (200, 200').

"Embodiment 8". The rupturing tool (100) according to any of the preceding "embodiments", further comprising a rupturing guide (300) configured for guiding the longitudinal body (110) from an original position to at least one target position, wherein the rupturing guide (300) comprises:

at least one tubular guide (310) which in turn comprises:

a longitudinal conduit (311) with a proximal end (311.1) and a distal end (311.2); the longitudinal conduit (311) comprising a distal appendage (311.3) at the distal end (311.2); and a striking edge (312), a prolongation of the longitudinal conduit (311) at the proximal end (311.1); and wherein the longitudinal conduit (311) is configured for housing therein the longitudinal body (110), wherein the at least one tubular guide (310) is oriented according to a first longitudinal guiding axis (321.1); and the striking edge (312) is configured for receiving a striking force in the direction of the first longitudinal guiding axis (321.1); and a guide arch (320) which in turn comprises:

a proximal arch portion (321) which in turn comprises a first coupling means (330) configured for securely coupling and uncoupling the proximal arch portion (321) with respect to the tubular guide (310) in a plurality of different positions along the first longitudinal guiding axis (321.1);

a distal arch portion (322) which in turn comprises a distal tip (322.2) oriented according to a second longitudinal guiding axis (322.1);

second coupling means (340) configured for coupling the distal arch portion (322) to the proximal arch portion (321) in a plurality of different positions, such that for each of said positions the first longitudinal guiding axis (321.1) and the at least one second longitudinal guiding axis (322.1) form a different angle $\alpha2$ with respect to one another; and the first longitudinal guiding axis (321.1) and the at least one second longitudinal guiding axis (322.1) are comprised in a second sagittal plane (301).

"Embodiment 9". The rupturing tool (100) according to the preceding "embodiment", wherein the at least one tubular guide (310) further comprises a hole (314) which in turn comprises a first portion (314.1) and a second portion (314.2) and the main body (111) of the longitudinal body (110) comprises at least one second projection (113);

the first portion (314.1) of the hole (314) is sized and configured for receiving and guiding the second projection (113) from a proximal location to the second portion (314.2) when the longitudinal body (110) of the rupturing tool (100) is inserted into and moves along the inside of the at least one tubular guide (310) of the rupturing guide (300); and the second portion (314.2) is sized and configured for abutting with the second projection (113) when the first sagittal plane (103) of the rupturing tool (100) is rotated an angle $\gamma$ with respect to the second sagittal plane (301) of the rupturing guide (300).

"Embodiment 10". The rupturing tool (100) according to "embodiment 8", wherein the at least one tubular guide (310) further comprises at least one longitudinal hole (314) and the main body (111) of the longitudinal body (110) comprises at least one second projection (113);

wherein the at least one longitudinal hole (314) is sized and configured for receiving and guiding the at least one second projection (113) from a proximal location to a distal location and vice versa.

"Embodiment 11". The rupturing tool (100) according to "embodiments 9 or 10", wherein the rupturing guide (300) comprises a plurality of tubular guides (320), wherein:

the dimensions of the hole (314); and/or the shape of the hole (314); and/or the dimensions of the first portion (314.1) of the hole (314); and/or the shape of the first portion (314.1) of the hole (314); and/or the dimensions of the second portion (314.2) of the hole (314); and/or the shape of the second portion (314.2) of the hole (314) of each of the tubular guides (320) is/are different from one another.

"Embodiment 12". The rupturing tool (100) according to any of "embodiments 8-11", wherein the distal appendage (311.3) comprises:

a trilobular tip; or two tips; or a beveled recess; or polyhedral faces.

"Embodiment 13". The rupturing tool (100) according to any of the preceding "embodiments", wherein the rupturing movement is a rotational movement and the rupturing tool (100) further comprises a movement transmission and conversion means (160, 170, 180) configured for:

receiving the rotational movement from a rotational movement generator device (200, 200');

converting the rotational movement into a linear and/or reciprocating movement;

transmitting the linear and/or reciprocating movement to the movement transfer element (122) such that said movement transfer element (122) transfers the linear and/or reciprocating movement to the rupturing element (121) causing it to move from the first position to the at least one second position;

ceasing the linear and/or reciprocating movement when the rotational movement ceases, causing the rupturing element (121) to move from the at least one second position to the first position.

"Embodiment 14". The rupturing tool (100) according to the preceding "embodiment", wherein the rupturing movement generator device (200, 200') is a drilling device (200, 200') and the movement transmission and conversion means (160) comprises:

a first longitudinal rotary movement transmission element (161) couplable to a movement transmission shaft of the drilling device (200, 200'), the first longitudinal element (161) being configured for receiving the rotary movement from the drilling device (200, 200') and for performing said rotary movement;

a second longitudinal rotary movement transmission element (162), attached to the proximal part (122.1) of the movement transfer element (122) and configured for receiving a rotary movement from the first longitudinal element (161) and for performing said rotary movement and a linear movement;

a brake actuator (163) connected to the second longitudinal element (162) and configured for exerting a force for retaining rotation on the second longitudinal element (162), a return spring (164) configured for exerting a linear return force on the second longitudinal element (162); and a helical sliding coupling (165) configured for coupling the first longitudinal element (161) to the second longitudinal element (162);

wherein the helical sliding coupling (165) in turn comprises a longitudinal coupling portion (161.1) attached to the first longitudinal element (161) comprising a first thread (161.2) on its outer surface; and a longitudinal coupling conduit (162.1) attached to the second longitudinal element (162) comprising a second thread (162.2) on its inner surface;

wherein the first thread (161.2) of the longitudinal coupling portion (161.1) and the second thread (162.2) of the longitudinal coupling conduit (162.1) are configured for cooperating with one another such that a linear movement of the longitudinal coupling conduit (162.1) with respect to the longitudinal coupling portion (161.1) occurs when the longitudinal coupling conduit (162.1) performs a rotary movement and the longitudinal coupling portion (161.1) rotates at a speed less than the longitudinal coupling conduit (162.1), the thread direction of the helical sliding coupling (165) being in reverse with respect to the direction of the rotary movement of the drilling device.

"Embodiment 15". The rupturing tool (100) according to "embodiment 13", wherein the rupturing movement generator device (200, 200') is a drilling device (200, 200') and the movement transmission and conversion means (170) comprises:

a male-female sliding coupling (173) comprising:

a primary rotor (171) couplable to a movement transmission shaft of the drilling device (200, 200'), the primary rotor (171) being configured for receiving a rotary movement from the drilling device (200, 200') and for performing said rotary movement;

a secondary rotor (172) slidingly coupled to the primary rotor (171) at its proximal end and attached to the proximal part (122.1) of the movement transfer element (122) at its distal end; wherein the secondary rotor (172) further comprises a groove or indentation (172.1) with a sinusoidal geometry on its outer face; and wherein the secondary rotor (172) is configured for moving linearly in both directions with respect to the primary rotor (171) as a result of the sliding coupling;

a return spring (174) configured for exerting a return force on the secondary rotor (172); and a manual activation control (175) connected to a fixed plunger (176), the manual activation control (175) being configured for causing the fixed plunger (176) to penetrate the groove or indentation (172.1) of the secondary rotor (172);

wherein, when the secondary rotor (172) receives the rotary movement from the primary rotor (171) and performs said rotary movement, the activation of the control (175) causes the fixed plunger (176) to penetrate the groove or indentation (172.1), causing the secondary rotor (172) to perform a linear reciprocating forward and backward movement with respect to the primary rotor (171), and wherein the secondary rotor (172) transmits said linear reciprocating forward and backward movement, in combination with the rotary movement, to the movement transfer element (122), the movement transfer element (122) in turn transmitting the linear reciprocating forward and backward movement, in combination with the rotary movement, to the rupturing element (121), and, wherein, upon removing the fixed plunger (176) from the groove or indentation (172.1) by the deactivation of the control (175), the secondary rotor (172) performs a return movement pushed by the return spring (174) in the distal-proximal direction.

"Embodiment 16". The rupturing tool (100) according to "embodiment 13", wherein the rupturing movement generator device (200, 200') is a drilling device (200, 200') and the movement transmission and conversion means (180) comprises:

a male-female sliding coupling (183) comprising:

a primary rotor (181) couplable to a movement transmission shaft of the drilling device (200, 200'), the primary rotor (181) being configured for receiving a rotary movement from the drilling device (200, 200') and for performing said rotary movement;

a secondary rotor (182) slidingly coupled to the primary rotor (181) at its proximal end; wherein the secondary rotor (182) is configured for moving linearly in both directions with respect to the primary rotor (181) as a result of the sliding coupling, and wherein the secondary rotor (182) comprises a rotary pressure generator device (185);

a return spring (184) configured for exerting a return force on the secondary rotor (182);

a fluidic compartment comprising a first chamber (186), a second chamber (187), and a fluid (188); wherein the first chamber (186) and second chamber (187) are in fluidic communication and the fluid (188) is arranged inside the chambers (186, 187);

the rotary pressure generator device (185) is immersed in the fluid (188), arranged between the first chamber (186) and second chamber (187); and the secondary rotor (182) is attached to the proximal part (122.1) of the movement transfer element (122); and wherein:

when the secondary rotor (182) receives a rotary movement from the primary rotor (181) and performs said rotary movement, the rotary pressure generator device (185) in turn receives said rotary movement and generates a thrust force greater than the return force of the return spring (184), causing the fluid (188) to flow from the first chamber (186) to the second chamber (187);

the flow of the fluid (188) causes the secondary rotor (182) to perform a linear movement in the proximal-distal direction;

the secondary rotor (182) transmits the linear movement, in combination with the rotary movement, to the movement transfer element (122), the movement transfer element (122) in turn transmitting the linear movement, in combination with the rotary movement, to the rupturing element (121), and, when the secondary rotor (182) stops receiving the rotary movement from the primary rotor (181), the secondary rotor (182) performs a linear movement in the distal-proximal direction pushed by the return spring (184).

"Embodiment 17". a rupturing system (400) for minimally invasive surgical interventions, comprising:

a rupturing movement generator device (200, 200') configured for generating and performing a rupturing movement;

at least one rupturing tool (100) according to any of the preceding "embodiments"; couplable to the rupturing movement generator device (200, 200') at least by means of the movement transfer element (122);

and wherein the rupturing movement generator device (200, 200') is further configured for transferring the rupturing movement to the movement transfer element (122).

"Embodiment 18". the rupturing system (500) for minimally invasive surgical interventions comprising:

a rupturing movement and linear and/or reciprocating movement generator device (200') configured for generating and performing a rupturing movement and a linear and/or reciprocating movement;

at least one rupturing tool (100) according to any of "embodiments 1 to 12", couplable to the rupturing movement and linear and/or reciprocating movement generator device (200') at least by means of the movement transfer element (122); wherein the rupturing movement and linear and/or reciprocating movement generator device (200') is further configured for transferring the rupturing movement and the linear and/or reciprocating movement to the movement transfer element (122).

"Embodiment 19". The rupturing system (500) according to the preceding "embodiment", wherein the rupturing movement and linear and/or reciprocating movement generator device (200') comprises mechanical and/or electronic and/or electromagnetic means.

The invention claimed is:

1. A rupturing tool for minimally invasive surgical interventions for the creation of bone tunnels suitable for the proper anatomical reconstruction of tendons and ligaments, the rupturing tool comprising:

a longitudinal body comprising;

a main body oriented according to a first longitudinal axis; and a distal tip attached to the main body comprising an opening oriented according to at least one second longitudinal axis, the distal tip forming a ramp with respect to the main body;

wherein the first longitudinal axis and the at least one second longitudinal axis form with respect to one another an angle a greater than zero degrees, and wherein the first longitudinal axis and the at least one second longitudinal axis are comprised in a first sagittal plane;

a rupturing assembly comprising:

a rupturing element comprising a first axis of rupture and configured for receiving and performing a rupturing movement about the first axis of rupture and for receiving and performing a linear movement, moving along the longitudinal body from a first position to at least one second position, and vice versa, wherein:

when the rupturing element is located in the first position, the rupturing element is oriented according to the first longitudinal axis inside the main body; and when the rupturing element is located in the second position, the rupturing element is oriented according to the at least one second longitudinal axis protruding at least partially through the opening of the distal tip; and a movement transfer element, comprising a proximal part, a flexible or articulated distal part, and a second axis of rupture, the movement transfer element being securely attached to the rupturing element by the flexible or articulated distal part and being configured for:

receiving and performing a rupturing movement about the second axis of rupture and for transferring the rupturing movement to the rupturing element; and receiving and performing a linear movement, moving along the longitudinal body; and for transferring the linear movement to the rupturing element;

at least one rigidity provision means configured for providing rigidity to the rupturing assembly when the rupturing element is located in the second position protruding at least partially through the opening of the distal tip;

wherein the rigidity provision means comprises a tubulated element which in turn comprises a proximal portion and a distal portion; wherein the tubulated element:

is sized and configured for moving along the longitudinal body;

is sized and configured for housing at least partially therein the flexible or articulated distal part of the movement transfer element, is configured for orienting the distal portion according to the first longitudinal axis when the rupturing element is located in the first position; and is configured for orienting the distal portion according to the at least one second longitudinal axis when the rupturing element is located in the at least one second position.

2. The rupturing tool of claim 1, wherein the distal tip is attached to the main body:

securely, as a prolongation of said main body; or by means of an attachment element configured for positioning the tip in a plurality of angular positions such that, for each of said plurality of angular positions, the at least one second longitudinal axis forms a different angle a with the first longitudinal axis.

3. The rupturing tool of claim 1, wherein the first axis of rupture is:

an axis of rotation about which the rupturing element performs a rotation; or an axis of vibration about which the rupturing element performs a vibratory movement.

4. The rupturing tool of claim 1, wherein the tubulated element further comprises at least one elongated notch arranged in the distal portion forming at least one angle β greater than 0 degrees and less than or equal to 90 degrees with respect to the first sagittal plane, wherein:

each of the at least one elongated notch separates two different segments of the distal portion of the tubulated body; and the sum of the separations between segments of the tubulated body is substantially zero when the rupturing element is located in the at least one second position.

5. The rupturing tool of claim 1, wherein the longitudinal body further comprises at least one distal longitudinal groove and the tubulated element further comprises at least one first projection, wherein the at least one distal longitudinal groove comprises a distal limit and a proximal limit;

the at least one distal longitudinal groove is sized for receiving the at least one first projection and configured for cooperating with said first projection guiding the tubulated element in the direction of the sagittal plane when the rupturing element moves from the first position to the at least one second position, and vice versa; and the at least one first projection is sized for penetrating the at least one distal longitudinal groove and configured for cooperating with said distal longitudinal groove, moving along the distal longitudinal groove when the rupturing element moves from the first position to the at least one second position, and vice versa; and the at least one first projection abuts with a distal limit of the at least one distal longitudinal groove when the rupturing element is located in the at least one second position.

6. The rupturing tool of claim 1, further comprising at least one first attachment and/or coupling means configured for attaching or coupling the movement transfer element to a rupturing movement generator device.

7. The rupturing tool of claim 1, further comprising a support body at least partially surrounding the movement transfer element and second attachment and/or coupling means configured for attaching or coupling the support body to a rupturing movement generator device.

8. The rupturing tool of claim 1, further comprising a rupturing guide configured for guiding the longitudinal body from an original position to at least one target position, wherein the rupturing guide comprises:

at least one tubular guide which in turn comprises:

a longitudinal conduit with a proximal end and a distal end;

the longitudinal conduit comprising a distal appendage at the distal end; and a striking edge, a prolongation of the longitudinal conduit at the proximal end; and wherein the longitudinal conduit is configured for housing therein the longitudinal body, wherein the at least one tubular guide is oriented according to a first longitudinal guiding axis; and the striking edge is configured for receiving a striking force in the direction of the first longitudinal guiding axis; and a guide arch which in turn comprises:

a proximal arch portion which in turn comprises a first coupling means configured for securely coupling and uncoupling the proximal arch portion with respect to the tubular guide in a plurality of different positions along the first longitudinal guiding axis;

a distal arch portion which in turn comprises a distal tip oriented according to a second longitudinal guiding axis;

second coupling means configured for coupling the distal arch portion to the proximal arch portion in a plurality of different positions, such that for each of said positions the first longitudinal guiding axis and the at least one second longitudinal guiding axis form a different angle $\alpha_2$ with respect to one another; and the first longitudinal guiding axis and the at least one second longitudinal guiding axis are comprised in a second sagittal plane.

9. The rupturing tool of claim 8, wherein:

the at least one tubular guide further comprises a hole which in turn comprises a first portion and a second portion, and the main body of the longitudinal body comprises at least one second projection;

the first portion of the hole is sized and configured for receiving and guiding the second projection from a proximal location to the second portion when the longitudinal body of the rupturing tool is inserted into and moves along the inside of the at least one tubular guide of the rupturing guide; and the second portion is sized and configured for abutting with the second projection when the first sagittal plane of the rupturing tool is rotated an angle y with respect to the second sagittal plane of the rupturing guide.

10. The rupturing tool of to claim 8, wherein:

the at least one tubular guide further comprises at least one longitudinal hole and the main body of the longitudinal body comprises at least one second projection;

wherein the at least one longitudinal hole is sized and configured for receiving and guiding the at least one second projection from a proximal location to a distal location and vice versa.

11. The rupturing tool of claim 9, wherein the rupturing guide comprises a plurality of tubular guides, wherein:

the dimensions of the hole; and/or the shape of the hole; and/or the dimensions of the first portion of the hole; and/or the shape of the first portion of the hole; and/or the dimensions of the second portion of the hole; and/or the shape of the second portion of the hole of each of the tubular guides is/are different from one another.

12. The rupturing tool of claim 8, wherein the distal appendage comprises:

a trilobular tip; or two tips; or a beveled recess; or polyhedral faces.

13. The rupturing tool of claim 1, wherein the rupturing movement is a rotational movement and the rupturing tool further comprises a movement transmission and conversion means configured for:

receiving the rotational movement from a rotational movement generator device;

converting the rotational movement into a linear and/or reciprocating movement;

transmitting the linear and/or reciprocating movement to the movement transfer element such that said movement transfer element transfers the linear and/or reciprocating movement to the rupturing element causing it to move from the first position to the at least one second position; and ceasing the linear and/or reciprocating movement when the rotational movement ceases, causing the rupturing element to move from the at least one second position to the first position.

14. The rupturing tool of claim 6, wherein the rupturing movement generator device is a drilling device and the movement transmission and conversion means comprises:

a first longitudinal rotary movement transmission element couplable to a movement transmission shaft of the drilling device, the first longitudinal element being configured for receiving the rotary movement from the drilling device and for performing said rotary movement;

a second longitudinal rotary movement transmission element-(162), attached to the proximal part of the movement transfer element and configured for receiving a rotary movement from the first longitudinal element and for performing said rotary movement and a linear movement;

a brake actuator connected to the second longitudinal element and configured for exerting a force for retaining rotation on the second longitudinal element, a return spring configured for exerting a linear return force on the second longitudinal element; and a helical sliding coupling configured for coupling the first longitudinal element to the second longitudinal element;

wherein the helical sliding coupling in turn comprises a longitudinal coupling portion attached to the first longitudinal element comprising a first thread on its outer surface; and a longitudinal coupling conduit attached to the second longitudinal element comprising a second thread on its inner surface;

wherein the first thread of the longitudinal coupling portion and the second thread of the longitudinal coupling conduit are configured for cooperating with one another such that a linear movement of the longitudinal coupling conduit with respect to the longitudinal coupling portion occurs when the longitudinal coupling conduit performs a rotary movement and the longitudinal coupling portion rotates at a speed less than the longitudinal coupling conduit, the thread direction of the helical sliding coupling being in reverse with respect to the direction of the rotary movement of the drilling device.

15. The rupturing tool of claim 13, wherein the rupturing movement generator device is a drilling device and the movement transmission and conversion means comprises:

a male-female sliding coupling comprising:

a primary rotor couplable to a movement transmission shaft of the drilling device, the primary rotor being configured for receiving a rotary movement from the drilling device and for performing said rotary movement;

a secondary rotor slidingly coupled to the primary rotor at its proximal end and attached to the proximal part of the movement transfer element at its distal end; wherein the secondary rotor further comprises a groove or indentation with a sinusoidal geometry on its outer face; and wherein the secondary rotor is configured for moving linearly in both directions with respect to the primary rotor as a result of the sliding coupling;

a return spring configured for exerting a return force on the secondary rotor; and a manual activation control connected to a fixed plunger, the manual activation control being configured for causing the fixed plunger to penetrate the groove or indentation of the secondary rotor;

wherein, when the secondary rotor receives the rotary movement from the primary rotor and performs said rotary movement, the activation of the control causes the fixed plunger to penetrate the groove or indentation, causing the secondary rotor to perform a linear reciprocating forward and backward movement with respect to the primary rotor, and wherein the secondary rotor transmits said linear reciprocating forward and backward movement, in combination with the rotary movement, to the movement transfer element, the movement transfer element in turn transmitting the linear reciprocating forward and backward movement, in combination with the rotary movement, to the rupturing element, and, wherein, upon removing the fixed plunger from the groove or indentation by the deactivation of the control, the secondary rotor performs a return movement pushed by the return spring in the distal-proximal direction.

16. The rupturing tool of claim 13, wherein the rupturing movement generator device is a drilling device and the movement transmission and conversion means comprises:

a male-female sliding coupling comprising:

a primary rotor couplable to a movement transmission shaft of the drilling device, the primary rotor being configured for receiving a rotary movement from the drilling device and for performing said rotary movement;

a secondary rotor slidingly coupled to the primary rotor at its proximal end; wherein the secondary rotor is configured for moving linearly in both directions with respect to the primary rotor as a result of the sliding coupling, and wherein the secondary rotor comprises a rotary pressure generator device;

a return spring configured for exerting a return force on the secondary rotor;

a fluidic compartment comprising a first chamber, a second chamber, and a fluid; wherein the first chamber and second chamber are in fluidic communication and the fluid is arranged inside the chambers;

the rotary pressure generator device is immersed in the fluid, arranged between the first chamber and second chamber; and the secondary rotor is attached to the proximal part of the movement transfer element; and wherein:

when the secondary rotor receives a rotary movement from the primary rotor and performs said rotary movement, the rotary pressure generator device in turn receives said rotary movement and generates a thrust force greater than the return force of the return spring, causing the fluid to flow from the first chamber to the second chamber;

the flow of the fluid causes the secondary rotor to perform a linear movement in the proximal-distal direction;

the secondary rotor transmits the linear movement, in combination with the rotary movement, to the movement transfer element, the movement transfer element in turn transmitting the linear movement, in combination with the rotary movement, to the rupturing element, and, when the secondary rotor stops receiving the rotary movement from the primary rotor, the secondary rotor performs a linear movement in the distal-proximal direction pushed by the return spring.

17. A rupturing system for minimally invasive surgical interventions, comprising:

a rupturing movement generator device configured for generating and performing a rupturing movement;

at least one rupturing tool according to claim 1, couplable to the rupturing movement generator device at least by means of a movement transfer element;

and wherein the rupturing movement generator device is further configured for transferring the rupturing movement to the movement transfer element.

18. A rupturing system for minimally invasive surgical interventions comprising:

a rupturing movement and linear and/or reciprocating movement generator device configured for generating and performing a rupturing movement and a linear and/or reciprocating movement;

at least one rupturing tool according to claim 1, couplable to the rupturing movement and linear and/or reciprocating movement generator device at least by means of a movement transfer element; wherein the rupturing movement and linear and/or reciprocating movement generator device is further configured for transferring the rupturing movement and the linear and/or reciprocating movement to the movement transfer element.

19. The rupturing system of claim 18, wherein the rupturing movement and linear and/or reciprocating movement generator device comprises mechanical and/or electronic and/or electromagnetic means.

* * * * *